US010968456B2

(12) United States Patent
Turner et al.

(10) Patent No.: US 10,968,456 B2
(45) Date of Patent: Apr. 6, 2021

(54) GENERATION OF BIOMASS

(71) Applicant: Stora Enso OYJ, Helsinki (FI)

(72) Inventors: Simon Turner, Manchester (GB); Laxmi Mishra, Salford (GB); Manoj Kumar, Sale Cheshire (GB); Peter Etchells, Davis, CA (US)

(73) Assignee: Stora Enso OYJ, Helsinki (FI)

( * ) Notice: Subject to any disclaimer, the term of this patent is extended or adjusted under 35 U.S.C. 154(b) by 316 days.

(21) Appl. No.: 15/555,129

(22) PCT Filed: Mar. 1, 2016

(86) PCT No.: PCT/IB2016/051131
§ 371 (c)(1),
(2) Date: Sep. 1, 2017

(87) PCT Pub. No.: WO2016/139579
PCT Pub. Date: Sep. 9, 2016

(65) Prior Publication Data
US 2018/0037900 A1    Feb. 8, 2018

Related U.S. Application Data

(60) Provisional application No. 62/126,965, filed on Mar. 2, 2015.

(51) Int. Cl.
*C12N 15/82* (2006.01)
(52) U.S. Cl.
CPC ..... *C12N 15/8223* (2013.01); *C12N 15/8261* (2013.01); *Y02A 40/146* (2018.01)
(58) Field of Classification Search
None
See application file for complete search history.

(56) References Cited

U.S. PATENT DOCUMENTS

| 5,495,007 | A | 2/1996 | Thompson et al. | |
|---|---|---|---|---|
| 7,220,895 | B2 * | 5/2007 | Fischer | C07K 14/415 800/287 |
| 10,023,878 | B2 * | 7/2018 | Turner | C12N 15/8218 |
| 2003/0159180 | A1 | 8/2003 | Fischer et al. | |

FOREIGN PATENT DOCUMENTS

WO    2010029357    3/2010
WO    WO 2010/029357 A2 *    3/2010

OTHER PUBLICATIONS

Bowie et al, (1990, "Deciphering the Message in Protein Sequences: Tolerance to Amino Acid Substitutions", Science 247:1306-1310).*
McConnell et al, (2001, "Radial Patterning of *Arabidopsis* Shoots by Class III HD-ZIP and Kanadi Genes", Nature 411 (6838):709-713).*
Jaglo et al (2001, "Components of the *Arabidopsis* C-Repeat/Dehydration-Responsive Element Binding Factor Cold-Response Pathway Are Conserved in *Brassica napus* and Other Plant Species", Plant Physiology 127(3):910-917).*
Oommenn et al (1994, "The Elicitor-Inducible Alfalfa Isoflavone Reductase Promoter Confers Different Patterns of Developmental Expression in Homologous and Heterologous Transgenic Plants", The Plant Cell 6:1789-1803).*
Brucker et al (Planta (2005) 220:864-874).*
Etchells, J. P. et al "The PXY-CLE41 receptor ligand pair defines a multifunctional pathway that controls the rate and orientation of vascular cell division", Development, 2010, pp. 767-774, vol. 137.
Qiang, Y. et al "CLE peptides in vascular development", Journal of integrative plant biology, 2013, pp. 389-394, vol. 55.
Hirakawa, Y. et al "Non cell-autonomous control of vascular stem cell fate by a CLE peptide/receptor system", PNAS, 2008, pp. 15208-15213, vol. 105.
Risopatron, J. P. M. et al "The vascular cambium: molecular control of cellular structure", Protoplasma, 2010, pp. 145-161, vol. 247.
Etchells, J. P. et al "Wood formation in trees is increased by manipulating PXY-regulated cell division", Current Biology, 2015, pp. 1050-1055, vol. 25.
Wang, R. et al "Vascular expression of Populus LRR-RLK genes and the effects of their overexpression on wood formation", Mol Breeding, 2015, pp. 1-12, vol. 35.
International Search Report for PCT/IB2016/051131, dated Jun. 29, 2016.
Zhang, Jing, et al. "The Formation of Wood and Its Control." Current Opinion in Plant Biology, vol. 17, 2014, pp. 56-63., doi:10.1016/j.pbi.2013.11.003.

* cited by examiner

*Primary Examiner* — Stuart F Baum
(74) *Attorney, Agent, or Firm* — Greer, Burns & Crain, Ltd.

(57) ABSTRACT

The present invention relates to a method for manipulating the growth and/or structure of a plant, for increasing biomass. The method of the invention is achieved by increasing the expression and/or activity of PXY and/or CLE in the vascular tissue of a plant.

13 Claims, 25 Drawing Sheets

Specification includes a Sequence Listing.

A wild type

B 35S::PttCLE41

C pxy

D pxy 35S::PttPXY

PttPXY amino acid (SEQ. ID. 9) sequence:

MKLPFLFFPLAFFFYLFKPPLVVFSATTLPPPLQSLLSIKIFLK

DPSNTFHDWNLSNTSGLIQEPVWCSWSGIKCNPATAQITSLDLSHRNLSGVIPAEIRY

LTSLVHLNLSGNAFDGLLQPAIFELGDLRILDISHNNFNSTFPPGISKLKFLRVFNAY

SNNFTGPLPKEFVWLRFLEELSLGGSYFTGEIPRSYGSFLRLKYLHLAGNELEGPLPP

DLGSLSQLEHLELGYHPLLSGNVPEEFALLTNLKYLDISKCNLTGSLPPQLGNLTKLE

NLLLFMNQFTGEIPVSYTNLKALKALDLSVNQLSGAIPEGLSSLRELNRLSLLKNQLT

GEIPPGIGELPYLDTLELWNNNLTGVLPQKLGSNGNLLWLDVSNSSLSGFIPPNLCHG

NRLYKLTLFSNRFLGKLPDSLANCTSLSRFRIQDNQLNGSIPYGLGLLPNLSYVDLSK

NNFTGEIPDDLGYSEPLHYLNISGNSFHTALPNNIWSAPNLQIFSASSCKLVSKIPDF

IGCSSLYRIELQDNMFNGSIPRDIGHCERLISLNLSRNSLTGIIPWEISTLPAIAAVD

LSHNLLTGSIPSNFGNCSILESFNVSYNLLTGPIPASGTIFPNLHPSSFSGNQGLCGG

VLPKPCAADTLGAGEMEVRHRQOPKRTAGAIVWIMAAAFGIGLFVLVAGTRCFHANYG

RRFSDEREIGPWKLTAFQRLNFIADDVLECLSMSDKILGMGSTGTVYKAEMPGGEIIA

VKKLWGKHKENIKRRRGVLAEVDVLGNVRHRNIVRLLGCCSNRECTMLLYEVMPNGNL

HDLLHGRNKGDNLVGDWLTRYKIALGVAQGICYLHHDCDFVIVHRDLKPSNILLDGEM

EARVADFGVAKLIQSDESMSVIAGSYGYIAPEYAYTLQVDERSDIYSYGVVLMEIISG

KRSVDSEFGDGNSIVDWVRPKIKAKDGVNDILDKDAGASIAYVREEMMQMLRIALLCT

SRNPADRPSMREVVLMLQEAKPKRKLPGSIVSVGSGDHIVTVDGAIAQKPAVEC

Figure 13B (cont'd)

PttPXY nucleotide (SEQ. ID. 9) sequence:

```
ORIGIN
        1 atgaaactcc ctttcttttt ctttccactt gcgttcttct tctacctgtt caaacctcct
       61 cttgtagtgt tctctgctac gactctgcct cccccctcc aatctcttct ctccattaag
      121 accttcctca aagaccottc caataogttc catgattgga acttgtccaa cactagtggc
      181 ttaatccaag aaccagtttg gtgctcgtgg tccggcatca agtgcaaccc agccactgct
      241 caaatcacat cactcgatct ctctcaccgg aatctttctg gtgtaattcc agctgagatt
      301 agatacttaa cgagcctggt tcacttgaat ttgagtggaa atgcttttga tgggcttctc
      361 caacctgcca tttttgaact gggtgacctt aggattcttg acatcagcca caacaacttc
      421 aattcaacat tcccacctgg gatttccaag ctcaagttct tgagagtctt caatgcatac
      481 agcaacaact tcactggtcc attgcctaaa gaattcgtct ggctgcgctt cctggaggag
      541 ctcagccttg gtgggagcta cttcacggga gagattccaa ggagttatgg aagtttcctc
      601 agattgaagt acctgcactt agctgggaat gaattggaag gaccattgcc accgacttga
      661 ggatccttga gtcagctcga gcacctcgag cttggctacc atccactcct atcaggcaat
      721 gtaccagaag aatttgcttt gctgaccaat ctcaagtacc tagatatctc aaagtgtaat
      781 ctaacaggca gtctcccacc acaacttgga aatcttacca aactcgagaa tttgctcctt
      841 ttcatgaacc agtttactgg tgaaatcccg gtgagctaca caaatctgaa agctctaaaa
      901 gcacttgatt tatccgttaa tcagctttca ggggcaattc cagagggtt atcttccttg
      961 aaagagctaa acaggttgag cttgctgaaa aatcagctca ccggcgaaat accaccggga
     1021 attggcgagc taccatacct tgacacatta gagctctgga caacaacct aaccggagtt
     1081 ctccggcaaa agcttggatc caatgggaat ctactatggc ttgacgtctc aaacagttcg
     1141 ctctccggcc caattcctcc aaatctatgc catggaaaca agctttacaa gctgattctg
     1201 ttctccaaca gtttctcgg taaattacca gattctctag caaactgcac ctctttgtcc
     1261 aggttccgaa ttcaagacaa ccagctcaac ggctcaatcc cttatggatt aggtctcctg
     1321 cctaatcttt cctatgtgga tttaagcaag aataacttca caggtgaaat tcctgacgat
     1381 cttggctatt cagaaccact tcattacttg aacatttctg gaaactcctt ccacactgct
     1441 ttaccaaaca acatatggag cgcgccaaat cttcagattt tttcagccag ctcatgcaag
     1501 ctcgtgagca aaataccaga ttttatcggt tgcagcagtc tgtacaggat agaattgcaa
     1561 gacaatatgt tcaatggcag cattccacgg gatatcggcc attgtgagag gtccatttcg
     1621 cttaatttaa gccgcaattc tcttactggt attattccgt gggagattc tacacttcct
     1681 gctatcgctg ctgtcgattt gtcccataat ttactcaccg gttccattcc ttcaaatttt
     1741 ggtaactgtt caactttgga gagttttaat gtgtcctata atttgttaac tggacccatt
     1801 cctgcatcgg gtacaatatt tccaaatttg catccgtctt cctttcgggg caatcaagga
     1861 ttatgcggtg gcgttttgcc aaagccttgt gctgcggata cattgggggc tggagaaatg
     1921 gaggtccgcc atagacagca gcccaaaagg actgctggcg ctatagtgtg gattatggcg
     1981 gctgcttttg gtattggatt atttgtgctt gttgctggga ctaggtgttt ccatgcgaac
     2041 tatggccgta gatttagtga tgaacgagag atcggaccgt ggaaattaac tgcctttcaa
     2101 cggttgaatt tcacggcaga cgatgtgctc gagtgtctat ctatgtcgga caagatctta
     2161 gggatggggt caacgggac ggtctataag gcggaaatgc caggtggcga gatcatagcg
     2221 gtgaagaaac tgtggggtaa gcataaggag aacatcaaaa ggaggagagg ggtgttagcc
     2281 gaggtggatg ttttaggtaa cgtgaggcat aggaatatag tgagattgct aggatgttgc
     2341 agtaacaggg agtgtacaat gttgctgtac gagtacatgc ctaatggtaa cttacatgat
     2401 ttgttgcatg ggaaaaacas gggagacaat ttggtgggtg attggcttac aagtacaagg
     2461 attgcactgg gagtggcaca ggggatttgc tatttgcatc atgattgtga tcctgtgatt
```

Figure 13B (cont'd)

```
2521 gtgcaccgag atcttaagcc tagtaatata ttattggacg gtgagatgga ggctagagtg
2581 gcagattttg gggtggcaaa gctgatccaa agtgacgaat ccatgtcagt cattgctggg
2641 tcttatggct acattgcgcc aggtacggtc ctggtcccat tgctgcttct cttttatttt
2701 ttttatgaga ttgttgtg ccttcaagt gcatttcacc ttacgagtag aaaacagaaa
2761 acgtgggtaa tttgaattg aaattcgatc gtcaacagtc gactttgta agaatacaga
2821 gtcctgtct cgtactgcag tgaagaactg gatcaattag ttaaggtcgt gtaataaaac
2881 aaaacaaaag aggaaagaca aatgtgttac gagtaggacg gttgatttta ggacggaaag
2941 catagaaatt atatcttctt gcttggagat cctcaatgta tcttcttcgc ttgcttttct
3001 ttctttctgc cgtatttgca tacacaggac tagattgaag ctggtctcgt ttgaaattcc
3061 tggataccct ttgtctatgt ttgcttagtt cgttctgctg gtatatctag aatatggagt
3121 gtcaaatctt gaaacaggac atgggaatta gagtaatta catccgaaa acactttctt
3181 ttattttatt tcttgattgt tttgccatga aagcatcca tccatacttg attttccaaa
3241 tgcaaaaaaa ggagcggtaa atactacagt acagagtgca gtggtggggt ggggtggacg
3301 tcatttcttc ttttgggccg cgaatttgca actgttcgag acctttgagt gcgtgcgca
3361 ctcactattg cgcgtggacg ctctccttat tattattttt tccttttaaa ttctcctttt
3421 ccctcaagc ctttttttt gggtagattt accatgtaca gttggaccca cgaataattt
3481 ctttagatc ctcgcattca ttgcagtttt tgacttctcg atgcacttgc catgatttct
3541 ttctttgttg gattgagttg ggtcactgaa atcttgctt taccgtgcag agtatgctta
3601 cacactgcag gttgatgaga agagtgatat ttatagttat ggggtggtgt taatggagat
3661 tataagcggc aagaggtcgg tcgattctga gttcggggat ggtaacagca ttgttgactg
3721 ggtaaggccg aagataaagg ctaaggacgg tgtaaatgac atttagaca aggatgctgg
3781 ggcatcgatt gcatatgtga gggaagaaat gatgcaaatg cttagaattg ctttgctatg
3841 caccagccgg aatccggcgg accgaccgtc gatgagggat gtcgtgttga tgctgcaaga
3901 agccaagccc aagaggaaac tgccgggaag tatagttagt gttggtagtg gtgaccacat 3961 tgttactgtt gatgggcta ttgcacaaaa gcctgcagtc gaatgttaa
```

Figure 13C

PXY protein sequence (SEQ. ID. 6):

```
MKKKNISPSLVLHPLLLLLLPFFAFNSLALKFSPQLLSLLSLKTSLSGPPSAFQDWKVPVNGQND
AVWCSWSGVVCDNVTAQVISLDLSHRNLSGRIPIQIRYLSSLLYLNLSGNSLEGSFPTSIFDLTKL
TTLDISRNSFDSSFPPGISKLKFLKVFNAFSNNFEGLLPSDVSRLRFLEELNFGGSYFEGEIPAAY
GGLQRLKFIHLAGNVLGGKLPPRLGLLTELQHMEIGYNHFNGNIPSEFALLSNLKYFDVSNCSLS
GSLPQELGNLSNLETLFLFQNGFTGEIPESYSNLKSLKLLDFSSNQLSGSIPSGFSTLKNLTWLS
LISNNLSGEVPEGIGELPELTTLFLWNNNFTGVLPHKLGSNGKLETMDVSNNSFTGTIPSSLCHG
NKLYKLILFSNMFEGELPKSLTRCESLWRFRSQNNRLNGTIPIGFGSLRNLTFVDLSNNRFTDQIP
ADFATAPVLQYLNLSTNFFHRKLPENIWKAPNLQIFSASFSNLIGEIPNYVGCKSFYRIELQGNSL
NGTIPWDIGHCEKLLCLNLSQNHLNGIIPWEISTLPSIADVDLSHNLLTGTIPSDFGSSKTITTFNV
SYNQLIGPIPSGSFAHLNPSFFSSNEGLCGDLVGKPCNSDRFNAGNADIDGHHKEERPKKTAGA
IVWILAAAIGVGFFVLVAATRCFQKSYGNRVDGGGRNGGDIGPWKLTAFQRLNFTADDVVECLS
KTDNILGMGSTGTVYKAEMPNGEIIAVKKLWGKNKENGKIRRRKSGVLAEVDVLGNVRHRNIVR
LLGCCTNRDCTMLLYEYMPNGSLDDLLHGGDKTMTAAAEWTALYQIAIGVAQGICYLHHDCDPV
IVHRDLKPSNILLDADFEARVADFGVAKLIQTDESMSVVAGSYGYIAPEYAYTLQVDKKSDIYSYG
VILLEIITGKRSVEPEFGEGNSIVDWVRSKLKTKEDVEEVLDKSMGRSCSLIREEMKQMLRIALL
CTSRSPTDRPPMRDVLLILQEAKPKRKTVGDNVIVVGDVNDVNFEDVCSVDVGHDVKCQRIGV
```

Figure 13C (cont'd)

PXY DNA sequence without intron (SEQ. ID. 7):

```
ATGAAAAAGAAGAACATTTCTCCTTCTCTTGTTCTTCATCCCCTTCTCCTTCTTCTACTTCCT
TTCTTTGCTTTCAATTCCTTAGCTCTCAAGTTTTCACCTCAACTCTTGTCTCTCCTTTCCCTT
AAAACATCTCTCTCTGGCCCTCCCTCTGCCTTTCAAGACTGGAAAGTCCCCGTTAACGGTC
AAAACGACGCCGTTTGGTGTTCTTGGTCCGGTGTAGTCTGTGATAATGTAACGGCTCAAGT
CATTTCCCTCGACCTCTCTCACCGGAACCTCTCTGGTCGTATTCCTATACAGATTCGTTACT
TGTCGAGCTTACTCTACTTAAATCTCAGTGGGAATTCTTTGGAAGGTTCGTTTCCAACTTCT
ATCTTTGATCTCACCAAGCTCACTACCCTCGACATCAGCCGTAACTCGTTCGACTCGAGTT
TTCCTCCCGGAATCTCCAAGCTTAAGTTCTTAAAAGTCTTCAATGCGTTCAGCAACAACTTC
GAAGGTCTATTACCTAGTGACGTGTCTCGTCTTCGTTTCTTGGAAGAGCTTAACTTTGGTG
GAAGTTACTTTGAAGGAGAGATTCCAGCAGCTTACGGTGGTTTACAGAGATTGAAGTTTAT
TCATTTAGCTGGAAATGTCCTCGGAGGTAAACTACCTCCTAGATTAGGACTCTTAACAGAGC
TCCAACACATGGAAATCGGTTATAATCACTTCAACGGAAACATACCTTCGGAGTTTGCCTTA
CTCTCAAATCTCAAGTACTTTGACGTTTCCAATTGCAGCCTCTCTGGTTCTCTGCCTCAAG
AACTCGGGAATCTCTCAAACCTAGAGACTTTATTTCTATTCCAAAACGGTTTCACCGGTGAA
ATCCCAGAGAGTTATAGCAACTTGAAATCCCTCAAGCTTCTCGATTTTTCGAGTAATCAGCT
TTCTGGTAGTATCCCATCAGGCTTCTCGACCTTGAAGAACCTCACATGGCTAAGCTTAATCA
GCAATAACCTCTCAGGTGAAGTACCTGAAGGAATCGGTGAACTCCCTGAGCTTACTACATT
GTTTCTATGGAACAATAACTTCACCGGAGTTTTGCCACACAAGCTTGGATCAAACGGTAAA
CTTGAGACAATGGACGTCTCTAACAATTCATTCACCGGAACAATCCCTTCTTCTCTCTGCCA
TGGAAACAAGCTATACAAACTCATCCTCTTCTCCAACATGTTTGAAGGTGAGCTACCAAAG
AGCTTGACTCGTTGCGAATCTCTATGGCGGTTTCGGAGTCAAAACAATCGATTAAACGGCA
CAATTCCGATCGGATTCGGCTCTCTACGTAACCTCACTTTCGTTGATTTAAGCAACAACAGA
TTCACCGATCAAATTCCGGCGGATTTCGCCACCGCTCCTGTTCTTCAGTACTTGAATCTCT
CAACCAATTTCTTCCACAGGAAACTACCGGAAAACATATGGAAAGCTCCGAATCTACAGAT
CTTCTCAGCGAGTTTCAGCAATTTGATCGGTGAAATCCCAAATTACGTTGGATGCAAAAGC
TTCTACAGGATTGAACTACAAGGAAACTCACTCAACGGAACGATTCCATGGGACATCGGAC
ATTGCGAGAAGCTTCTCTGTTTGAATCTCAGCCAAAATCATCTCAACGGAATCATTCCATGG
GAGATTTCAACTCTTCCGTCAATCGCCGACGTAGATCTTTCTCATAATCTCTTAACCGGAAC
AATCCCTTCCGATTTCGGAAGCTCTAAGACGATCACAACCTTCAACGTTTCGTATAATCAGC
TAATCGGTCCGATTCCAAGTGGTTCTTTCGCTCATCTGAATCCGTCGTTCTTCCTCAAAC
GAAGGACTCTGTGGAGATCTCGTCGGAAAACCTTGCAATTCTGATAGGTTTAACGCCGGA
AATGCAGATATAGACGGTCATCATAAAGAGGAACGACCTAAGAAAACAGCCGGAGCTATTG
TTTGGATATTGGCGGCGGCGATTGGGGTTGGATTCTTCGTCCTTGTAGCCGCCACTAGATG
CTTCCAGAAAAGCTACGGAAACAGAGTCGACGGTGGTGGAAGAAACGGCGGAGATATAG
GACCGTGGAAGCTAACGGCTTTTCAGAGACTAAACTTCACGGCGGATGATGTGGTTGAGT
GTCTCTCAAAGACTGATAACATCCTCGGAATGGGATCAACAGGAACAGTGTACAAAGCAGA
GATGCCTAATGGAGAAATAATCGCCGTGAAAAAACTTTGGGGAAAAACAAAGAGAACGG
CAAAATCCGGCGGCGGAAGAGCGGCGTATTGGCGGAGGTTGATGTTCTAGGGAACGTAC
GTCACCGGAACATCGTTCGTCCTTGGATGTTGCACGAATCGAGATTGCACGATGCTTTT
ATACGAATACATGCCTAATGGAAGCTTAGACGATCTTCTTCACGGTGGGGATAAGACGATG
ACCGCGGCGGCGGAATGGACGGCTTTGTATCAGATCGCGATTGGAGTGGCTCAAGGGAT
CTGTTATCTCCACCATGATTGTGATCCGGTGATTGTACACCGTGACCTGAAACCTAGCAATA
TCCTCCTCGACGCCGATTTCGAGGCGCGTGTGGCGGACTTCGGCGTCGCGAAGCTTATT
CAAACCGACGAATCCATGTCCGTCGTCGCCGGTTCGTACGGTACATTGCACCAGAATATG
CTTACACTTTACAAGTGGATAAAAAGAGTGATATCTATAGCTATGGAGTGATTTATTAGAGAT
AATCACCGGAAAAGATCGGTGGAACCGGAATTTGGAGAAGGTAACAGTATCGTGGATTG
GGTTAGATCAAAGTTGAAGACGAAAGAAGATGTAGAAGAAGTTCTAGACAAAAGCATGGGT
AGGTCGTGTAGTCTTATAAGAGAAGAGATGAAACAAATGTTGAGAATTGCGTTGTTGTGTAC
AAGCCGGAGTCCGACAGACAGACCGCCGATGAGAGATGTTGTTGATTCTTCAAGAGGC
AAAGCCAAAGAGGAAGACAGTAGGGGATAATGTGATCGTCGTTGGTGATGTTAATGATGTC
AATTTCGAAGATGTTTGTAGTGTTGATGTTGGTCATGATGTTAAATGTCAAAGGATTGGGGT
GTGA
```

Figure 13C (cont'd)

PXY DNA sequence with intron (SEQ. ID. 8):

```
ATGAAAAAGAAGAACATTTCTCCTTCTCTTGTTCTTCATCCCCTTCTCCTTCTTCTACTTCCTT
TCTTTGCTTTCAATTCCTTAGCTCTCAAGTTTTCACCTCAACTCTTGTCTCTCCTTTCCCTTAA
AACATCTCTCTGGCCCTCCCTCTGCCTTTCAAGACTGGAAAGTCCCCGTTAACGGTCAA
AACGACGCCGTTTGGTGTTCTTGGTCCGGTGTAGTCTGTGATAATGTAACGGCTCAAGTCAT
TTCCCTCGACCTCTCTCACCGGAACCTCTCTGGTCGTATTCCTATACAGATTCGTTACTTGTC
GAGCTTACTCTACTTAAATCTCAGTGGGAATTCTTTGGAAGGTTCGTTTCCAACTTCTATCTT
TGATCTCACCAAGCTCACTACCCTCGACATCAGCCGTAACTCGTTCGACTCGAGTTTTCCTC
CCGGAATCTCCAAGCTTAAGTTCTTAAAAGTCTTCAATGCGTTCAGCAACAACTTCGAAGGT
CTATTACCTAGTGACGTGTCTCGTCTTCGTTTCTTGGAAGAGCTTAACTTTGGTGGAAGTTA
CTTTGAAGGAGAGATTCCAGCAGCTTACGGTGGTTTACAGAGATTGAAGTTTATTCATTTAGC
TGGAAATGTCCTCGGAGGTAAACTACCTCCTAGATTAGGACTCTTAACAGAGCTCCAACACA
TGGAAATCGGTTATAATCACTTCAACGGAAACATACCTTCGGAGTTTGCCTTACTCTCAAATC
TCAAGTACTTTGACGTTTCCAATTGCAGCCTCTCTGGTTCTCTGCCTCAAGAACTCGGGAAT
CTCTCAAACCTAGAGACTTTATTTCTATTCCAAAACGGTTTCACCGGTGAAATCCCAGAGAG
TTATAGCAACTTGAAATCCCTCAAGCTTCTCGATTTTTCGAGTAATCAGCTTTCTGGTAGTATC
CCATCAGGCTTCTCGACCTTGAAGAACCTCACATGGCTAAGCTTAATCAGCAATAACCTCTC
AGGTGAAGTACCTGAAGGAATCGGTGAACTCCCTGAGCTTACTACATTGTTTCTATGGAACA
ATAACTTCACCGGAGTTTTGCCACACAAGCTTGGATCAAACGGTAAACTTGAGACAATGGAC
GTCTCTAACAATTCATTCACCGGAACAATCCCTTCTTCTCTGCCATGGAAACAAGCTATAC
AAACTCATCCTCTTCTCCAACATGTTTGAAGGTGAGCTACCAAAGAGCTTGACTCGTTGCGA
ATCTCTATGGCGGTTTCGGAGTCAAAACAATCGATTAAACGGCACAATTCCGATCGGATTCG
GCTCTCTACGTAACCTCACTTTCGTTGATTTAAGCAACAACAGATTCACCGATCAAATTCCGG
CGGATTTCGCCACCGCTCCTGTTCTTCAGTACTTGAATCTCTCAACCAATTTCTTCCACAGG
AAACTACCGGAAAACATATGGAAAGCTCCGAATCTACAGATCTTCTCAGCGAGTTTCAGCAA
TTTGATCGGTGAAATCCCAAATTACGTTGGATGCAAAGCTTCTACAGGATTGAACTACAAG
GAAACTCACTCAACGGAACGATTCCATGGGACATCGGACATTGCGAGAAGCTTCTCTGTTT
GAATCTCAGCCAAAATCATCTCAACGGAATCATTCCATGGGAGATTTCAACTCTTCCGTCAAT
CGCCGACGTAGATCTTTCTCATAATCTCTTAACCGGAACAATCCCTTCCGATTTCGGAAGCT
CTAAGACGATCACAACCTTCAACGTTTCGTATAATCAGCTAATCGGTCCGATTCCAAGTGGTT
CTTTCGCTCATCTGAATCCGTCGTTCTTCTCCTCAAACGAAGGACTCTGTGGAGATCTCGTC
GGAAAACCTTGCAATTCTGATAGGTTTAACGCCGGAAATGCAGATATAGACGGTCATCATAAA
GAGGAACGACCTAAGAAAACAGCCGGAGCTATTGTTTGGATATTGGCGGCGGCGATTGGG
GTTGGATTCTTCGTCCTTGTAGCCGCCACTAGATGCTTCCAGAAAAGCTACGGAAACAGAG
TCGACGGTGGTGGAAGAAACGGCGGAGATATAGGACCGTGGAAGCTAACGGCTTTTCAGA
GACTAAACTTCACGGCGGATGATGTGGTTGAGTGTCTCTCAAAGACTGATAACATCCTCGGA
ATGGGATCAACAGGAACAGTGTACAAAGCAGAGATGCCTAATGGAGAAATAATCGCCGTGA
AAAAACTTTGGGGAAAAAACAAAGAGAACGGCAAAATCCGGCGGCCGGAAGAGCGGCGTAT
TGGCGGAGGTTGATGTTCTAGGGAACGTACGTCACCGGAACATCGTTCGTCTCCTTGGATG
TTGCACGAATCGAGATTGCACGATGCTTTTATACGAATACATGCCTAATGGAAGCTTAGACGA
TCTTCTTCACGGTGGGGATAAGACGATGACCGCGGCGGCGGAATGGACGGCTTTGTATCA
GATCGCGATTGGAGTGGCTCAAGGGATCTGTTATCTCCACCATGATTGTGATCCGGTGATTG
TACACCGTGACCTGAAACCTAGCAATATCCTCCTCGACGCCGATTTCGAGGCGCGTGTGGC
GGACTTCGGCGTCGCGAAGCTTATTCAAACCGACGAATCCATGTCCGTCGTCGCCGGTTC
GTACGGTTACATTGCACCAGgtacccttaactttttttgattattcttttacttttcccccaaatttttaaatttttgtcccttttgttt
ttattattcgaatttttgtccgtttgttaaacattcttttttgttgggatgacaacatctgacaaatatgactaaaatttttaatttttgtttgtttttggttaca
gAATATGCTTACACTTTACAAGTGGATAAAAGAGTGATATCTATAGCTATGGAGTGATTTTATT
AGAGATAATCACCGGAAAAGATCGGTGGAACCGGAATTTGGAGAAGGTAACAGTATCGTG
GATTGGGTTAGATCAAAGTTGAAGACGAAAGAAGATGTAGAAGAAGTTCTAGACAAAGCAT
GGGTAGGTCGTGTAGTCTTATAAGAGAAGAGATGAAACAAATGTTGAGAATTGCGTTGTTGT
GTACAAGCCGGAGTCCGACAGACAGACCGCCGATGAGAGATGTGTTGTTGATTCTTCAAGA
GGCAAAGCCAAAGAGGAAGACAGTAGGGGATAATGTGATCGTCGTTGGTGATGTTAATGAT
GTCAATTTCGAAGATGTTTGTAGTGTTGATGTTGGTCATGATGTTAAATGTCAAAGGATTGGG
GTGTGA
```

Fig. 14A

Alignment of CLE41 and CLE42 and homologous sequences from other plant species

CLE41 protein sequence (SEQ. ID. 1)

MATSNDQTNTKSSHSRTLLLLFTFLSLLLFSSLTIPMTRHQSTSMVAPFKRVLLESS
VPASSTMDLRPKASTRRSRTSRRREFGNDAHEVPSGPNPISN

CLE41 DNA sequence (SEQ. ID. 2)

ATGGCAACATCAAATGACCAAACCAATACTAAATCATCACATTCTCGTACTCT
TCTCCTTCTCTTCATCTTCTTATCCCTCCTTCTCTTCAGTAGCCTTACAATCCCC
ATGACTCGTCATCAGTCCACATCTATGGTTGCTCCCTTCAAGAGGGTTCTCC
TCGAATCTTCAGTTCCAGCTTCATCAACAATGGATCTACGTCCAAAGGCTAGC
ACACGACGCAGCCGCACTTCTAGAAGGAGAGAGTTTGGAAATGATGCTCATG
AGGTTCCTAGTGGTCCAAACCCTATTTCCAACTAG

Fig 14B

CLE41 Ptt protein sequence (SEQ. ID. 4)

MATPKTQSRTISDHQTCTKAHHFLSLLALLFIFILLTSTKPIN
PTNMAASISIKRLLLESSEPASTTMNLHPKQNQDARISSSSSTS
SSKSTRTKSGAAAHEVPSGPNPISNR"

CLE41 Ptt DNA sequence (SEQ. ID. 5)

```
  1 tagctagcct tggtgctggt tcatggatat tgcaccctct tgggctcttg ggggtggttt
 61 ctttcgtcta ttaactgcat ggcaacacca aaaacacaat caaggacaat cagtgatcat
121 caaacatgca caaagcaca ccattcctt tcattgcttg cacttctttt catttttatt
181 ttactcacta cctccaccaa acccataaac ccaacaaata tggcggcatc gatttccatc
241 aaaaggcttc tattagaatc ctcagagcca gcctctacta ccatgaactt gcatccaaaa
301 caaaaccaag acgcacgtac ttcttcttct tcttcttcca cctcatcatc aaaatctacg
361 cgtaccaagt ctggagctgc tgctcatgaa gttcctagcg gtccaaaccc tatttcaaac
421 aggtaaataa gttgatatat caatgatgaa gcacagaaaa ctcgtactgc ccttgagagc
481 cggttgttga agatgatagc tagagagttg taacggtgaa gttaattacg agtttgtcat
541 ctttattgtt atcgtttttg tgcaccacta atactgcttg tcctcagtga gagggtctt
601 accttcttgt tatgtcatca atctcagcct tacttctttc tttctttctt tttcgtgct
661 tgtt
```

Fig 15A  CLE42 protein sequence (SEQ. ID. 28)
MRSPHITISLVFLFFLFLIIQTHQRTIDQTHQIGSNVQHVSDMAVTSPEGKRRER
PRVRRPMTTWLKGKMIGANEHGVPSGPNPISNR Fig 15B  CLE42 DNA sequence (SEQ. ID. 29)
ATGAGATCTCCTCACATCACCATTTCACTTGTTTTCTTGTTCTTTCTTTTTCT
AATCATCCAAACCCATCAAAGAACCATTGATCAAACTCACCAGATTGGCT
CCAATGTTCAACATGTCAGTGACATGGCGGTGACTTCGCCTGAAGGGAAA
AGAAGAGAGAGGTTTAGAGTTCGGCGGCCGATGACGACATGGCTGAAGG
GAAAGATGATCGGTGCCAATGAACATGGAGTCCCAAGTGGTCCAAATCCC
ATCTCCAATAGGTAG

GENERATION OF BIOMASS

This application is a U.S. National Stage under 35 U.S.C. § 371 of International Application No. PCT/II32016/051131, filed Mar. 1, 2016, which claims priority to U.S. Provisional Patent Application No. 62/126,965, filed Mar. 2, 2015.

The present invention relates to a method for manipulating the growth and/or structure of a plant. The invention also relates to an expression cassette for use in manipulating the growth and/or structure of a plant, and to a transgenic plant, plant part, plant cell or seed comprising the expression cassette. The present invention also relates to a method of producing a plant derived product, and the plant-derived product per se. The present invention also relates to the use of a vascular tissue specific regulatory element in a method of manipulating the growth and/or structure of a plant. The present invention also relates to a host cell or organism comprising the expression cassette of the present invention.

BACKGROUND

The woody tissue of trees is composed of xylem cells that arise from divisions of stem cells within the cambial meristem. The rate of xylem cell formation is dependent upon the rate of cell division within the cambium and is controlled by both genetic and environmental factors (Miyashima et al (2013) EMBO J. 32, 178-193; Ursache et al (2013) Physiol. Plant. 147, 36-45). In the annual plant *Arabidopsis*, signalling between a peptide ligand CLE41 and a receptor kinase PXY controls cambial cell divisions (Etchells and Turner (2010) Development 137, 767-774; Fisher and Turner (2007) Current Biology 17, 1061-1066; and Hirakawa et al (2008) PNAS, USA 105, 15208-15213).

International patent application number WO2010/029357 relates to methods for altering the growth and/or structure of a plant, in order to maximise its potential as a source of biomass, in particular as a source of feedstock for the paper industry. The patent application describes the overexpression of CLE41, CLE42 and/or PXY in order to achieve the desired increase in the growth and structure of the vascular tissue of the plant.

There is however still a need to be able to improve the manipulation of the growth of plants, in particular trees for example to increase the yield of biomass from trees.

SUMMARY OF THE INVENTION

In a first aspect of the invention, there is provided a method for manipulating the growth and/or structure of a plant comprising modifying the plant to specifically increase the expression and/or activity of PXY and/or CLE in the vascular tissue of the plant compared to the native expression and/or activity of the PXY and/or CLE in the vascular tissue of a wild type plant of the same species maintained under identical conditions.

Modifying the plant preferably comprises specifically increasing the expression and/or activity of PXY and/or CLE in the vascular tissue of the plant, wherein the expression and/or activity of the PXY and/or CLE in non-vascular tissue of the modified plant remains substantially unaltered. In other words, expression and/or activity in the non-vascular tissue of the modified plant may be substantially the same as in the non-vascular tissue of a wild type plant maintained under identical conditions.

CLE may be CLE41 and/or CLE42. Alternatively CLE may be one or more of CLE41, CLE42 and CLE44.

Modifying the plant preferably comprises specifically increasing the expression and/or activity of PXY in the cambium of the plant, such that the expression and/or activity of PXY in non-cambium tissue (including the phloem and xylem) of the modified plant remains substantially unaltered. In other words, expression and/or activity in the non-cambium tissue of the modified plant may be substantially the same as in the non-cambium tissue of a wild type plant of the same species maintained under identical conditions.

Modifying the plant preferably comprises specifically increasing the expression and/or activity of CLE in the vascular tissue of the plant, such that the expression and/or activity of CLE in non-vascular tissue of the modified plant remains substantially unaltered. In other words, expression and/or activity of CLE in the non-vascular tissue of the modified plant may be substantially the same as in the non-vascular tissue of a wild type plant of the same species maintained under identical conditions.

Modifying the plant preferably comprises specifically increasing the expression and/or activity of CLE in the phloem of the plant, such that the expression and/or activity of CLE in non-phloem tissue (including the cambium and xylem) of the modified plant remains substantially unaltered. In other words, expression and/or activity in the non-phloem tissue of the modified plant may be substantially the same as in the non-phloem tissue of a wild type plant of the same species maintained under identical conditions.

Modifying the plant to specifically increase vascular tissue specific expression and/or activity may comprise introducing into the plant a regulatory element which specifically directs expression of PXY in the vascular tissue of the plant, more preferably in the cambium of the plant.

Modifying the plant to specifically increase vascular tissue specific expression and/or activity may comprise introducing into the plant a regulatory element which specifically directs expression of CLE in the vascular tissue of the plant, more preferably in the phloem of the plant.

A method of manipulating the growth and/or structure of a plant, as defined herein, may comprise modifying the plant to specifically increase the expression and/or activity of PXY and CLE in the vascular tissue of the plant compared to the expression and/or activity of PXY and CLE in the vascular tissue of a wild type plant of the same species maintained under identical conditions. The expression and/or activity of both PXY and CLE is increased compared to native expression in the wild type plant.

Thus, the method of manipulating the growth and/or structure of a plant as defined herein may comprise: i) modifying the plant to specifically increase the expression and/or activity of PXY in the cambium of a plant compared to the expression and/or activity of PXY in the vascular tissue of a wild type plant of the same species maintained under identical conditions; and ii) modifying the plant to specifically increase the expression and/or activity of CLE in the phloem of the plant compared to the expression and/or activity of CLE in the vascular tissue of a wild type plant of the same species maintained under identical conditions.

The method of modifying the plant may comprise directing expression and/or activity of PXY to the vascular tissue of a plant by placing PXY under the control of a vascular-tissue specific promoter. The promoter may be phloem, xylem or cambium specific. Preferably, the promoter is cambium specific. The promoter may be the promoter of the plant ANTEGUMENTA (herein referred to as "ANT") gene, or a functional fragment or variant thereof. The ANT promoter may preferably be derived from hybrid Aspen (PttANT).

The method of modifying the plant may comprise directing expression and/or activity of CLE to the vascular tissue of a plant by placing CLE under the control of a vascular-tissue specific promoter. The promoter may be phloem, xylem or cambium specific. Preferably, the promoter may be phloem specific. The promoter may be the promoter of the phloem specific lectin gene PHLOEM PROTEIN 2 (herein referred to as "PP2"), or a functional fragment or variant thereof. The PP2 promoter may preferably be derived from hybrid Aspen (PttPP2).

In a second aspect, the present invention also provides a method for increasing the growth rate of a plant, the method comprising manipulating the growth and/or structure of the plant as described herein.

In a third aspect, the present invention also provides a method for increasing the radial growth of a plant, the method comprising manipulating the growth and/or structure of the plant as described herein.

In a fourth aspect, the present invention also provides a method for increasing the amount of leaf tissue in a plant, the method comprising manipulating the growth and/or structure of the plant as described herein.

In a fifth aspect, the present invention provides a method for increasing the biomass of a plant, the method comprising manipulating the growth and/or structure of the plant as described herein.

In a sixth aspect, the present invention provides a method of producing a plant derived product; comprising manipulating the growth and/or structure of the plant as described herein, and harvesting a plant product from the plant.

In a seventh aspect, the present invention provides an expression cassette comprising a nucleic acid sequence encoding a regulatory element which specifically directs expression in the vascular tissue of a plant. The regulatory element may specifically direct expression in the phloem, xylem or cambium. Preferably, the regulatory element will specifically direct expression in the cambium. The regulatory element may be the promoter of the ANT gene, or a functional fragment or variant thereof. The regulatory element may be the promoter of the PP2 gene, or a functional fragment or variant thereof. A regulatory element of the expression cassette may be operably linked to a gene, such as PXY and/or CLE. An expression cassette may comprise a first regulatory element operably linked to a nucleic acid molecule encoding PXY, and a second regulatory element operably linked to a nucleic acid molecule encoding CLE.

In an eighth aspect, the present invention provides a transgenic plant cell comprising an expression cassette as defined herein. Thus, the plant cell is manipulated according to the method of the first aspect.

In a ninth aspect, the present invention provides a transgenic plant, plant part or transgenic seed comprising a plant cell as defined above. Thus, the plant, plant part or transgenic seed is manipulated according to the method of the first aspect.

In a tenth aspect, the present invention provides a plant derived product produced according to a method of the sixth aspect.

In an eleventh aspect, the present invention provides the use of a vascular tissue specific regulatory element, for use in the manipulation of the growth and/or structure of a plant. A regulatory element may be, for example a promoter of the ANT gene or a functional fragment or variant thereof, and/or a promoter of the PP2 gene or a functional fragment or variant thereof. A regulatory element may be provided in an expression cassette according to the seventh aspect of the invention. Preferably, the use is according to a method of any one of the first to sixth aspects of the invention.

In a twelfth aspect the present invention provides a host cell or organism comprising an expression construct according to the seventh aspect.

BRIEF DESCRIPTION OF THE DRAWINGS

The invention will be described further, by way of example, with reference to the accompanying drawings, in which:

FIG. 13(A) shows an alignment of PXY with similar genes from *Arabidopsis* (PXL1 and PXL2), together with homologous genes from Rice (Os02g02140.1 and Os03g05140.1) and Poplar (PttPXY). The consensus sequence of PXY is also shown; (B) shows the amino acid sequence of PttPXY and the nucleic acid which encodes the protein; (C) shows the nucleic acid sequence encoding *Arabidopsis* PXY.

FIG. 14A shows an alignment of CLE41 and CLE42 and homologous sequences from other plant species, including the CLE41 consensus sequence; (B) shows *Arabidopsis* amino acid and nucleic acid sequence; (C) shows the nucleic acid sequence of PttCLE41.

FIG. 15 shows the amino acid sequence of the CLE42 proteins (A) and nucleotide sequence of the CLE42 gene (B).

DETAILED DESCRIPTION

Figure 1:
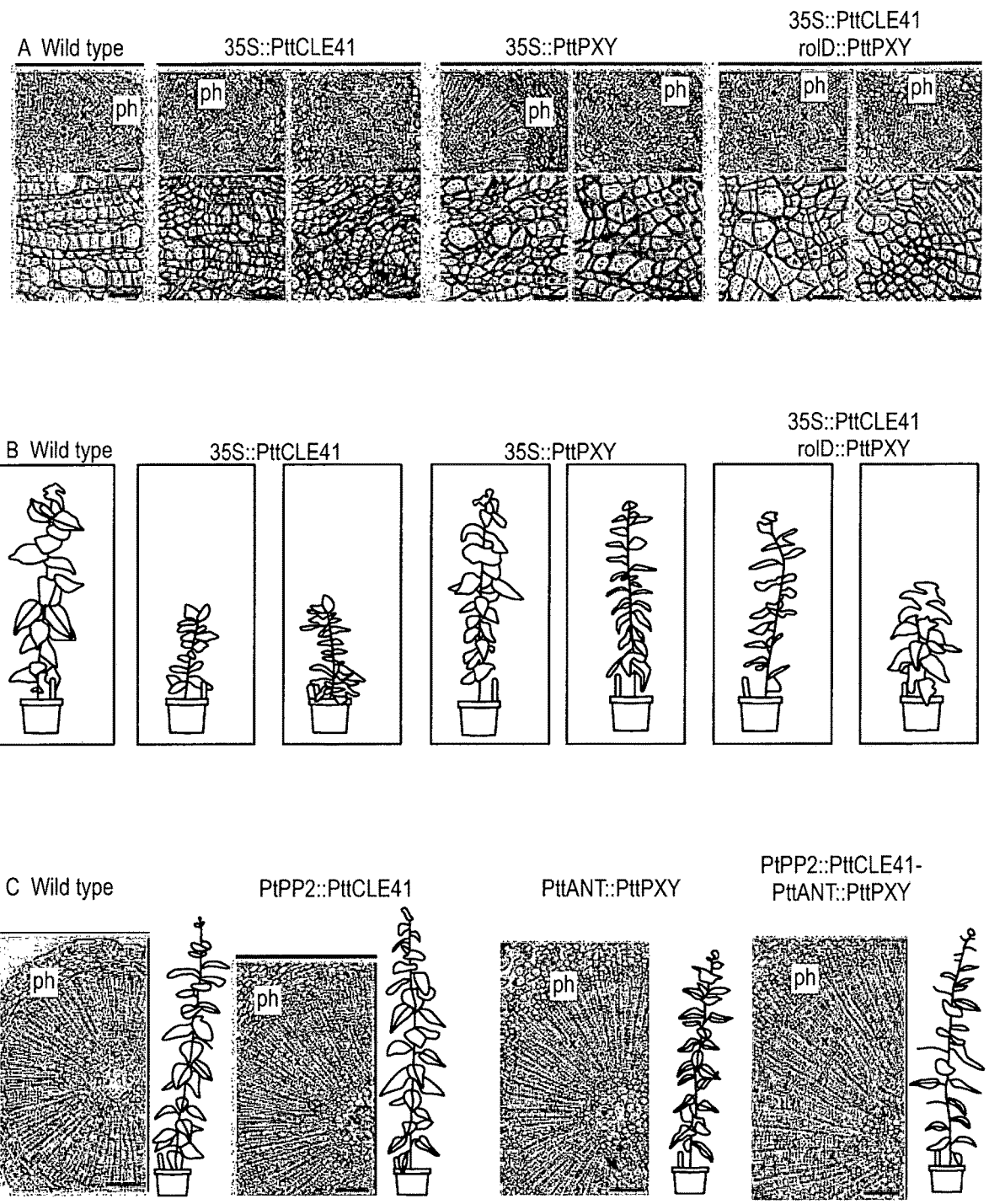
FIG. 1 shows the phenotypes of hybrid aspen ectopically overexpressing PttCLE41 and/or PttPXY genes. (A): Sections from tissue culture grown plantlets 3 weeks post rooting. Where two images are shown in the upper panel, they were selected to show the range of phenotypes observed. Scale bars indicate 200 μM (upper panels) and 50 μM (lower panels). The xylem (x) and phloem (ph) are indicated. Asterisks show examples of organised files of cells. (B): Representative greenhouse grown plants 3 months after transfer to soil. (C): Phenotypes of hybrid aspen with targeted overexpression of PttCLE41 and PttPXY. Left hand panels show sections from tissue culture grown plantlets 3 weeks post rooting while greenhouse grown plants 3 months after transfer to soil are shown on the right. Scale bars indicate 200 μM. The xylem (x) and phloem (ph) are also indicated. Arrows highlight the disrupted xylem.

The present inventors have shown that PttPXY and its peptide ligand PttCLE41 are functional orthologues and act to control a multifunctional pathway that regulates both the rate of cambial cell division and woody tissue organization in trees. The present invention is based upon the finding that vascular tissue-specific overexpression of PXY generated plants that exhibited an increase in the rate of wood formation, were taller and possessed larger leaves compared to wild type control plants. The results demonstrate that the PXY-CLE pathway has evolved to regulate secondary growth and manipulating this pathway can result in dramatically increased tree growth and productivity.

Definitions

As used herein, the term "nucleic acid molecule" includes DNA molecules (e.g., a cDNA or genomic DNA) and RNA molecules (e.g., a mRNA) and analogs of the DNA or RNA generated, e.g., by the use of nucleotide analogs. A nucleic acid molecule may be single-stranded or double-stranded, but preferably is double-stranded DNA. The nucleic acid molecule may be recombinant.

A "naturally-occurring" nucleic acid molecule refers to an RNA or DNA molecule having a nucleotide sequence that occurs in nature (e.g., encodes a natural protein). A naturally occurring nucleic acid molecule may also be referred to as native.

The terms protein and polypeptide refers to a polymeric form of amino acids of any length, which can include coded and non-coded amino acids, chemically or biochemically modified or derivatized amino acids, and polypeptides having modified peptide backbones. The terms protein and polypeptide may be used interchangeably herein.

"Foreign" referring to a nucleic acid molecule or polypeptide, with respect to a plant is used to indicate that the nucleic acid sequence or polypeptide is not naturally found in that plant, or is not naturally found in that genetic locus in that plant.

With regards to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5'- and/or 3'-ends of the nucleic acid) in the genomic DNA of the organism from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

By the term "recombinant nucleic acid molecule" is meant a nucleic acid molecule that has a sequence that is not naturally occurring or has a sequence that is made by an artificial combination of two otherwise separated segments of sequence. This artificial combination may be accomplished by chemical synthesis or by the artificial manipulation of nucleic acid molecules, e.g., by genetic engineering techniques, such as by the manipulation of at least one nucleic acid by a restriction enzyme, ligase, recombinase, and/or a polymerase.

As used herein, the terms "gene" and "recombinant gene" refer to nucleic acid molecules which include an open reading frame encoding protein, and can further include non-coding regulatory sequences and introns.

The term "complement of a nucleic acid sequence" is the nucleotide sequence which would be capable of forming a double stranded DNA molecule with the represented nucleotide sequence, and which can be derived from the represented nucleotide sequence by replacing the nucleotides by their complementary nucleotide according to Chargaff's rules (A< >T; G< >C) and reading in the 5' to 3' direction, i.e., in opposite direction of the represented nucleotide sequence.

A "regulatory element" is a non-coding region of a gene which regulates its transcription.

An "expression cassette" is a genetic vehicle comprising a regulatory element for expression of a gene or coding sequence, and optionally a coding sequence operably linked thereto. An expression cassette may facilitate expression of a gene in a cell into which it is introduced.

"Operably linked" means joined as part of the same nucleic acid molecule, suitably positioned and oriented for transcription to be initiated from the promoter. DNA operably linked to a promoter is "under transcriptional initiation regulation" of the promoter.

A cell into which a foreign nucleic acid molecule has been introduced may be referred to herein as a recombinant cell, or a transgenic or transformed cell. Introduction may be defined as the insertion of a nucleic acid molecule into a cell. Once introduced into a host cell, a recombinant nucleic acid is replicated by the host cell, however, the recombinant nucleic acid once replicated in the cell remains a recombinant nucleic acid for purposes of this invention.

By "recombinant protein" herein is meant a protein produced by a method employing a recombinant nucleic acid. The term protein may be used interchangeably with the term polypeptide. As outlined above "recombinant nucleic acid molecules" and "recombinant proteins" also are "isolated" as described above. The cell into which the recombinant nucleic acid molecule may be introduced may be described as a recombinant cell, or a transformed or transgenic cell.

A transgenic plant, plant part or seed may comprise one or more transgenic plant cells, i.e. cells which comprise recombinant genetic material which is not normally found in a plant or tree of this type and which has been introduced into the plant in question (or into progenitors of the plant) by human manipulation.

Herein, "expression" refers to the biosynthesis of a gene product, i.e. in the case of a structural gene such as PXY or CLE, expression involves the transcription of the structural gene into mRNA and the translation of mRNA into one or more polypeptides.

"Increased expression" means an increase in the level of transcription and translation compared to the level for the same gene in a wild type plant of the same species maintained under identical conditions.

"Activity" refers to a phenotypic property of the protein, for example its ability to bind to a binding partner, its ability to generate a signal within the pathway, and mediate downstream effects on growth and development.

Included within the scope of the present invention are functional equivalents of the polypeptides and nucleic acid molecules defined herein. The term "functional equivalent" is intended to include fragments, mutants, hybrids, variants, analogs, or chemical derivatives of a nucleic acid molecule or protein as defined herein, which shares at least one structural characteristic of the native nucleic acid molecule or functional characteristic of the protein.

A functional fragment of a nucleic acid molecule or polypeptide as defined herein may include any portion of an amino acid or nucleic acid sequence which shares at least one functional or structural characteristic that is substantially similar to the subject polypeptide or nucleic acid molecule. A structural or functional characteristic may include binding characteristics, the ability to regulate a downstream signalling pathway, to mediate one or more phenotypic effects, of the native nucleic or polypeptide.

As used herein, the term "hybridizes under stringent conditions" describes conditions for hybridization and washing. Stringent conditions are known to those skilled in the art and can be found in available references (e.g., Current Protocols in Molecular Biology, John Wiley & Sons, N.Y., 1989, 6.3.1-6.3.6). Aqueous and non-aqueous methods are described in that reference and either can be used.

Sequence identity (e.g., percent homology) can be determined using any homology comparison software, including for example, the BlastN software of the National Center of Biotechnology Information (NCBI) such as by using default parameters.

A variant of a polypeptide or protein defined herein may be one which is altered by one or more amino acids. The variant may have "conservative" changes, wherein a substituted amino acid has similar structural or chemical properties, e.g., replacement of leucine with isoleucine. More rarely, a variant may have "non-conservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art, for example, DNASTAR© software. A functional variant of a polypeptide defined herein will preferably retain at least one structural or functional characteristic of the non-variant polypeptide.

By "vascular tissue" is meant the conductive and supportive tissue in a plant.

By "specifically" or "specific expression or activity" is meant that the nucleic acid molecule is preferentially expressed, or the protein is preferentially active, in one cell type, tissue, or developmental than another.

Herein, the "growth" of a plant refers to the size of a plant, preferably the secondary growth, and preferably the amount of vascular and/or interfasicular tissue, more preferably the amount of xylem cells, also referred to as the woody tissue or biomass of a plant.

"Radial diameter" is a measure of the circumference of a plant, and indicative of growth and division of vascular tissue.

"Biomass" refers to the amount of tissue produced by a plant, for example in one growing season. The "leaf tissue" is the quantity of leaves, expressed in weight.

"Vigour" refers to the amount, by weight, of tissue produced by a plant in a given time.

"Growth rate" is a measure the amount of growth, for example weight or radial growth, in a specified time period.

"Seed yield" is the amount of seeds, for example by weight, harvested from a plant, for example in a given growing season.

The "structure" of a plant refers to the organisation of tissue in a plant, preferably the vascular tissue, most preferably the polarity of the phloem and xylem cells.

By "identical conditions" is meant conditions which are the substantially the same in terms of temperature, light, and availability of nutrients and water. By substantially is meant that the conditions may vary slightly, but not to an extent to which is known to affect the growth of a plant. The term "identical conditions" also encompasses comparing plants of the same species, of the same pre-selected developmental stage.

PXY

Herein, PXY refers to a receptor-like kinase which in nature binds to CLE41 or CLE42. Preferably, the term PXY refers to a receptor like kinase which comprises an extracellular domain comprising leucine rich repeats (LRR). Upon binding by CLE41 and/or CLE42 it mediates the activation of a signalling pathway which results in division of undifferentiated cambial cells. Herein, preferably the term PXY refers to a member of the XI family of *Arabidopsis thaliana* RLK proteins. PXY is also known in the art as TDR.

Figure 13A:
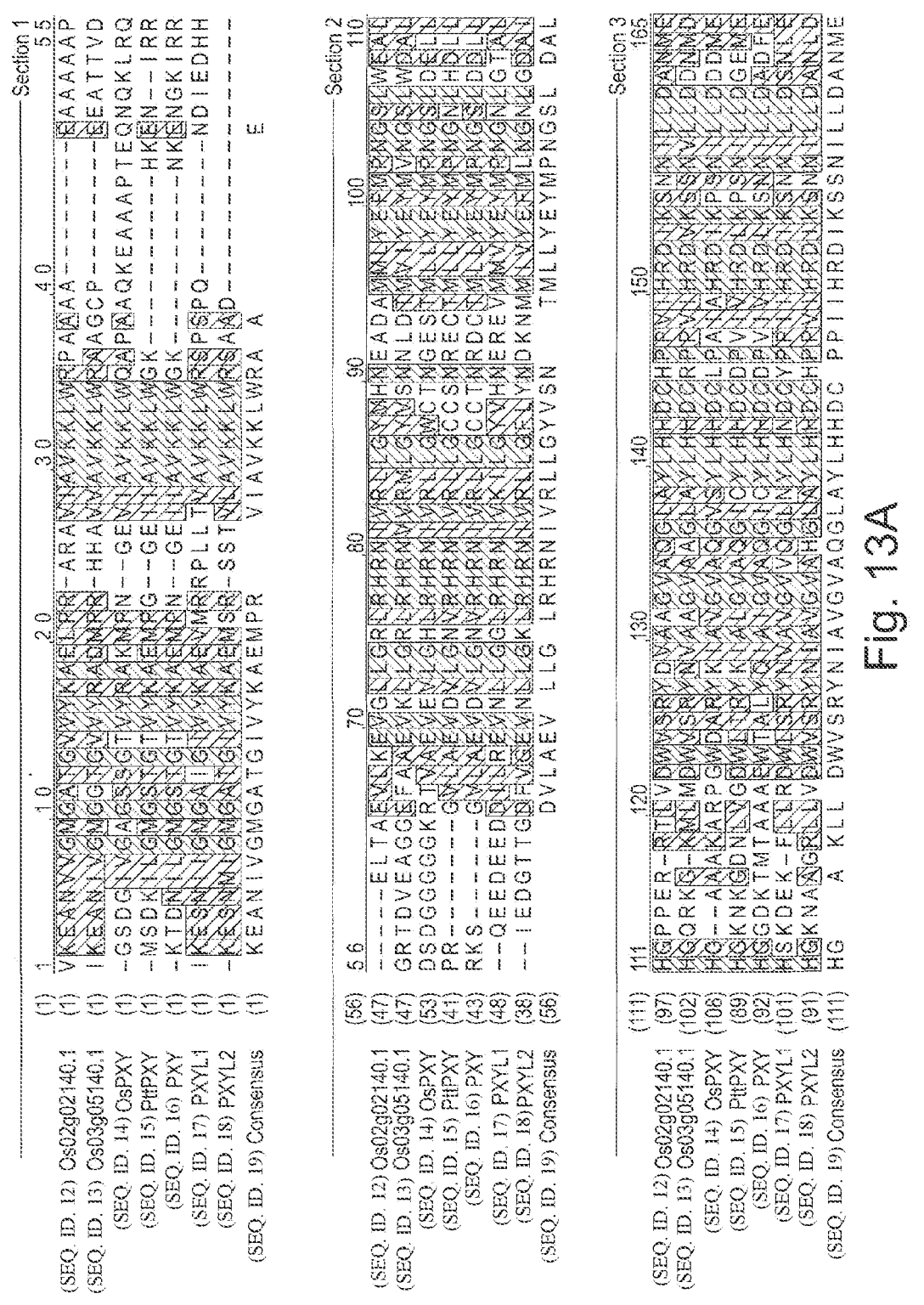

Herein, a PXY polypeptide includes i) a polypeptide comprising a conserved region in the kinase domain wherein the conserved region comprises the consensus sequence of FIG. 13A, and is capable of binding CLE41 and/or CLE42 and mediating the activation of a signalling pathway which results in division of undifferentiated cambial cells; ii) a polypeptide having an amino acid sequence as shown in FIG. 5A, 13B, 13C. Alternatively, a PXY polypeptide as defined herein may be a functional orthologue of such a polypeptide, derived from another plant, such as a woody plant. Such orthologues will preferably be capable of binding to CLE41 or CLE42 and mediating the activation of a signalling pathway which results in division of undifferentiated cambial cells. Such orthologues will preferably comprise the PXY polypeptide consensus sequence of FIG. 13A.

References herein to PXY include functional equivalents of the polypeptide. Equivalents include fragments and variants (including orthologues) of a PXY polypeptide as described herein. A functional equivalent of PXY for use in the present invention will have some or all of the desired biological activity of the native polypeptide, preferably the ability to bind to CLE41 and/or CLE42 and regulate growth and/or differentiation of the vascular tissue. Functional equivalents may exhibit altered binding characteristics to CLE41 and/or CLE42 compared to a native PXY polypeptide. Preferred functional equivalents may show reduced non-desirable biological activity compared to the native protein. A functional equivalent will preferably comprise at least 70% sequence identity to a PXY polypeptide of FIG. 5A, 13B, or 13C, more preferably at least 75%, 80%, 82%, 84%, 85%, 86%, 87%, 88%, 89%, 90%, 91%, 92%, 93%, 94%, 95%, 96%, 97%, 98%, 99%, or 100% sequence identity with a PXY polypeptide of FIG. 5A, 13B, or 13C. A functional equivalent will preferably comprise a sequence having at least 85%, 90%, 95%, 96%, 97%, 98%, 99% or 100% sequence identity with the PXY consensus sequence of FIG. 13A.

A functional fragment of a PXY polypeptide is a portion of a polypeptide sequence or variant thereof as defined herein. A functional fragment preferably retains some or all of the biological activity of the full length PXY polypeptide. Preferably, a functional fragment of PXY retains the ability to bind CLE41 or CLE42 and regulate the growth and/or differentiation of the vascular tissue of a plant. Preferably, a fragment will comprise at least a portion of the kinase domain, preferably a biologically active portion thereof, up to the full length kinase domain. Most preferably, a fragment will further comprise at least a portion of the extracellular domain, and will preferably comprise at least a portion of the LLR region. A fragment may be 40%, 50%, 60%, 70%, 80%, 90%, or 95% of the length of the full length PXY polypeptide.

A nucleic acid encoding PXY may comprise a sequence which encodes a polypeptide of FIG. 5A. A nucleic acid sequence encoding PXY may be as shown in FIG. 13B or FIG. 13C. Nucleic acid sequences encoding PXY are available from Genbank, under references PXY=At5g61480 (TAIR), PXL1=At1g08590 (TAIR), and PXL2=At4g28650 (TAIR); and Genbank Accession No. KP682331 version 1 (PttPXY).

Also included are functional equivalents of the nucleic acid molecules defined herein, which encode a polypeptide or a functional equivalent thereof as defined herein. A functional equivalent may be a sequence variant and/or a functional fragment of a PXY nucleic acid sequence as defined herein. A variant will preferably encode a polypeptide which has the ability to bind CLE41 or CLE42 and regulate the growth and/or differentiation of the vascular tissue of a plant, and preferably shares at least 70%, 75%, 80%, 82%, 84%, 85%, 86%, 87%, 88%, 89%, 90%, 91%, 92%, 93%, 94%, 95%, 96%, 97%, 98%, 99%, sequence identity with a nucleic acid sequence of FIG. 13B or 13C, or encodes a polypeptide having at least 70%, 75%, 80%, 82%, 84%, 85%, 86%, 87%, 88%, 89%, 90%, 91%, 92%, 93%, 94%, 95%, 96%, 97%, 98%, 99%, sequence identity with a polypeptide of FIG. 5A or 13B or FIG. 13C, or encodes a polypeptide comprising a consensus sequence of FIG. 13A. Alternatively, a variant may be defined as a sequence which hybridises under stringent conditions to a complement of the nucleic acid sequence of FIG. 13B or 13C. A fragment may encode a functional fragment of a PXY polypeptide as defined above. A fragment of a nucleic acid molecule may be 40%, 50%, 60%, 70%, 80%, 90%, or 95% of the length of the full length PXY nucleic acid sequence of FIG. 13B or 13C.

CLE

Herein, CLE refers to a ligand which is able to activate a kinase receptor, and result in phosphorylation of itself or its target. Preferably, the term CLE refers to a signalling protein, preferably of less than 15 kDa in mass, and preferably comprising a hydrophobic region at the amino terminus. Upon binding to PXY it mediates the activation of a signalling pathway which results in division of undifferentiated cambial cells. The term CLE includes CLE41, CLE42 and CLE44, and the aspects of the invention may relate to increased expression and/or activity of CLE41, CLE42 or CLE44. CLE41 is also known in the art as TDIF.

Herein, a CLE41 or CLE42 polypeptide includes i) a polypeptide comprising a conserved region in the kinase domain having the sequence comprising the consensus sequence of FIG. 14A, and being capable of binding PXY to mediate the activation of a signalling pathway which results in division of undifferentiated cambial cells; ii) a polypeptide having an amino acid sequence as shown in FIG. 5B, 14B or 14C, or 15A. Alternatively, a CLE41 or CLE 42 polypeptide as defined herein may be a functional orthologue of such a polypeptide, derived from another plant, such as a woody plant. Such orthologues will preferably be capable of binding to PXY and mediating the activation of a signalling pathway which results in division of undifferentiated cambial cells. Such orthologues will preferably comprise the CLE polypeptide consensus sequence of FIG. 14A.

References herein to CLE41, CLE42 and CLE44 include functional equivalents of the polypeptides. Equivalents include fragments and variants (including orthologues) of a CLE41 or CLE42 polypeptide as described herein. A functional equivalent of CLE for use in the present invention will have some or all of the desired biological activity of the native polypeptide, preferably the ability to bind to PXY and regulate growth and/or differentiation of the vascular tissue. Functional equivalents may exhibit altered binding characteristics to PXY compared to a native CLE polypeptide. Preferred functional equivalents may show reduced non-desirable biological activity compared to the native protein. A functional equivalent will preferably comprise at least 70% sequence identity to a CLE41 polypeptide of FIG. 5B, FIG. 14B or FIG. 14C, more preferably at least 75%, 80%, 82%, 84%, 85%, 86%, 87%, 88%, 89%, 90%, 91%, 92%, 93%, 94%, 95%, 96%, 97%, 98%, 99%, or 100% sequence identity with a CLE41 polypeptide of FIG. 5B, FIG. 14B or FIG. 14C. A functional equivalent will preferably comprise a sequence having at least 85%, 90%, 95%, 96%, 97%, 98%, 99% or 100% sequence identity with the CLE41 consensus sequence of FIG. 14A. A functional equivalent will preferably comprise at least 70% sequence identity to a CLE42 polypeptide of FIG. 14A, FIG. 14B or FIG. 15A, more preferably at least 75%, 80%, 82%, 84%, 85%, 86%, 87%, 88%, 89%, 90%, 91%, 92%, 93%, 94%, 95%, 96%, 97%, 98%, 99%, or 100% sequence identity with a CLE42 polypeptide of 14A, FIG. 14B or FIG. 15A. A functional equivalent will preferably comprise a sequence having at least 85%, 90%, 95%, 96%, 97%, 98%, 99% or 100% sequence identity with the CLE42 consensus sequence of FIG. 14A.

A functional fragment of a CLE polypeptide is a portion of a CLE41 or CLE42 polypeptide sequence or a variant thereof as defined herein. A functional fragment preferably which retains some or all of the biological activity of the full length CLE polypeptide. Preferably, a functional fragment of CLE retains the ability to bind PXY and regulate the growth and/or differentiation of the vascular tissue of a plant. A fragment may be 40%, 50%, 60%, 70%, 80%, 90%, or 95% of the length of the full length CLE41 or CLE42 polypeptide. Preferably, a fragment may be at least 7 amino acids in length, preferably at least 8, 9, or 10, 15, 20, 25, 30, 40, 50, 60, 70, 80, 90 or 100 amino acids in length, up to the full length CLE41 or CLE42 polypeptide. Most preferably, a fragment will comprise the conserved region consisting of amino acids 124 to 137 of the consensus sequence of FIG. 14A.

A nucleic acid encoding CLE41 may comprise a sequence which encodes a polypeptide of FIG. 5B, FIG. 14B or FIG. 14C. A nucleic acid sequence encoding CLE41 may be as shown in FIG. 14B or 14C. The nucleic acid and amino acid sequence of PttCLE41 are available under Genbank Accession No. KP682332, version 1.

A nucleic acid encoding CLE42 may comprise a sequence which encodes a polypeptide of FIG. 5B or FIG. 15A. A nucleic acid sequence encoding CLE42 may be as shown in FIG. 15B.

Also included are functional equivalents of the nucleic acid sequences defined herein, which encode a polypeptide as defined herein or an orthologues and functional equivalents of the above mentioned polypeptides, as defined herein. A functional equivalent may be a sequence variant and/or a functional fragment of a CLE41 or CLE42 nucleic acid sequence as defined herein. A variant will preferably encode a CLE41 or CLE42 polypeptide or functional equivalent thereof which has the ability to bind PXY and regulate the growth and/or differentiation of the vascular tissue of a plant, and preferably shares at least 70%, 75%, 80%, 82%, 84%, 85%, 86%, 87%, 88%, 89%, 90%, 91%, 92%, 93%, 94%, 95%, 96%, 97%, 98%, 99%, sequence identity with a nucleic acid sequence of FIG. 14B or 14C, or 15B. Alternatively, a variant may be defined as a sequence which hybridises under stringent conditions to a complement of the nucleic acid sequence of FIG. 14B or 14C, or 15B. A fragment may encode a functional fragment of a CLE41 or CLE42 polypeptide as defined above. A fragment of a nucleic acid molecule may be 40%, 50%, 60%, 70%, 80%, 90%, or 95% of the length of the full length CLE41 or CLE42 nucleic acid sequence. A fragment of a nucleic acid molecules encoding CLE41 or CLE42 will preferably comprise at least 21 nucleotides in length, more preferably at least 24, 27, 30 or 33 nucleotides, up to the total number of nucleotide residues in a full length sequence of FIG. 14B or 14C, or 15B.

Functional Equivalents

A variant of a nucleic acid molecule as defined herein may include a sequence which hybridises under stringent conditions to a complement of the reference sequence, or a sequence which has a specified degree of sequence identity with the reference sequence. Two nucleic acid or amino acid sequences are orthologs of each other if they share a common ancestral sequence and diverged when a species carrying that ancestral sequence split into two species, sub-species, or cultivars. Orthologous sequences are also homologous sequences. Orthologous sequences hybridize to one another under high-stringency conditions.

A preferred example of high stringent hybridization conditions are hybridization in 6× sodium chloride/sodium citrate (SSC) at about 45° C., followed by one or more washes in 0.2×SSC, 0.1% (w/v) SDS at 50° C. Another example of stringent hybridization conditions are hybridization in 6×SSC at about 45° C., followed by one or more washes in 0.2×SSC, 0.1% (w/v) SDS at 55° C. A further example of stringent hybridization conditions are hybridization in 6×SSC at about 45° C., followed by one or more washes in 0.2×SSC, 0.1% (w/v) SDS at 60° C. Preferably, stringent hybridization conditions are hybridization in 6×SSC at about 45° C., followed by one or more washes in 0.2×SSC, 0.1% (w/v) SDS at 65° C. Particularly preferred stringency conditions (and the conditions that should be used if the practitioner is uncertain about what conditions should be applied to determine if a molecule is within a hybridization limitation of the invention) are 0.5 molar sodium phosphate, 7% (w/v) SDS at 65° C., followed by one or more washes at 0.2×SSC, 1% (w/v) SDS at 65° C.

Sequence identity may be determined as defined herein, across a pre-defined window of comparison. A comparison window may be 20%, 30%, 40%, 50%, 60%, 70%, 80%, 90% or 100% of the full length reference sequence.

Manipulating Plant Growth/Structure

By "manipulate" is meant altering the native growth pattern of a plant, such that a plant manipulated according to an aspect of the present invention will exhibit an altered growth pattern and/or structure compared to a wild type (non-manipulated) plant of the same species, maintained under identical conditions. The manipulation is preferably effected by a method of the first aspect as defined herein.

The manipulation preferably includes increasing the expression and/or activity of PXY and/or CLE in a plant.

Increased expression will generally result in an increased amount of the protein in a cell or tissue compared to the amount in a corresponding cell or tissue in a wild type plant of the same species maintained under identical conditions. Increased expression may be determined either by measuring the relative amounts of the gene product in a cell or tissue extracted from the modified plant and comparing it to the level in a corresponding cell or tissue from a wild type plant using techniques available in the art such as activity assays, Western blots using antibodies capable of specifically binding the polypeptide, Enzyme-Linked ImmunoSorbent Assay (ELISA), radio-immuno-assays (RIA), immunohistochemistry, immunocytochemistry, immunofluorescence, Northern blot analysis, reverse transcription polymerase chain reaction (RT-PCR) analysis (including quantitative, semi-quantitative or real-time RT-PCR) and RNA-in situ hybridization. Increased expression may also be determined by measuring the phenotypic effects of the protein, and determining whether there is an increase in a phenotypic effect compared to the corresponding phenotype in a wild type plant maintained under identical conditions.

Increased protein activity may be determined herein by measuring the phenotypic effects on the modified plant and comparing the phenotypic effects to the same phenotypes of a wild type plant maintained under identical conditions. A statistically significant improvement in a phenotypic effect in the modified plant compared to the wild type plant is indicative of an increase in the expression and/or activity of the protein.

It is envisaged that where a plant naturally expresses PXY or CLE, their modulation may be achieved by altering the expression pattern of the native gene(s) and/or production of the polypeptide. This may be achieved by any suitable method, including altering transcription of the gene, and/or translation of the mRNA into polypeptide, and post-translational modification of the polypeptide.

Tissue specific expression or activity means that the nucleic acid molecule is preferentially expressed in a particular tissue compared to another tissue of the same plant, or the protein is preferentially active in one tissue compared to another. Specific expression may be achieved using a specific regulatory element to control expression of the nucleic acid molecule.

Altering the expression pattern of a native gene may be achieved by placing it under control of a heterologous regulatory sequence, which is capable of directing the desired expression pattern of the native gene as defined herein. Suitable regulatory sequences are described herein.

Alternatively, regulation of expression of the native gene may be altered through changing the pattern of transcription factors which mediate expression of the gene. This may require the use of modified transcription factors, whose binding pattern is altered to obtain a desired expression pattern of the gene.

Alternatively, the copy number of the native gene may be increased or decreased, in order to change the amount of expression of the gene, for example by introducing into a plant cell an expression cassette comprising the gene. The gene may be under control of a suitable regulatory element to achieve the desired tissue specific expression, as described herein. Suitable methods for carrying out these embodiments of the invention are known to persons skilled in the art, and may employ the use of an expression construct according to the invention.

In addition, modulating the activity mediated by CLE and/or PXY may be achieved by altering their binding pattern, in order to up regulate the downstream signalling pathway. The binding pattern may be altered in any suitable way, for example by altering the structure, binding affinity, temporal binding pattern, selectivity and amount available for binding on the cell surface of CLE and/or a PXY. A binding pattern may be altered by making appropriate variations to the ligand polypeptide, for example to change its binding site to the receptor, using known methods for mutagenesis. Alternatively, non-protein analogues may be used. Methods for manipulating a polypeptide used in the present invention are known in the art, and include for example altering the nucleic acid sequence encoding the polypeptide. Methods for mutagenesis are well known. Preferably, where variants are produced using mutagenesis of the nucleic acid coding sequence, this is done in a manner which does not affect the reading frame of the sequence and which does not affect the polypeptide in a manner which affects the desired biological activity.

In selecting suitable variants for use in the present invention, routine assays may be used to screen for those which have the desired properties. This may be done by visual observation of plants and plant material, or measuring the biomass of the plant or plant material.

The manipulation may be stable or transient.

Over expression of PXY and/or CLE in the vascular tissue of a plant may be used to increase the number of cells in the vascular tissue of a plant, but without increasing the actual biomass of the plant (i.e. the number of cells may be increased, but the size of these cells is smaller). This has the effect of increasing the density of the vascular tissue, and therefore producing a harder wood. Thus, the invention includes methods for the production of a wood product having a particular density, comprising the steps of the first aspect as defined herein. In addition, it is envisaged that by manipulating plant cells to differentiate their vascular tissue, and therefore grow, environmental growth signals may be bypassed and the present invention may be used to extend the growth season of plants, beyond that which would be possible in a native plant.

Regulatory Elements

A regulatory element controls expression of a gene to which is operably linked, for example the spatial and/or temporal expression.

Regulatory elements include, without limitation, promoters, 5' and 3' UTR's, enhancers, transcription factor or protein binding sequences, start sites and termination sequences, ribozyme binding sites, recombination sites, polyadenylation sequences, and sense or antisense sequences. As used herein, the term "promoter" refers to a region of DNA which lies upstream of the transcriptional initiation site of a gene to which RNA polymerase binds to initiate transcription of RNA. A regulatory element may be DNA, RNA or protein. Preferably, a regulatory element is a nucleic acid sequence which is capable of directing tissue specific expression of a coding sequence to which it is operably linked.

A regulatory element is therefore preferably tissue specific, vascular tissue specific. It may be specific for directing expression in the cambium, xylem and/or phloem tissue of a plant. Preferred regulatory elements are cambium or phloem specific.

A tissue specific regulatory element need not direct expression exclusively in the relevant tissue, but may direct expression in non-vascular tissue (or non-cambium or non-phloem) tissue, but may direct limited or absent expression or activity in the non-vascular (e.g. non-cambium or non-phloem) tissue.

A regulatory element may preferably be plant derived, in order to provide the desired tissue specificity. Preferably, a regulatory element may be derived from the same species of plant as the plant being modulated. However, it is envisaged that non-plant regulatory sequences may be suitable for use in the invention where they are capable of providing tissue specific expression, for example when used in conjunction with another tissue specific regulatory element. Such promoters include viral, fungal, bacterial, animal and plant-derived promoters capable of functioning in plant cells.

A regulatory element may be inducible and may direct expression in response to environmental or developmental cues, such as temperature, chemicals, drought, and others. It may be developmental stage specific. A regulatory element may be constitutive, whereby it directs expression under most environmental or developmental conditions. In a preferred aspect, the promoter is an inducible promoter or a developmentally regulated promoter.

Phloem specific promoters include SUC2, APL, KAN1, KAN2, At4g33660, At3g61380, and At1g79380, and PP2. Preferably, the promoter is a sequence present in the upstream region of the PP2 gene of *Populus trichocarpa*, preferably within 1999 bp upstream of the start codon of the PP2 gene. The promoter may be obtained using primers:

```
(pPtPP2-F
                                      (SEQ. ID. 20)
atccctaggcctgcaggTAAGCTATGTACGTTTTGG
and pPttANT-R
                                      (SEQ. ID. 21)
atcactagtGACAAGCTGAGAGACTG).
```

Xylem specific promoters include REV, IRX1 COBL4, KOR, At2g38080, and At1g2744.

Cambium tissue specific promoters include ANT. Preferably, the promoter is a sequence present in the upstream region of the ANT gene of hybrid aspen from 1156 bp upstream of the start codon to 906 bp upstream of the start codon. The promoter may be obtained using primers primers:

```
pPttANT-F:
                                      (SEQ. ID. 22)
atcgggcccCCGAAGTTGCTCACTTC
and pPttANT-R:
                                      (SEQ. ID. 23)
atcactagtGACAAGCTGAGAGACTG).
```

Also included are functional equivalents (fragments and variants) of a regulatory element as defined herein, wherein such equivalents are capable of directing vascular tissue specific expression of a coding region to which they are operably linked, preferably cambium or phloem specific expression. A preferred functional equivalent may show reduced non-desirable activity compared to the native regulatory element. A functional variant will preferably comprise at least 70% sequence identity to the PttANT or PttPP2 promoter sequence defined herein, more preferably at least 75%, 80%, 82%, 84%, 85%, 86%, 87%, 88%, 89%, 90%, 91%, 92%, 93%, 94%, 95%, 96%, 97%, 98%, 99%, or 100% sequence identity to the PttANT or PttPP2 promoter sequence defined herein.

A functional fragment is a portion of a regulatory element or variant thereof as defined herein, preferably which retains some or all of the biological activity of the full length regulatory element. Preferably, a functional fragment of a regulatory element as defined herein is capable of directing vascular tissue specific expression of a coding region to which they are operably linked, preferably cambium or phloem specific expression. A fragment may be 40%, 50%, 60%, 70%, 80%, 90%, or 95% of the length of the full length regulatory element. A fragment may be 40%, 50%, 60%, 70%, 80%, 90%, or 95% of the length of the full length PttANT or PttPP2 promoter sequence defined herein. Preferably, a fragment may be at least 30 amino acids in length, preferably at least 50, 70, 90, 100, 200, 300, 400 or 500 base pairs in length.

Growth and Structure

Preferably, altered growth is improved or increased growth, preferably vascular growth. Growth of a manipulated plant may be compared to growth of a wild type plant which has been maintained under identical conditions. Indicators of growth used are the radial diameter, vigour, growth rate, the amount of leaf tissue, the amount of biomass, and seed yield.

Radial diameter may be measured at breast height, for saplings and mature trees. The radial diameter may be used as an indication of biomass volume. It may be expressed as a unit of length. Vigour may be calculated by the increase in growth parameters, such as leaf area, fibre length, rosette diameter, plant fresh weight, and the like, per specified time period. An increase in vigour may be used to determine the plant yield, or may impact the plant yield (amount of tissue produced per plant per growing season). Growth rate can be measured using digital analysis of growing plants for example. Images of plants may be captured at regular intervals and the rosette area calculated by digital analysis. Rosette area growth is calculated using the difference between in area between the days of sampling divided by the difference in days between sampling. Alternatively, biomass produced, leaf size, root length etc. can be used as indicators of growth rate. Seed yield can be obtained by collecting the total seeds from a number of plants (e.g. 8-16), weighing them and dividing the total weight by the number of plants. Leaf tissue is preferably harvested and measured during summer, prior to leaf fall.

An altered structure may be a result of altered growth, or may be exhibited as the order of the vascular tissue. Wild type structure may be recognised by the ordered layout of the cells in defined rows, in contrast to an unordered structure where vascular tissue cells are present randomly without any recognisable pattern. A plant modified by the present invention will preferably show an ordered vascular tissue structure.

The vascular tissue comprises xylem, phloem and cambium cells. The phloem comprises living cells, responsible for transport within the plant. Phloem tissue may comprise conductive cells, parenchyma cells and supportive cells. The cambium lies between the phloem and xylem, and is a source of phloem and xylem cells. Xylem cells are also responsible for transport. Xylem cells are typically dead, and transport water within a plant.

The altered growth may be achieved by increasing the levels of PXY and/or CLE in a tissue specific manner in the vascular tissue of a plant. A manipulated plant may have increased levels/activity of PXY and/or CLE (or functional equivalents thereof) in the vascular tissue and at a preselected developmental stage, compared to the level/activity in the same tissue of a wild type plant of the same species, at the same developmental stage and grown in identical conditions.

Preferably, the levels of PXY are increased by at least about 5, 10, 20, 30, 40, 50, 60, 70, 80, 90% compared to the level of PXY in a wild type plant maintained under identical conditions. Preferred levels of CLE are increased by at least about 5, 10, 20, 30, 40, 50, 60, 70, 80, 90% compared to the level of CLE in a wild type plant maintained under identical conditions.

The increase in level of PXY may directly increase the activity of PXY in the tissue, or the activity may be increased independently of the amount of PXY present, for example through modulation of interaction between PXY and its ligand, CLE. Preferably, the activity of PXY is increased by at least about 5, 10, 20, 30, 40, 50, 60, 70, 80, 90% compared to the activity of PXY in a wild type plant maintained under identical conditions. Preferred activity of CLE is increased by at least about 5, 10, 20, 30, 40, 50, 60, 70, 80, 90% compared to the activity of CLE in a wild type plant maintained under identical conditions.

Increased growth may be defined as at least about 2%, at least about 3%, at least about 4%, at least about 5%, at least about 10%, at least about 15%, at least about 20%, at least about 30%, at least about 40%, at least about 50%, at least about 60%, at least about 70%, at least about 80% or greater increase in radial diameter, vigour, growth rate, the amount of leaf tissue, the amount of biomass, and/or seed yield as compared to a wild type plant maintained under identical conditions.

Alterations in growth and/or structure may be assessed at periodic intervals during the lifetime of a plant, and particularly in early development. For example, expression levels of PXY and/or CLE may be sampled at 3 or 6 monthly intervals, or annually.

The source of biomass in plants is their woody tissue, derived from the vascular meristems of the plant such as the cambium and procambium, which divide to form the phloem and xylem cells of the vascular tissue within the plant stems and roots. The cambium and procambium (collectively known as the vascular meristems) are growth zones which enable the plant to grow laterally, thus generating the majority of biomass. It has been shown that increasing levels of PXY and/or CLE in the vascular tissue of a plant enhances lateral growth, thereby leading to an increase in the plant biomass. This may provide an additional source of biomass for various industries dependent upon plant derived products, such as the biofuel or paper industries.

Expression Cassette

A regulatory element for directing tissue specific expression may be provided in an expression cassette, as described herein. In addition to a regulatory element for directing expression of PXY or CLE in the vascular tissue as described herein, an expression cassette may comprise terminator fragments, polyadenylation sequences, enhancer sequences, introns, and other sequences. These elements must be compatible with the remainder of the expression cassette. These elements may not be necessary for the expression or function of the gene but may serve to improve expression or functioning of the gene by affecting transcription, stability of the mRNA, or the like. Therefore, such elements may be included in the expression construct to obtain the optimal expression and function of PXY and CLE in the plant.

An expression cassette may further comprise additional region(s) that allows protein targeting, stabilization, and/or purification. The open reading frame may be orientated in either a sense or anti-sense direction. An expression cassette may be provided as part of a vector or expression construct.

An expression cassette may further comprise a second regulatory element for directing tissue specific expression of a second gene, e.g. PXY or CLE. The second regulatory sequence may be operably linked to the second gene, as described herein.

Where two or more coding sequences are operably linked to the same regulatory element, the coding sequences may be inter-linked via an internal ribosome entry site (IRES) sequence which facilitates translation of polynucleotide sequences positioned downstream of the IRES sequence.

Vectors

Herein, a vector is the vehicle used to transport the expression cassette into the cell, to produce a transformed or transgenic cell. Therefore a vector may comprise genetic material in addition to the expression cassette, for example one or more nucleic acid sequences that permit it to replicate in one or more host cells, such as origin(s) of replication, selectable marker genes and other genetic elements known in the art (e.g., sequences for integrating the genetic material into the genome of the host cell, and so on). The vector may be an expression vector.

Vectors include viral derived vectors, bacterial derived vectors, plant derived vectors and insect derived vectors. A vector will preferably be capable of propagating in both a bacterial host cell, such as *E. coli*, and be compatible with propagation in a plant cell. A vector may be a phagemid, plasmid, a phage, a virus, or an artificial chromosome.

A typical vector may comprise one or more of a promoter, selection marker, signal sequence, regulatory element (e.g. polyadenylation sequences, untranslated regions, 3' untranslated regions, termination sites and enhancers). Such companion sequences may be of plasmid or viral origin, and may provide the necessary characteristics to enable the vector to be generated in bacteria and introduced to a plant cell. A bacterial/plant vector may preferably comprise a broad host range prokaryote replication origin; a prokaryote selectable marker; and, for *Agrobacterium* transformations, T-DNA sequences for *Agrobacterium*-mediated transfer to plant chromosomes.

A cloning vector is designed so that a coding sequence (e.g. PXY or CLE) is inserted at a particular site and will be transcribed and translated. The basic bacterial/plant vector construct may preferably comprise a broad host range prokaryote replication origin; a prokaryote selectable marker; and, for *Agrobacterium* transformations, T-DNA sequences for *Agrobacterium*-mediated transfer to plant chromosomes. A vector may also comprise suitable sequences for permitting integration of the expression cassette into the plant genome. These might include transposon sequences, Cre/lox sequences and host genome fragments for homologous recombination, as well as Ti sequences which permit random insertion of an expression cassette into a plant genome.

A vector of the present invention may comprise a transcriptional termination region at the opposite end of the gene from the transcription initiation regulatory region. The transcriptional termination region may normally be associated with the transcriptional initiation region or derived from a different gene. The transcriptional termination region to be used may be selected, particularly for stability of the mRNA, to enhance expression. Examples of termination regions include the NOS terminator from *Agrobacterium* Ti plasmid and the rice α-amylase terminator.

Selectable markers encode easily assayable marker proteins are well known in the art. In general, a selectable marker is a gene which is not present or expressed by the recipient organism or tissue and which encodes a protein whose expression is manifested by some easily detectable property, e.g. phenotypic change or enzymatic activity. Suitable selectable marker may be used to facilitate identification and selection of transformed cells. These will confer a selective phenotype on the plant or plant cell to enable selection of those cells which comprise the expression cassette. Preferred genes include the chloramphenicol acetyl transferase (cat) gene from Tn9 of *E. coli*, the beta-gluronidase (gus) gene of the uidA locus of *E. coli*, the green fluorescence protein (GFP) gene from *Aequoria victoria*, and the luciferase (luc) gene from the firefly *Photinus pyralis*. If desired, selectable genetic markers may be included in the vector, such as those that confer selectable phenotypes such as resistance to antibodies or herbicides (e.g. kanamycin, hygromycin, phosphinotricin, chlorsulfuron, methotrexate, gentamycin, spectinomycin, imidazolinones and glyphosate). A selectable marker may be provided on the same expression cassette or vector as the tissue specific regulatory element, or may be provided on a separate expression cassette and co-transformed with the expression cassette of the invention. A selectable marker and/or reporter gene may be flanked with appropriate regulatory sequences to enable their expression in a plant cell.

An expression cassette may be utilized to stably or transiently transform plant cells. In stable transformation, the exogenous polynucleotide is integrated into the plant genome and as such it represents a stable and inherited trait. In transient transformation, the exogenous polynucleotide is expressed by the cell transformed but it is not integrated into the genome and as such it represents a transient trait.

For further details see, for example, Molecular Cloning: Laboratory Manual: 2$^{nd}$ edition, Sambrook et al. 1989, Cold Spring Harbor Laboratory Press or Current Protocols in Molecular Biology, Second Edition, Ausubel et al. Eds., John Wiley & Sons, 1992.

Methods of Transformation

Methods to transform woody species of plant are well known in the art. For example the transformation of poplar is disclosed in U.S. Pat. No. 4,795,855 and WO91 18094. The transformation of *eucalyptus* is disclosed in EP1050209 and WO9725434.

An expression cassette or vector of the present invention may be used to stably or transiently transform a plant cell. In stable transformation, the exogenous polynucleotide is integrated into the plant genome and as such it represents a stable and inherited trait. In transient transformation, the exogenous polynucleotide is expressed by the cell transformed but it is not integrated into the genome and as such it represents a transient trait.

Stable integration may include i) *Agrobacterium*-mediated gene transfer (ii) Direct DNA uptake. The latter may include including methods for direct uptake of DNA into protoplasts, DNA uptake induced by brief electric shock of plant cells: DNA injection into plant cells or tissues by particle bombardment by the use of micropipette systems; glass fibres or silicon carbide whisker transformation of cell cultures, embryos or callus tissue, or by the direct incubation of DNA with germinating pollen.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. A supplementary approach employs the *Agrobacterium* delivery system in combination with vacuum infiltration. The *Agrobacterium* system is especially viable in the creation of transgenic dicotyledonous plants.

The regenerated transformed plants can then be crossbred and resultant progeny selected for superior growth, biomass, yield and/or vigor traits, using conventional plant breeding techniques.

Routine assays may be used to screen for those which have the desired properties. This may be done by visual observation of plants and plant material, or measuring the biomass of the plant or plant material.

Plant

A transgenic plant will include a plant that is grown from a recombinant plant cell, and all ancestors and progeny of that plant that contain the recombinant nucleic acid. This includes offspring produced sexually or asexually. It is understood that the term transgenic plant encompasses the entire plant or tree and parts of the plant or tree, for instance grains, seeds, suspension cultures, flowers, leaves, roots, fruit, pollen, callus tissue, gametophytes, sporophytes, stems, embryos, microspores etc.

Preferred plants for use in the present invention are those which are targets for biomass, and/or are readily grown, exhibit high growth rates, are easily harvested, and can be readily converted to a biofuel. Preferred plants include grasses, trees, crops, and shrubs.

According to some embodiments of the invention, the plant used by the method of the invention is a crop plant such as rice, maize, wheat, barley, peanut, potato, sesame, olive tree, palm oil, banana, soybean, sunflower, canola, sugarcane, alfalfa, millet, leguminosae (bean, pea), flax, lupinus, rapeseed, tobacco, popular and cotton.

Suitable plants for use in the present invention are those which in their native form produce a high yield of feedstock, for paper or fuel production. Examples of suitable plant types include perennial fast growing herbaceous and woody plants, for example trees, shrubs (such as tobacco) and grasses. Trees for use in the invention include birch, spruce, pine, poplar, hybrid poplar, willow, silver maple, black locust, sycamore, sweetgum and *eucalyptus*. Perennial grasses include switchgrass, reed canary grass, prairie cordgrass, tropical grasses, Brachypodiumdistachyon, and Miscanthes. Crops include cereals and pulses, wheat, soybean, alphalpha, corn, rice, maize, and sugar beet, potatoes, tapioca, *sorghum*, millet, cassava, barley, pea, and other root, tuber or seed crops. Important seed crops are oil-seed rape, sugar beet, maize, sunflower, soybean, and *sorghum*. According to a further embodiment of the invention said plant is a woody plant selected from: poplar; *eucalyptus*; Douglas fir; pine; walnut; ash; birch; oak; teak; spruce. Horticultural plants to which the present invention may be applied may include lettuce, endive, and vegetable *brassicas* including cabbage, broccoli, and cauliflower, and carnations and geraniums. The present invention may be applied in tobacco, cucurbits, carrot, strawberry, sunflower, tomato, pepper, *chrysanthemum*. Grain plants that provide seeds of interest include oil-seed plants and leguminous plants. Seeds of interest include grain seeds, such as corn, wheat, barley, rice, *sorghum*, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

In a further embodiment of the invention said plant is selected from: corn (*Zea mays*), canola (*Brassica napus, Brassica rapa* ssp.), alfalfa (*Medicago sativa*), rice (*Oryza sativa*), rye (*Secale cerale*), sorghum (*Sorghum bicolor, Sorghum vulgare*), sunflower (*helianthus annuas*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*lopmoea batatus*), cassava (*Manihot esculenta*), coffee (*Cofea* spp.), coconut (*Cocos nucifera*), pineapple (*Anana comosus*), citrus tree (*Citrus* spp.) cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, barley, vegetables and ornamentals.

Plant Derived Product

The present invention has uses in methods which require increased biomass in plants, for example where plant biomass is used in the manufacture of products such as biofuels and paper. The invention is not limited to methods of making these particular products, and it is envisaged that the invention will be applicable to the manufacture of a variety of plant based products. In addition, the invention is also useful in altering the characteristics of plant material, such that the plant material may be adapted for particular purposes (such as disclosed in WO2010029357, which is incorporated in its entirety by reference).

A plant-derived product may include seed, biomass, fibres, forage, biocomposites, biopolymers, wood, biofuel, board or paper.

Throughout the description and claims of this specification, the words "comprise" and "contain" and variations of them mean "including but not limited to", and they are not intended to (and do not) exclude other components. Throughout the description and claims of this specification, the singular encompasses the plural unless the context otherwise requires. In particular, where the indefinite article is used, the specification is to be understood as contemplating plurality as well as singularity, unless the context requires otherwise.

Features described in conjunction with a particular embodiment of the invention are to be understood to be applicable to any other embodiment described herein unless incompatible therewith. All of the features disclosed in this specification (including any accompanying claims and drawings) may be combined in any combination, except combinations where at least some of such features and/or steps are mutually exclusive. The invention extends to any novel one, or any novel combination, of the features disclosed in this specification (including any accompanying claims and drawings).

The invention is further described in the following examples with reference to the Figures, in order to illustrate the invention in a non-limiting manner:

EXAMPLES

Binary Vectors for Plant Transformation

For poplar 35S overexpression vectors, primers were designed against *Populus trichocarpa* (Tuskan et al (2006). Science 313, 1596-1604) CLE41 (Potri.012G019400):

```
PttCLE41-F:
                                        (SEQ. ID. 24)
CACCTAGCTAGCCTTGGTGCTGGT

PttCLE41-R:
                                        (SEQ. ID. 25)
ACCCCTTAATTCCCCCATTA
``` and PXY (Potri.003G107600):

```
PttPXYF:
                                        (SEQ. ID. 26)
CACCATGAAACTCCCTTTTCTTTT

PttPXY-R
                                        (SEQ. ID. 27)
ACATTCGACTGCAGGCTTTT
``` and used to amplify sequences from DNA extracted from hybrid aspen (*Populus tremula* x *tremuloides* clone T89). These were subsequently cloned into pK2GW7 (Karimi, et al (2002). Trends in Plant Science 7, 193-195. 2) via pENTR-D-TOPO. For the rolD::PttPXY 35S::CLE41 construct, PttCLE41 was subcloned into pDONRP4-P3 which was combined with pENTR-D-TOPO-PttPXY and pK7m34GW2-8m21GW3 (Karimi et al (2007) Plant Physiology 145, 1183-1191) using an LR clonase reaction. Cloned PttPXY and PttCLE41 were sequenced either in entry clones or expression clones. Sequences were annotated by aligning with *P. trichocarpa* sequences. Annotated sequences for PttPXY (accession number, KP682331) and PttCLE41 (accession number, KP682332) were submitted to NCBI. During the cloning a mutation was accidently introduced that had removed the stop codon at the end of the PttPXY gene and resulted in a 44 amino acid extension encoded by the vector being added to the C terminus.

For tissue specific expression, PttPXY and PttCLE41 pENTR-D/TOPO entry clones were used in an LR clonase reaction in combination with custom Gateway destination vectors, pVX31 (ApaI-pPttANT1-SpeI-R1R2 Gateway Cassette-t35S-SbfI and pVX33 (SM-pPtPP2-SpeI-R1R2 Gateway Cassette- t35S-SM), which were constructed in a pCambia2300 backbone using restriction based cloning. The promoter sequences were chosen on the basis of poplar expression data. PttANT (Potri.002G114800) regulatory sequences were used for cambium specific expression and a PtPP2 (Potri.015G120200) promoter was used for phloem specific expression. For the PtPP2 promoter from *Populus trichocarpa* primers (pPtPP2-F atccctaggcctgcaggTAAGC-TATGTACGTTTTGG (SEQ. ID. 20), pPttANT-R atcactagtGACAAGCTGAGAGACTG (SEQ. ID. 21) were used to amplify a fragment of 1999 bp upstream of the start codon. For the PttANT1 promoter, primers (pPttANT-F atcgggcccCCGAAGTTGCTCACTTC (SEQ. ID. 22), pPttANT-R atcactagtGACAAGCTGAGAGACTG (SEQ. ID. 23)), were used to amplify a sequence 1156 bp upstream of start codon to 904 bp downstream of the start codon that drove expression in vascular tissue. To create the double tissue specific expression construct, SbfI-pPtPP2-PttCLE41-t35S-SbfI cassette was excised and cloned into SbfI site of ApaI-pPttANT1-PttPXY-t35S-SbfI. Transcriptional reporter lines for pPttANT and pPtPP2 were generated by cloning a fragment encoding eGFP-GUS in in pVX31 and pVX33 using an LR clonase reaction resulting in pPttANT::eGFP-GUS and pPttPP2::eGFP-GUS constructs. Hand sections were stained using a variation on the method described in Rodrigues-Pousada ((1993) The Plant Cell Online 5, 897-911) and were viewed following clearing by overnight incubation at 4° C. in chloral hydrate solution (Berleth, et al (1993) Development 118, 575-587).

Plant Transformation

Arabidopsis transformation was carried out using the method of Clough and Bent (Clough, S. J., and Bent, A. F. (1998). Plant Journal 16, 735-743). For transformation of hybrid aspen (clone T89), a method based on that of Nilsson et al ((1992) Transgenic Research 1, 209-220) was used. Briefly, Agrobacterium strain GV3101 harbouring a binary vector was grown to an OD600 of 0.6, collected by centrifugation in a 50 ml tube and resuspended in MS medium, pH5.8 supplemented with acetosyringone to a final concentration of 25 µM at room temperature. Leaf and petiole sections were cut from hybrid aspen grown under sterile conditions and incubated in the resuspended Agrobacterium for 1 hour and placed on MS agar supplemented with 2% sucrose, BAP (0.2 mg/L), IBA 0.1 mg/L and TDZ (0.1 mg/L) prior to incubation in dark for 48 hours. Subsequently, plant pieces were rinsed in MS and placed in the light on MS agar supplemented with 250 µg/ml cefatoxime and 100 µg/ml kanamycin. Following shoot initiation calli were transferred to woody plant medium (WPM) supplemented with sucrose (2%), BAP (0.2 mg/L), IBA (0.1 mg/L), kanamycin (100 µg/ml) for shoot elongation and subsequently to WPM for rooting. In order to synchronise plant growth for subsequent analysis the top 2 cm of each plantlet to be used was removed and re-rooted on the same day. All plants used for growth analysis were grown side by side in the same incubator and transferred to soil on the same day once roots were established. For long term growth, plants were transferred to a greenhouse in April and maintained for up to 12 months.

Determination of Plant Growth Characteristics

Vascular organization was determined using plant material fixed in FAA, dehydrated through an ethanol series before infiltration and embedding with JB4 embedding media. 5 µM sections were stained with 0.05% aqueous toluidine blue, mounted in Cytoseal and visualised on a Leica 5500 microscope. Vascular tissue was considered to be ordered if xylem could be incorporated in an elliptical shape that excluded the phloem. Xylem cell counts and determination of cell wall area was performed on cross sections from the entire cross section of tissue culture plants 3 weeks post rooting or from the 50th internode of greenhouse grown plants in which case only a 40° segment of the stem was used (FIG. S6A). Cell counting was carried out using Cellprofiler (Carpenter et al (2006) Genome Biol 7, R100) as outlined in FIG. S6. For greenhouse grown plants, 10 cm segments were sampled from base of the plant, from 50th internode and from the top of the plants, 12 months following transfer to soil. Material was dried at 50° C. for 4 weeks before weighing.

Results and Discussion

Figure 5:
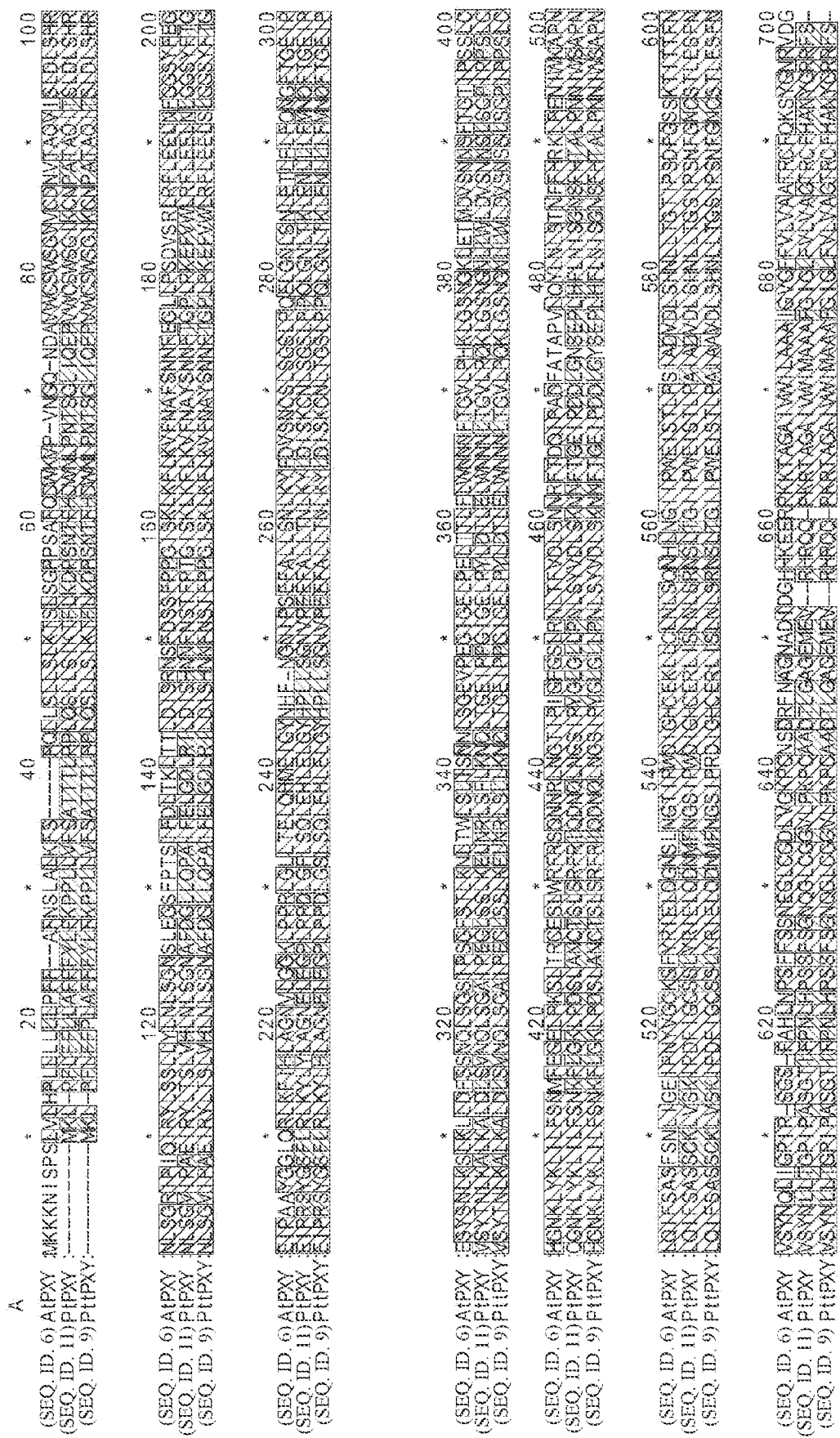
FIG. 5 shows amino acid sequence alignment of PXY and CLE. (A) Alignment of PXY sequences from *Arabidopsis* (AtPXY, AT5G61480), *P. trichocarpa* (PtPXY, Potri.003G107600) and hybrid Aspen (PttPXY, this study). (B) Alignment of CLE41 sequences from *Arabidopsis* (AtCLE41, AT3G24770), *P. trichocarpa* (PtCLE41, Potri.012G019400) and hybrid Aspen (PttCLE41, this study). TDIF peptides within the CLE41 sequences are indicated by the black rectangle. Ptt sequences were obtained by translating the ORF from plasmids containing PttPXY and Supplemental Data PttCLE41 genes cloned as part of this study. Other protein sequences were obtained from phytozome (http://www.phytozome.net/).
Figure 5:
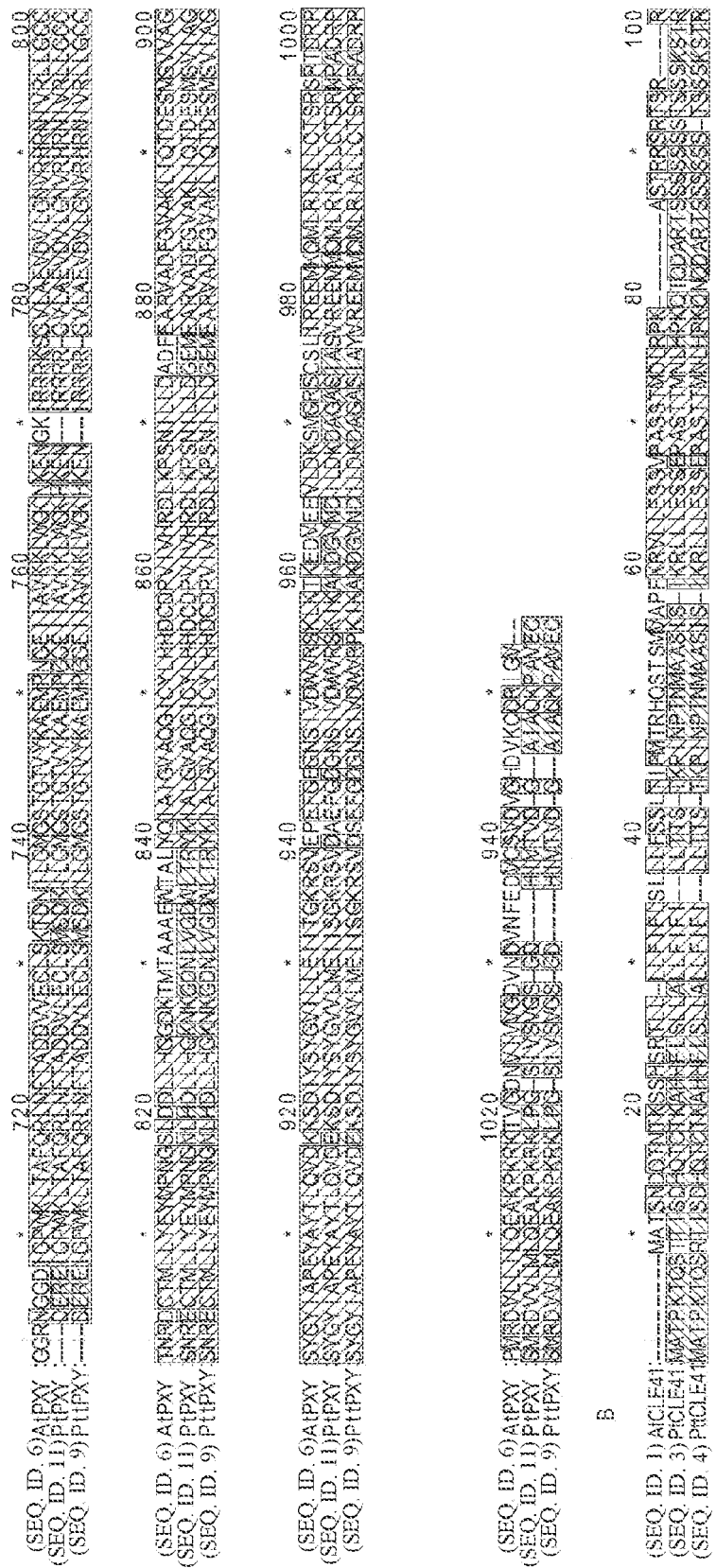
Figure 6:
FIG. 6 shows Poplar CLE41 and PXY genes are functional in *Arabidopsis*. Sections from *Arabidopsis* hypocotyls (LHS) and inflorescence stem vascular bundles (RHS) from typical wild type (A), 35S::PttCLE41 (B), pxy mutant (C), and a pxy mutant complemented with 35S::PttPXY (D). Scales bars indicate 50 µM.
Figure 6:
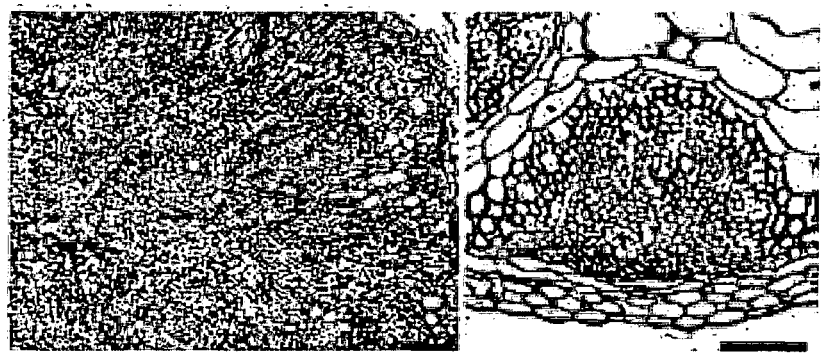
Figure 6:
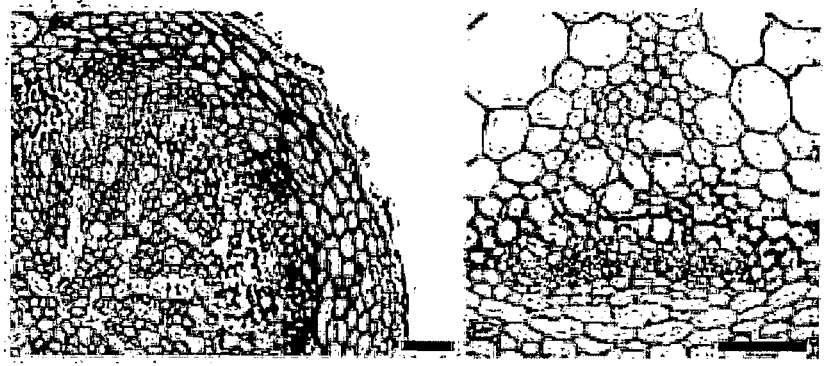
Figure 6:
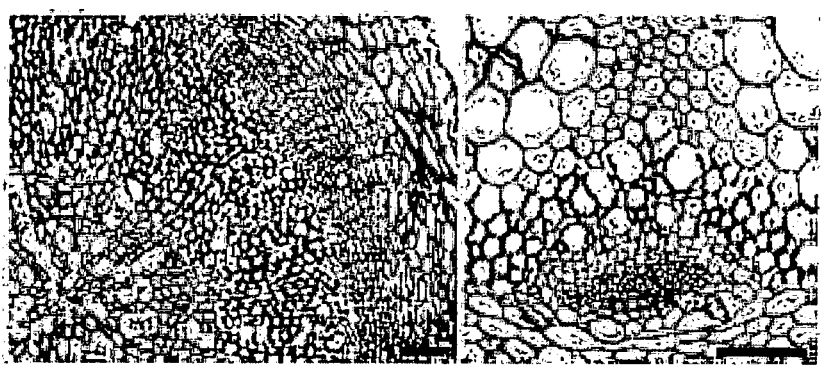
Figure 7:
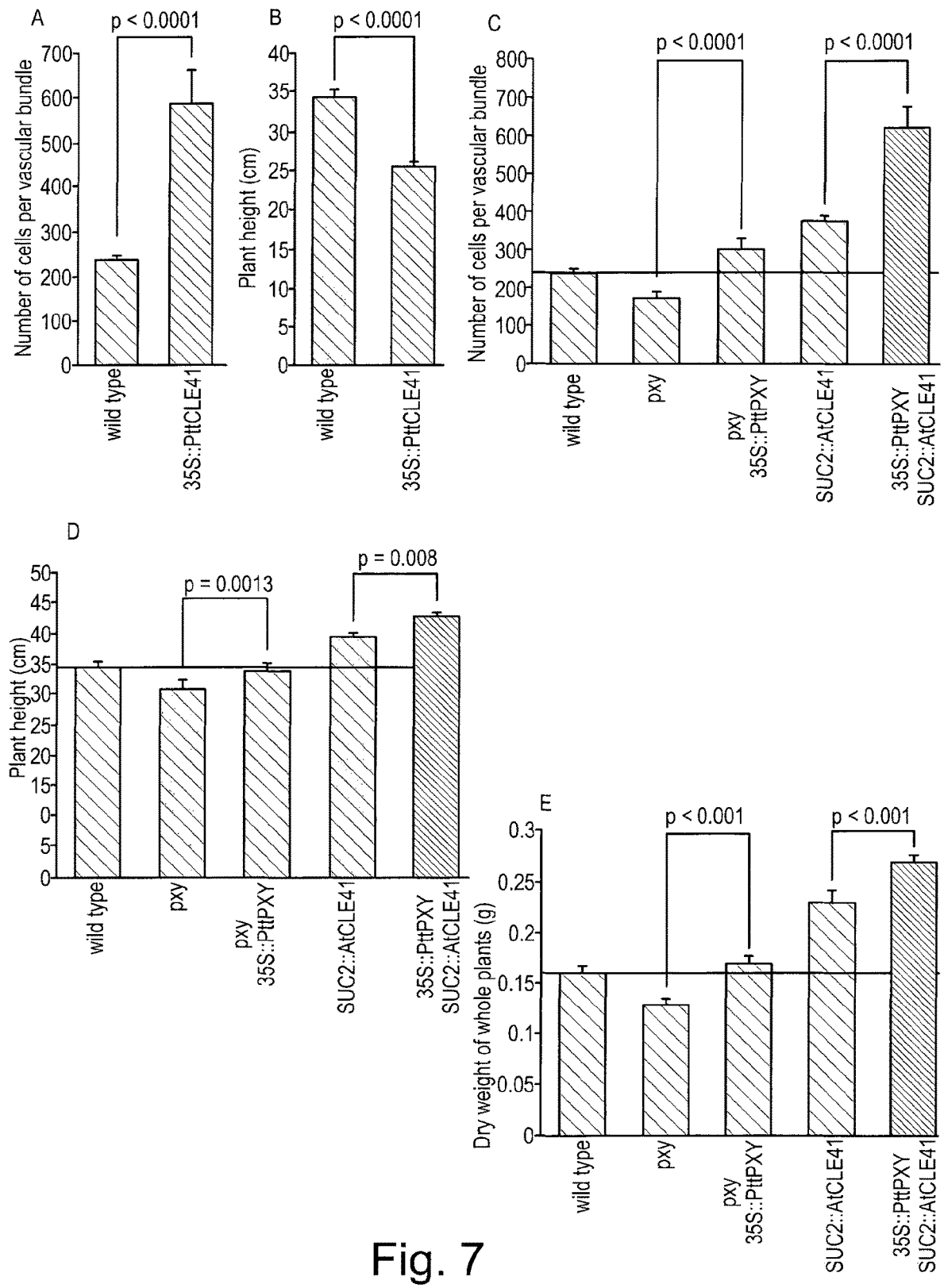
FIG. 7 shows growth characteristics of *Arabidopsis* lines overexpressing poplar PXY genes. Number of cells per vascular bundle (A) and plant height (B) of *Arabidopsis* 35S::PttCLE41 lines compared to wild type counterparts. Number of cells per vascular bundle (C), plant height (D) and dry weight (E) of *Arabidopsis* pxy, pxy35S::PttPXY, SUC2::AtCLE41, SUC2::AtCLE41-35S::PttPXY lines compared to wild type counterparts. P values were calculated with an ANOVA and LSD post-hoc test with N=10 (A,C) or 40 (B,D,E).

The PXY-CLE signalling pathway is conserved in trees and acts to regulate secondary growth: Wood is composed of xylem cells that arise from divisions of stem cells that reside within the vascular meristem, known as the cambium or procambium. One mechanism that promotes cell division in vascular meristems of Arabidopsis involves phloem-specific expression of CLE41 that encodes a peptide ligand known as TDIF. TDIF is perceived by a receptor kinase, PXY (also known as TDR) that is expressed in the adjacent stem cells of the procambium (Etchells, and Turner (2010) Development 137, 767-774; Fisher and Turner (2007) Current Biology 17, 1061-1066; Hirakawa (2008) Proceedings of the National Academy of Sciences, USA 105, 15208-15213; Kondo et al (2006) Science 313, 845-848). PXY controls both the orientation (Etchells and Turner (2010) Development 137, 767-774) and rate of cell division in procambial stem cells (Etchells et al, (2013) Development 140, 2224-2234; Hirakawa et al (2010) Plant Cell 22, 2618-2629) and inhibits their differentiation into xylem (Hirakawa et al (2008) Proceedings of the National Academy of Sciences, USA 105, 15208-15213; Kondo et al (2014) Nat Commun 5). Consequently, while ectopically overexpressing CLE41 in Arabidopsis increases the number of cells in vascular bundles, these increases are accompanied by repression of xylem differentiation and loss of vascular organization (Etchells and Turner (2010) supra; Hirakawa, et al (2008) supra; Whitford et al (2008) Proceedings of the National Academy of Sciences USA 105, 18625-18630). Furthermore, output from the pathway is regulated by a negative feedback loop in which CLE41 expression results in down regulation of PXY (Etchells and Turner (2010) supra). To determine whether PXY-CLE41 signalling is conserved in poplar, putative orthologous of PXY and CLE41 genes were cloned from the hybrid aspen (Populus tremula×P. tremuloides) referred to hereafter as PttPXY and PttCLE41 respectively (FIG. 5). When overexpressed in Arabidopsis, 35S::PttCLE41 lines demonstrated a loss of vascular organisation, increased numbers of cells per vascular bundle and decreased plant height (FIGS. 6A,B, 7A,B). The 35S::PttPXY construct complemented the Arabidopsis pxy mutant phenotype (FIGS. 6C-D, 7C-E) and this complemented line also restored the ability of the plants to respond to overexpression of the AtCLE41 ligand (FIG. 7C,D). As such, both PttCLE41 and PttPXY clones act as functional orthologues of their respective Arabidopsis genes. Furthermore expression of PttPXY in Arabidopsis plants already engineered for tissue-specific AtCLE41 over-expression resulted in increased plant biomass (FIG. 7E).

Ectopic Expression of PttCLE41 or PttPXY Leads to Abnormal Vascular Tissue Development in Trees.

Figure 8:
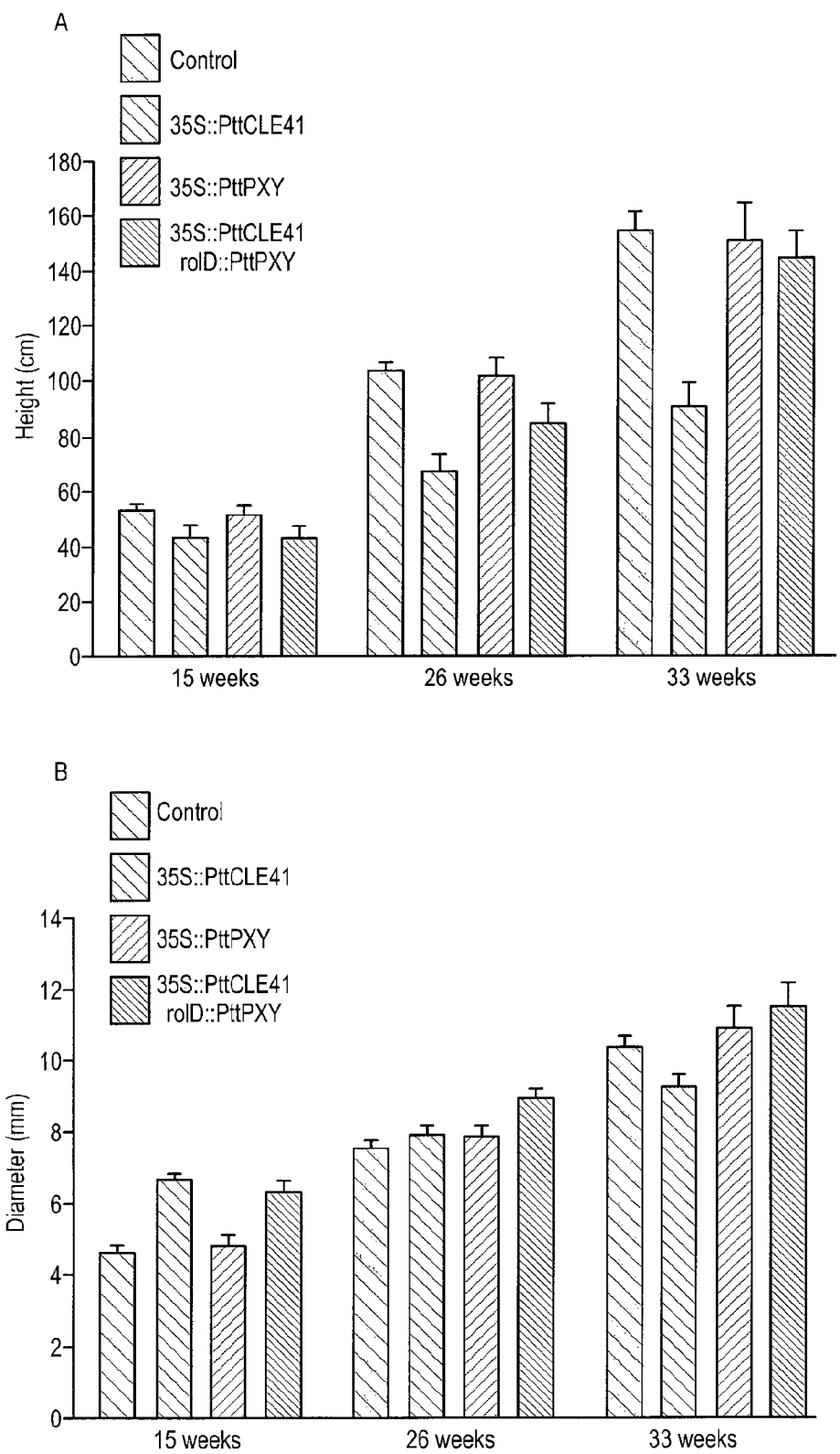
FIG. 8 shows growth characteristics of hybrid aspen lines overexpressing PttCLE41/PttPXY. Height (A) and diameter (B) measurements from hybrid aspen grown in soil. Trees rooted in April, were measured at 15 weeks (July), 26 weeks (August) and 33 weeks (October). N=15.

The consequence of constitutively over-expressing these genes in trees was investigated by making use of the 35S promoter that is known to give widespread expression in hybrid aspen (Nilsson et al (1996) Plant Mol. Biol. 31, 887-895). The 35S::PttPXY and 35S::PttCLE41 constructs (see above) were individually over-expressed or over-expressed both genes together in a single binary plasmid containing that contained 35S::PttCLE41 and rolD::PttPXY cassettes. To varying degrees, all independent lines (n=15) of 35S::PttCLE41 hybrid aspen had intercalated xylem and phloem (FIG. 1A). 35S::PttPXY lines (n=10) also demonstrated disrupted organisation in parts of the xylem, but to a much lesser extent than seen in 35S::PttCLE41 (FIG. 1A). 7 out of 15 35S::PttCLE41-rolD::PttPXY lines appeared normal while the remaining 8 exhibited varying degrees of tissue disruption (FIG. 1A). None of these lines led to significant increases in tree growth, in fact 35S::PttCLE41 lines were significantly shorter than wild type, exhibiting various growth abnormalities (FIG. 1B and FIG. 8).

Tissue Specific Expression of PttPXY and PttCLE41 Increases Vascular Cell Division and Retain Normal Vascular Tissue Organization.

Figure 2:
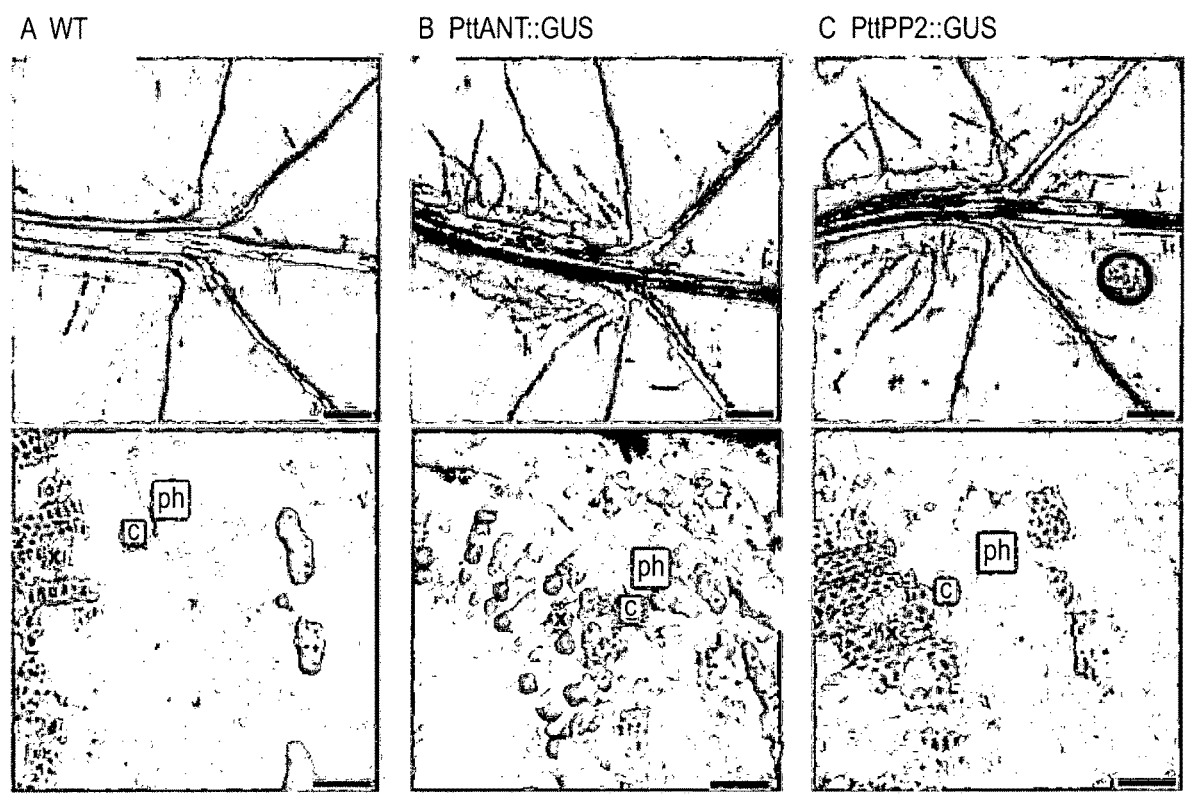
FIG. 2 shows the expression patterns derived from PttANT and PtPP2 promoters. GUS stained and cleared control (A), PttANT::GUS (B) and PtPP2::GUS (C) plants. Upper panels show leaves, lower panels are transverse stem sections. Scale bars indicate 200 μm (upper panels) 100 μm (lower panels).
Figure 10:
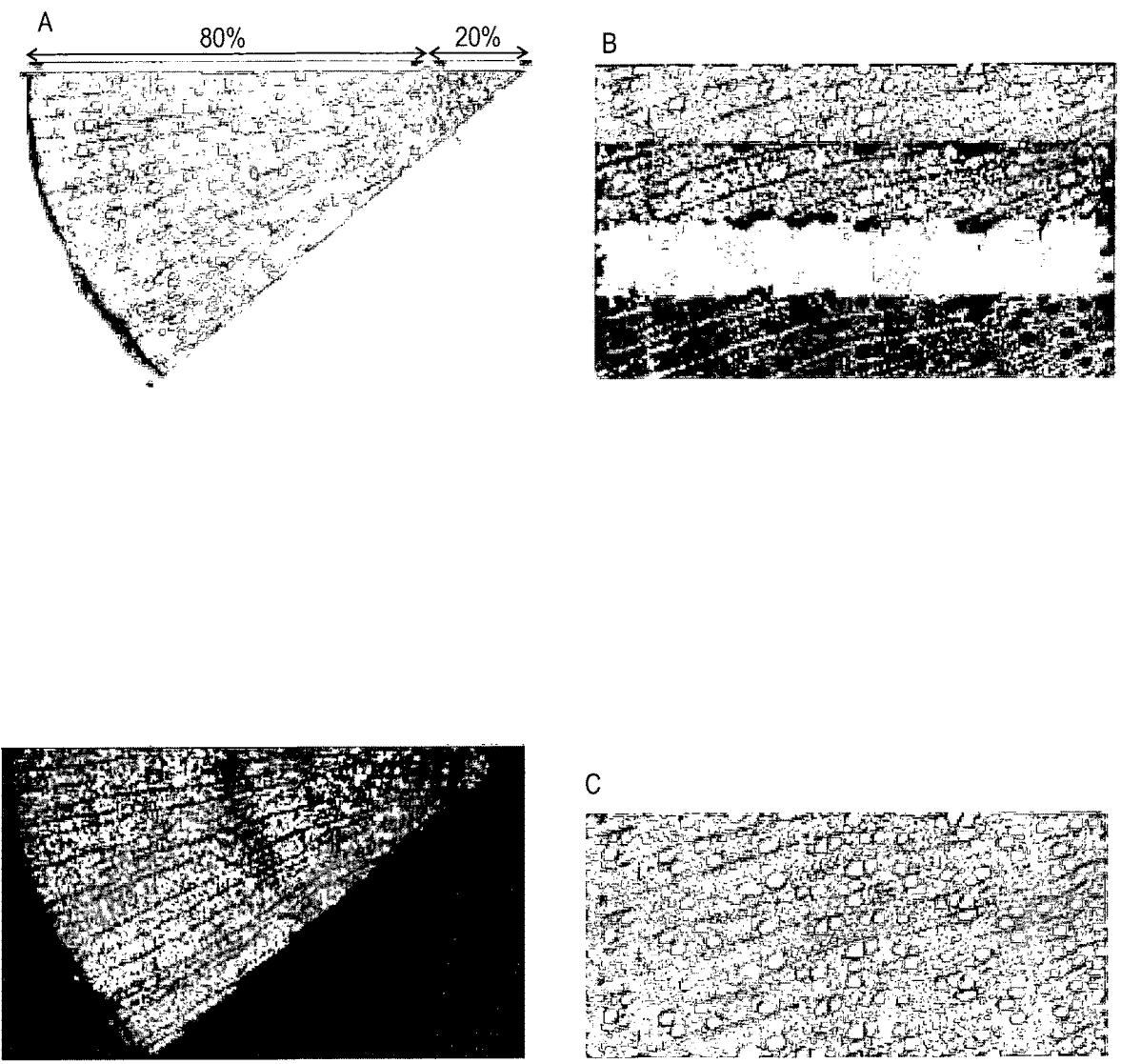
FIG. 10 shows phenotypic characterisation using Cellprofiler. (A): Transverse stem section from the 50th internode showing xylem in a sector with a central angle of 40° C. (top) and recognition of cell lumens by Cellprofiler (below). Cells were identified with greater than 95% accuracy, but cells with no clear lumen, such as ray cells or very small fiber cells, were not recognized. (B): Measurement of cell size and cell wall area is based upon a rectangle (top) outlined in (a). Primary objects (cell lumens) were identified (upper middle) and propagated outwards to identify the secondary objects (lower middle). The tertiary objects (cell walls) were obtained by subtracting the primary objects from the secondary objects (bottom). (C): Identification of vessels based upon identifying primary objects (middle) and then filtering by size and shape (bottom).

It was hypothesized that the tissue-specific expression of both PttPXY and PttCLE41 might be important both for tissue organization and to maximize cambial cell division. Transcriptomic data shows that in poplar, PXY is expressed predominantly in the cambium and at a low level in the xylem (Schrader et al (2004) Plant Cell 16, 2278-2292). Poplar microarray data identified the ANTEGUMENTA (ANT) gene as highly expressed only within the division zone (Schrader et al (2004) supra). Using an early draft of the *Populus trichocarpa* genome (Tuskan et al (2006) supra) as a guide, we identified and cloned a putative promoter from hybrid aspen (PttANT), although better annotation of the genome subsequently suggested the PttANT promoter fragment contained sequences both upstream and downstream of the putative transcriptional start site. Analysis of leaves from PttANT::GUS plants showed clear vascular specific GUS expression, while in the stems, GUS activity was restricted to the dividing cambial zone (FIG. 2B) consistent with our initial interpretation of the expression data. We also identified and cloned regulatory sequences from a phloem specific lectin gene, PHLOEM PROTEIN2 (PP2), from *Populus trichocorpa* (PtPP2). GUS analysis verified this promoter as vascular tissue specific in the leaves and giving excellent phloem-specific expression in stems (FIG. 2C). These promoters were used to generate 3 constructs designed to give tissue specific increases in expression: PttANT::PttPXY, PtPP2::PttCLE41 and PtPP2::PttCLE41-PttANT::PttPXY. In contrast to 35S::PttCLE41 (FIG. 1A), PtPP2::PttCLE41 lines demonstrated highly organized vasculature in all 14 lines examined (FIG. 10). 7 out of 15 PttANT::PttPXY lines demonstrated minor disruptions in xylem morphology (FIG. 10; arrow) similar to those observed in 35S::PttPXY trees (FIG. 1A), however all 12 independent PtPP2::PttCLE41-PttANT::PttPXY double overexpression lines analysed exhibited highly organized vascular tissue comparable to that of wild-type controls (FIG. 10). Strikingly, PtPP2::PttCLE41, PttANT::PttPXY and PtPP2::PttCLE41-PttANT::PttPXY double overexpression lines clearly demonstrated increases in the number of vascular cells as early as 3 weeks post rooting in tissue culture (FIG. 10 and FIG. S5A).

Tissue Specific Expression of PttPXY and PttCLE41 Results in Trees that Grow Faster.

Figure 3:
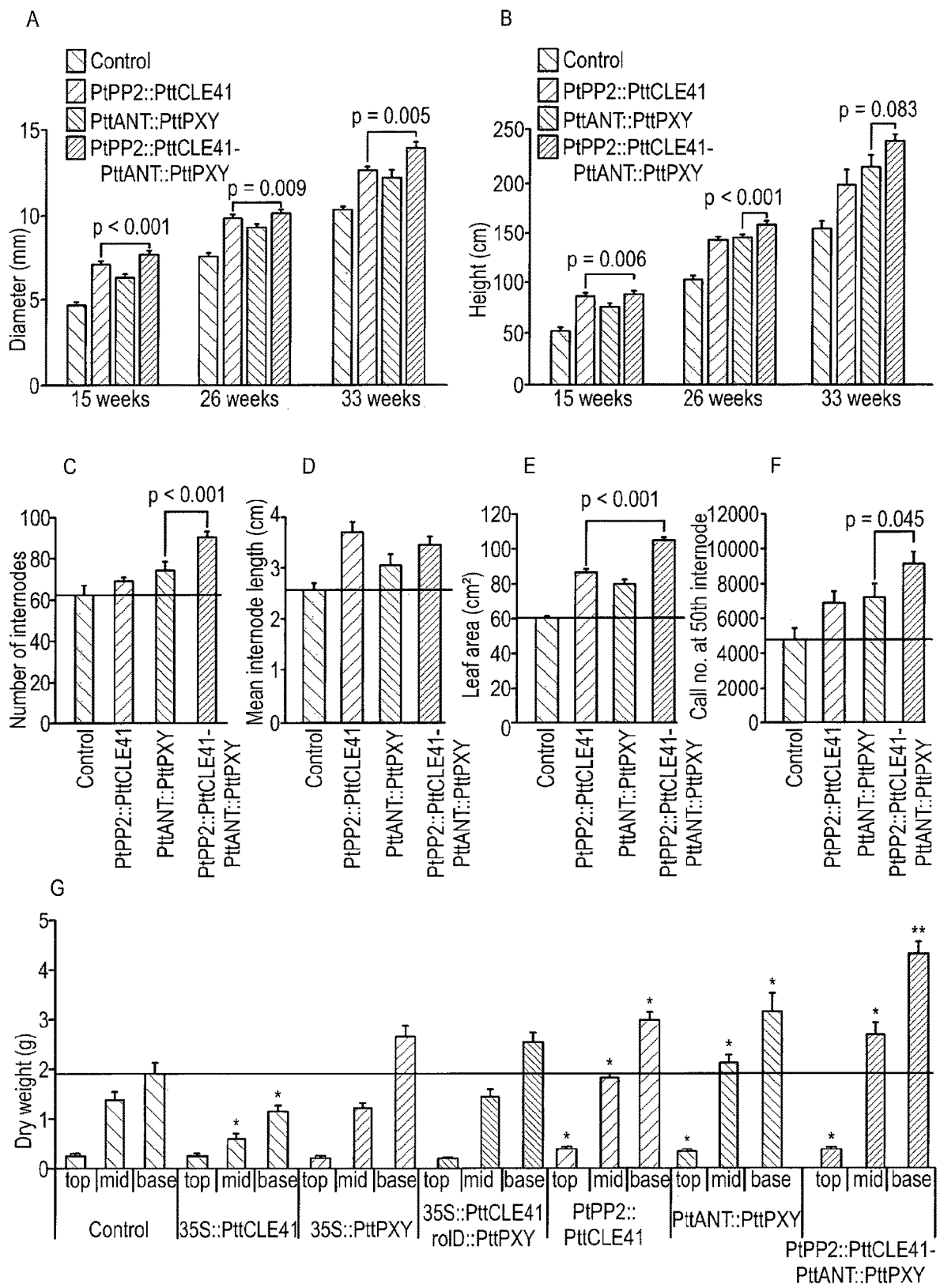
FIG. 3 shows the growth characteristics of trees with targeted PttCLE41/PttPXY overexpression. Mean stem diameter (A) and plant height (B) measurements from hybrid aspen grown in soil are shown. Trees rooted in April were measured at 15 weeks (July), 26 weeks (August) and 33 weeks (October). Further analysis of 6 month old plants: number of internodes (C), length of 50th internode (D), leaf area calculated from measurements of 5 leaves from around the 50th internode (E) and xylem cell number in a stem cross sector with a central angle of 40° C. (F). (G) Graph showing dry weight of 10 cm pieces of sapling stem. Samples were taken from the base, middle (50th internode) and top, except for 35S::PttCLE41 which had less than 50 internodes and a section taken midway between the top and bottom was used instead. All p values were calculated with an ANOVA and a LSD post-hoc test, n=15 (A-E) or 8 (F, G).

The growth of these transgenic hybrid aspen trees was further monitored following transfer to soil and maintenance in the greenhouse. Over a 6 month period PtPP2::PttCLE41, PttANT::PttPXY and PtPP2::PttCLE41-PttANT::PttPXY plants grew normally (FIG. 10) and were consistently larger than the control plants with both greater stem diameter and plant height (FIG. 3A,B). PtPP2::PttCLE41-PttANT::PttPXY lines gave the largest increase in radial growth and after 6 months in the greenhouse exhibited a 35% increase in stem diameter compared to untransformed controls and an increase of 10% compared to PtPP2::PttCLE41, the next best performing genotype (FIG. 3A). The PtPP2::PttCLE41-PttANT::PttPXY lines also demonstrated a 56% increase in height over their wild-type counterparts and a 12% increase in height over the next-best performing transgenic line (PttANT::PttPXY) (FIG. 3B). This increase was due to a generally faster growth rate with PtPP2::PttCLE41-PttANT::PttPXY plants having on average 90 internodes compared to the a mean of 60 for control plants (FIG. 3C), as well as an increase in internode length (FIG. 3D). While the plants appeared morphologically normal (FIG. 10), the PtPP2::PttCLE41-PttANT::PttPXY lines also exhibited increases in leaf area (FIG. 3E) with the average leaf area increased by almost 2 fold. These increases in growth reflect PXY/CLE signalling acting on other aspects of plant development or be a consequence of increases in sink strength. They contribute to a general increase in biomass that is likely to further improve the effectiveness of any biotechnological application of these discoveries.

Tissue Specific Expression of PttPXY and PttCLE41 Results in Large Increases in Wood and Biomass Formation.

Figure 11:
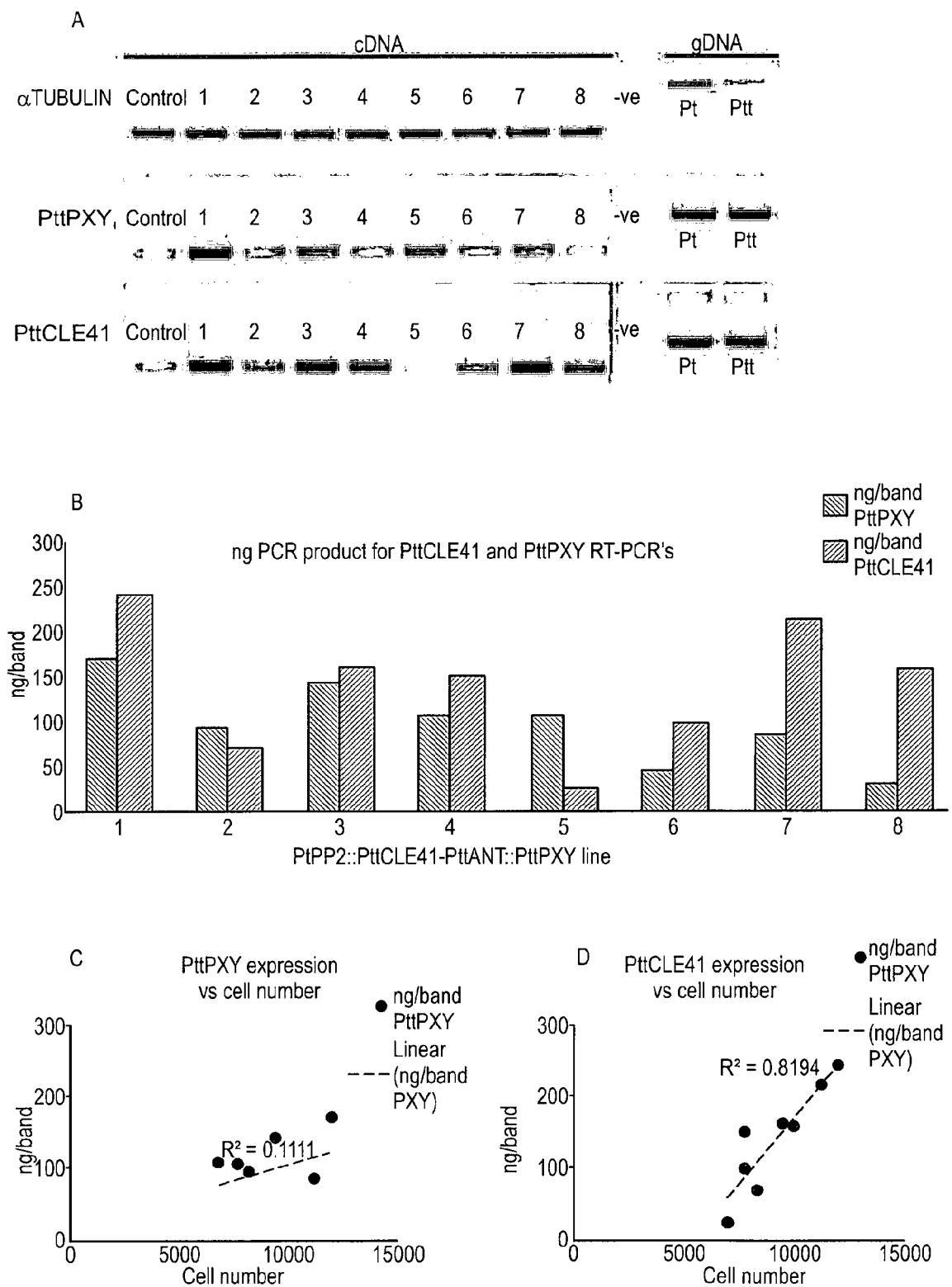
FIG. 11 shows PttCLE41 and PttPXY expression analysis in PtPP2::PttCLE41-PttANT::PttPXY lines. (A): RT-PCR showing expression in 8 independent transgenic lines. Stem material was taken adjacent to the 50th internode. (B): Relative intensity of PCR product in (A), was determined using Image Lab 5.1 software (Bio-rad). (C): Relationship between cell number and PttPXY expression. (D): Relationship between cell number and PttCLE41 expression.
Figure 12:
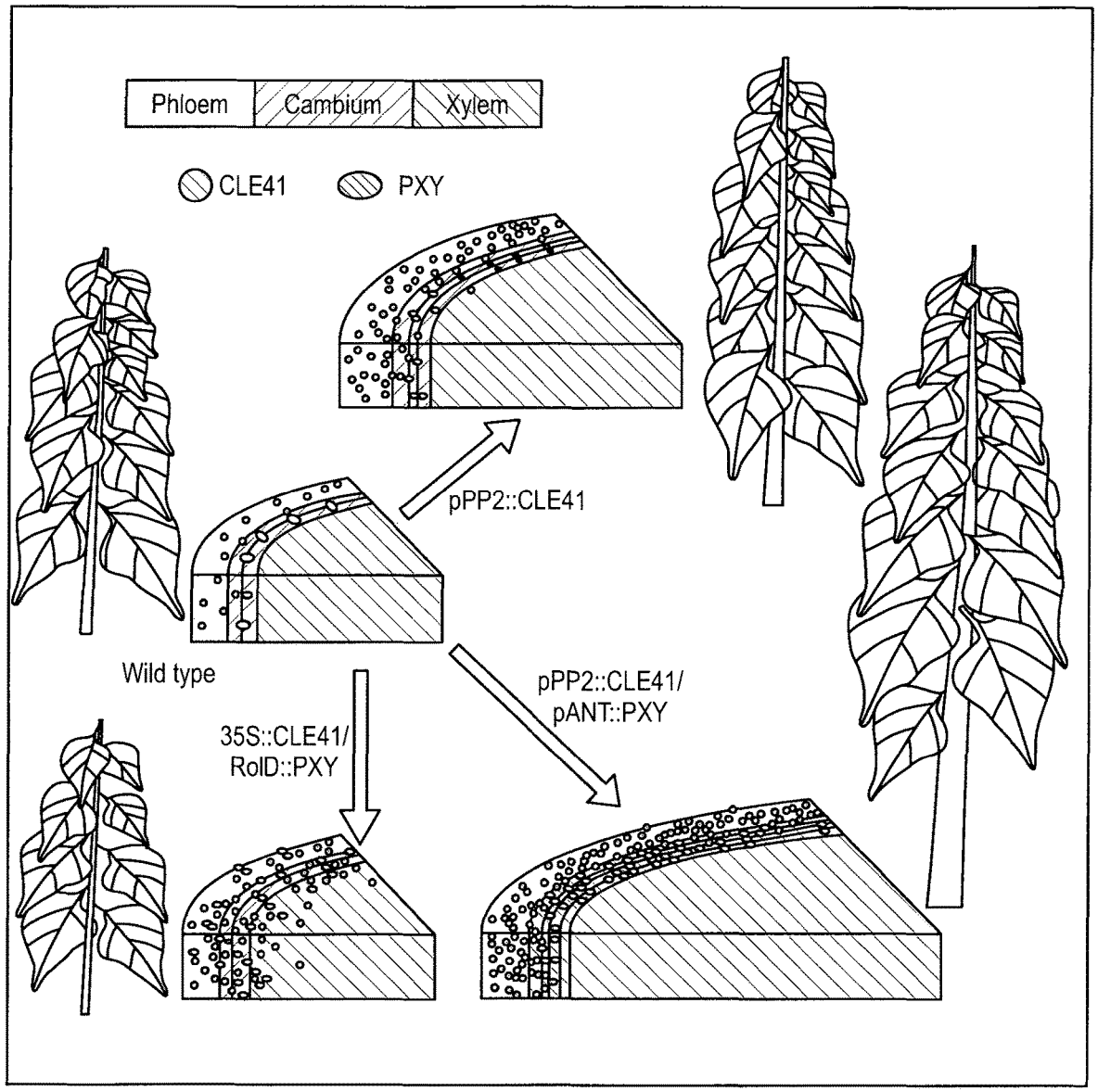
FIG. 12 is a pictorial representation of the effects of the present invention.

To better understand the cause of the increases in stem diameter in PtPP2::PttCLE41-PttANT::PttPXY lines, at 33 weeks half of the trees from each line were harvested and sectioned for stem material in order to perform cell counts for each line as described in FIG. 10. In order to examine material from a similar developmental stage and to account for the differing sizes of the trees examined, the analysis was carried out on material from the 50th internode. A dramatic increase in xylem cell numbers was observed, that correlated with the increase in stem diameter with PtPP2::PttCLE41-PttANT::PttPXY lines having the largest number of xylem cells, 189% that of control plants (FIG. 3F). Within individual lines there was also a correlation between cell numbers and PttCLE41 expression and to a lesser extent with PttPXY expression (FIG. 11). To determine whether it was possible to increase wood formation without altering xylem morphology, Cellprofiler was adapted (Carpenter et al. (2006) supra) to measure a number of morphological characteristics of the xylem (FIG. 10). The analysis revealed no significant differences in average cell size, average cell lumen size, average cell wall area and vessel numbers as a proportion of total xylem cells in PtPP2::PttCLE41-PttANT::PttPXY compared to controls lines (Table 1) indicating that the increased wood production did not alter wood morphology.

TABLE 1

Analysis of transverse section of xylem from the 50th internode of control and PtPP2::CLE41-PttANT::PXY plants. Mean of 5 independent lines are shown with the standard error. Area measurements are in arbitrary units. Statistical analysis was carried out using a T-test, no significant differences were found.

| | Control | PtPP2::CLE41-PttANT::PXY |
|---|---|---|
| Average cell size | 607 ± 13 | 577 ± 19 |
| Average lumen size | 312 ± 13 | 346 ± 9 |
| Average cell wall area | 265 ± 24 | 260 ± 16 |
| Vessels per 1000 cells | 50 ± 2 | 49 ± 6 |

To determine whether the improved growth characteristics led to increased woody biomass, the remaining trees were allowed to grow for a further 6 month period after which we determined dry weight (FIG. 3G) and wet weight (FIG. 9) at various points along the stem. Consistent with previous observations, measurement at the base, 50th internode (middle) and at the top of the stem demonstrated that PtPP2::PttCLE41-PttANT::PttPXY lines exhibited significant increases in dry weight in comparison to other lines used in this study. In particular, at the middle and base of trees, the dry weight of PtPP2::PttCLE41-PttANT::PttPXY stem segments were on average more than twice the weight of the control plants.

Figure 4:
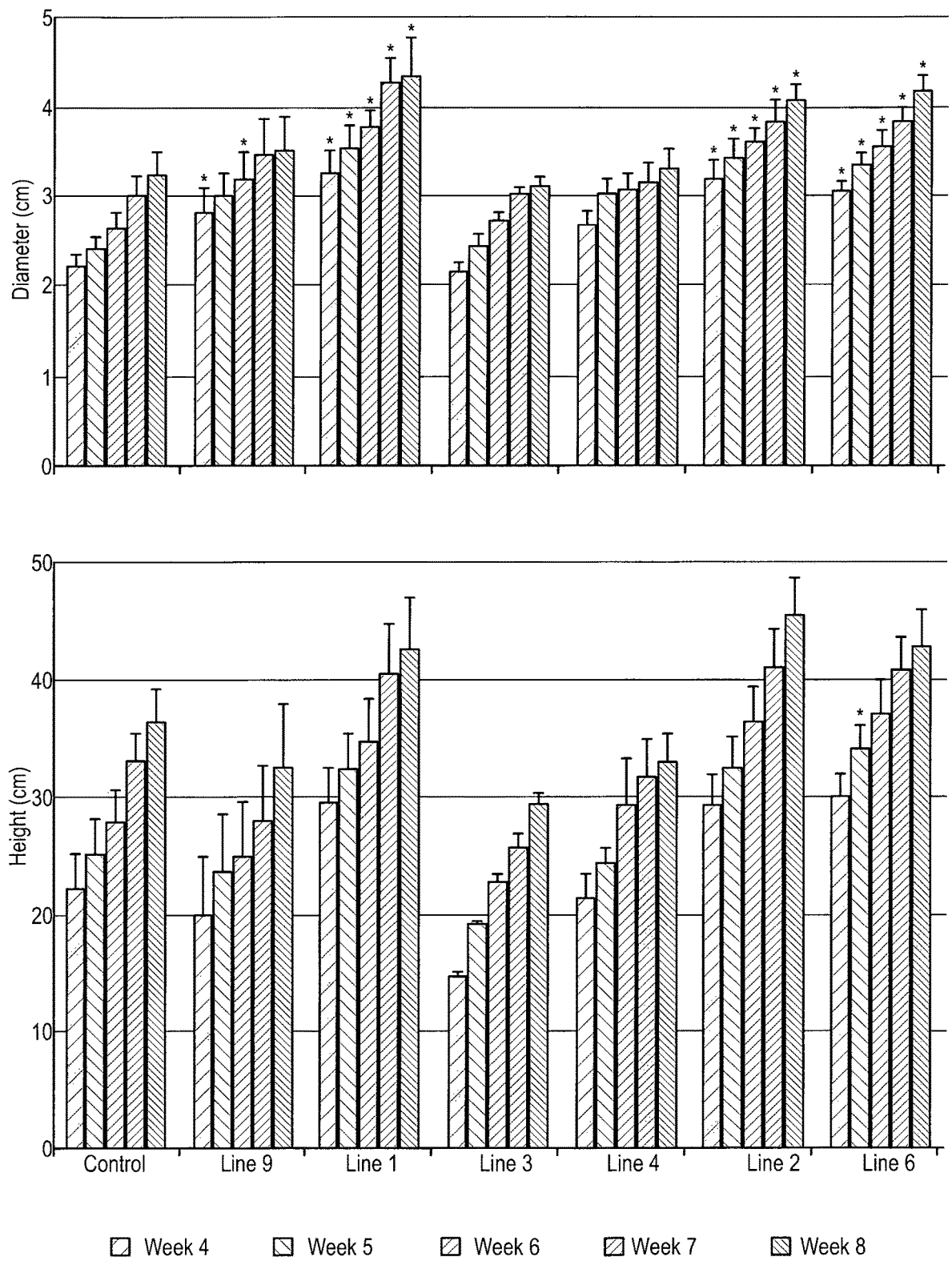
FIG. 4 shows the growth of clonally propagated plants derived from independent transformants of PtPP2::PttCLE41-PttANT::PttPXY. Diameter (top) and height (bottom) of plants was measured at weekly intervals starting 4 weeks after transfer from tissue culture to soil. Asterisk indicates a p value of less than 0.05 compared to the controls. All p values were calculated with an ANOVA and a LSD post-hoc test, n=6 for the control; n=5 for PtPP2::PttCLE41-PttANT::PttPXY lines 1, 3 and 9; n=4 for lines 2 and 4.

In order to ensure that the differences observed were reproducible, material from six independent PtPP2::PttCLE41-PttANT::PttPXY lines was clonally propagated. The growth of these plants was monitored weekly, starting shortly after transfer to soil. The diameter of several clones was significantly bigger than wild type at all stages monitored (FIG. 4). There was also variation between clones such that plants from line 2 were both significantly taller and exhibited a significantly larger diameter than plants from line 3 at all 5 time points examined (FIG. 4).

CONCLUSIONS

Figure 9:
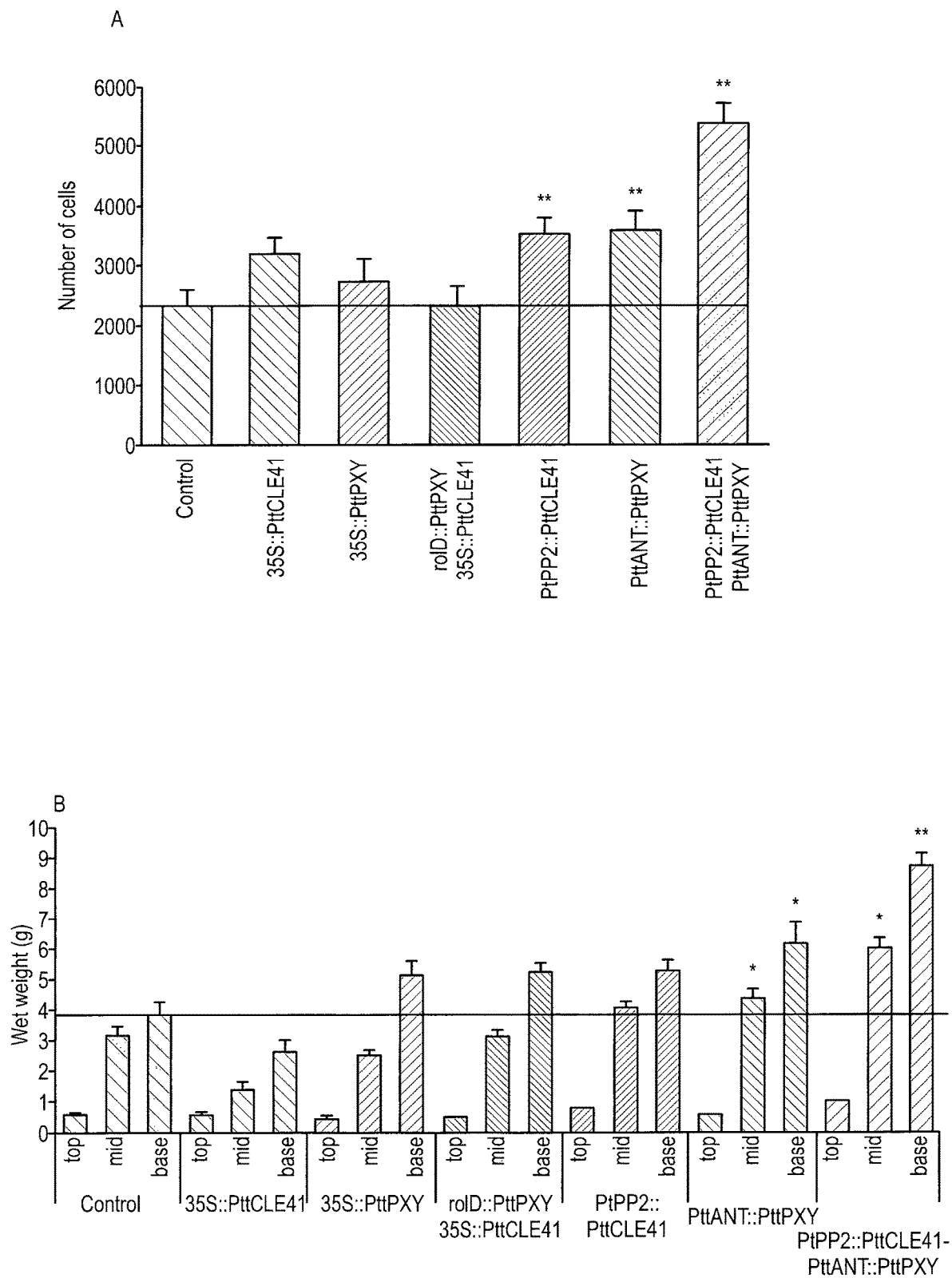
FIG. 9 shows xylem cell number and biomass of transgenic trees. (A) Graph showing number of vascular cells in control and 35S::PttCLE41, 35S::PttPXY, 35S::PttCLE41 rolD::PttPXY, PtPP2::PttCLE41, PttANT::PttPXY and PtPP2::PttCLE41 PttANT::PttPXY hybrid aspen lines in tissue culture 3 weeks postrooting. (B) Wet weight of 10 cm pieces of sapling stem taken from the base, middle (50th internode) and top, except for 35S::PttCLE41 that had less than 50 internodes and sections were taken midway between the top and bottom instead. Graph shows the wet weight of stem pieces in FIG. 3G. *Significantly larger than wild type p<0.05; ** Significantly larger than all other lines p<0.001; values were calculated with an ANOVA and LSD post-hoc test, N=7.

Trees represent a huge natural resource used for the production of paper, fuel and materials, and are an increasingly important carbon sink (Stephenson et al (2014) Nature 507, 90-93) that can help to ameliorate anthropogenic increases in atmospheric CO2. Recently, trees have also been the focus of intense interest as a renewable source of plant biomass that may be converted into bioethanol (Somerville et al (2006) Science 312, 1277) and other chemicals for the rapidly expanding field of industrial biotechnology (Raunikar et al (2010). Forest Policy and Economics 12, 48-56). The majority of biomass in trees is derived from radial growth that is characterised by growth rings in the wood. The size of each growth ring is intimately linked to the environmental conditions during the growing season that year. The data provided herein data suggests that the PXY-CLE pathway functions in trees to regulate secondary growth and is likely to be central to the way in which trees evolved secondary growth Together, the analysis demonstrates that by engineering the PXY-CLE pathway we were able to dramatically increase secondary growth in plants shortly after they were first rooted (FIG. 3 and FIG. 9), the earliest point they could be analysed, and the increase in xylem was maintained in plants grown for up to a year (FIG. 4 and FIG. 9). These results indicate that this pattern of growth continues during the lifetime of the tree, thereby providing a means of dramatically increasing tree productivity that would help to meet the increasing demand for renewable resources. While tree productivity may benefit from anthropogenic increases in atmospheric CO2, climate models and recent changes in weather pattern strongly suggest that we are entering a period in which large parts of the globe experience more frequent exposure to extreme and changeable weather (Palmer, et al (2014) Science 344, 803-804) that is likely to have detrimental effects on growth. It will be important to establish whether manipulating PXY-CLE signalling will enable us override the environmental cues that normally regulate plant growth and so enable us to generate trees that are able to maintain high productivity even when exposed to more extreme environmental conditions.

Sequence Listing Table

Figure 13A:
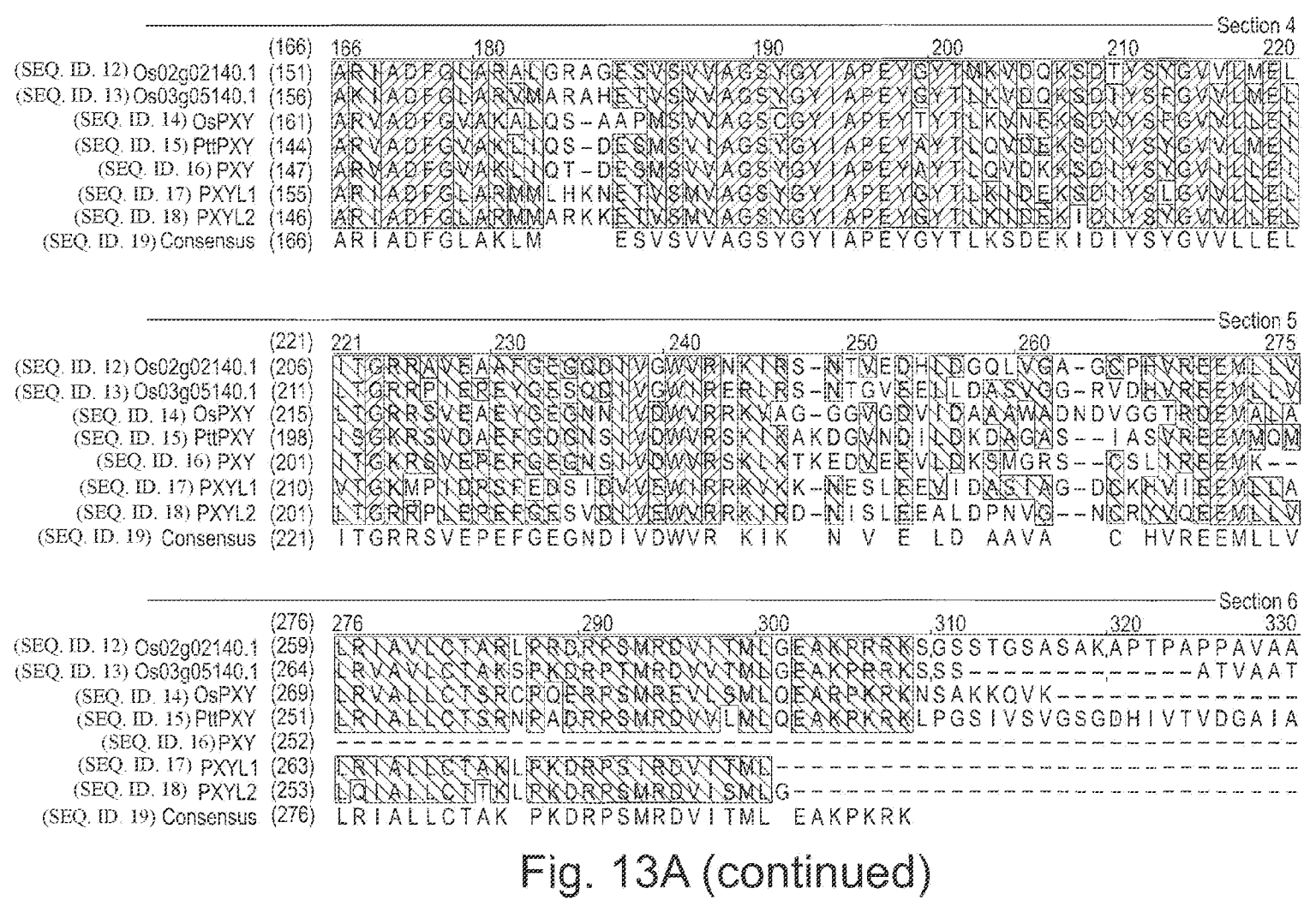

| SEQUENCE NUMBER | ORGANISM | TYPE OF SEQUENCE | Gene/Protein | FIGURE NUMBER | Previous SEQ ID NO: |
|---|---|---|---|---|---|
| SEQ ID NO: 1 | Arabidopsis thaliana | Protein | CLE41 | FIG. 5 B and 14 B | 3 |
| SEQ ID NO: 2 | Arabidopsis thaliana | DNA | CLE41 | FIG. 14 B | 22 |
| SEQ ID NO: 3 | Populus trichocarpo | Protein | CLE41 | FIG. 5 B | — |
| SEQ ID NO: 4 | Populus tremula x Populus tremuloides | Protein | CLE41 | FIG. 5 B and FIG. 14 C | — |
| SEQ ID NO: 5 | Populus tremula x Populus tremuloides | DNA | CLE41 | FIG. 14 C | — |
| SEQ ID NO: 6 | Arabidopsis thaliana | Protein | PXY | FIG. 5 A and FIG. 13 C | 25 |
| SEQ ID NO: 7 | Arabidopsis thaliana | DNA | PXY Without introns | FIG. 13 C | 26 |
| SEQ ID NO: 8 | Arabidopsis thaliana | DNA | PXY With introns | FIG. 13 C | 27 |
| SEQ ID NO: 9 | Populus tremula x Populus tremuloides | Protein | PXY | FIG. 5A and FIG. 13 B | — |
| SEQ ID NO: 10 | Populus tremula x Populus tremuloides | DNA | PXY | FIG. 13 B | — |
| SEQ ID NO: 11 | Populus trichocarpo | Protein | PXY | FIG. 5 A | — |
| SEQ ID NO: 12 | Oryza sativa | Protein | PXY | FIG. 13 A | 13 |
| SEQ ID NO: 13 | Oryza sativa | Protein | PXY | FIG. 13 A | 14 |
| SEQ ID NO: 14 | Oryza sativa | Protein | PXY | FIG. 13 A | 15 |
| SEQ ID NO: 15 | Populus tremula x Populus tremuloides | Protein | PXY | FIG. 13 A | 16 |
| SEQ ID NO: 16 | Populus tremula x Populus tremuloides | Protein | PXY | FIG. 13 A | 17 |
| SEQ ID NO: 17 | Populus tremula x Populus tremuloides | Protein | PXL1 | FIG. 13A | 18 |
| SEQ ID NO: 18 | Populus tremula x Populus tremuloides | Protein | PXL2 | FIG. 13 A | 19 |
| SEQ ID NO: 19 | Artificial Sequence | Protein | Consensus | FIG. 13 A | 20 |
| SEQ ID NO: 20 | Artificial Sequence | DNA | Primer | | |
| SEQ ID NO: 21 | Artificial Sequence | DNA | Primer | | |
| SEQ ID NO: 22 | Artificial Sequence | DNA | Primer | | |
| SEQ ID NO: 23 | Artificial Sequence | DNA | Primer | | |
| SEQ ID NO: 24 | Artificial Sequence | DNA | Primer | | |
| SEQ ID NO: 25 | Artificial Sequence | DNA | Primer | | |
| SEQ ID NO: 26 | Artificial Sequence | DNA | Primer | | |
| SEQ ID NO: 27 | Artificial Sequence | DNA | Primer | | |
| SEQ ID NO: 28 | Arabidopsis thaliana | Protein | CLE42 | FIG. 15 A | |
| SEQ ID NO: 29 | Arabidopsis thaliana | DNA | CLE42 | FIG. 15 B | |

The invention claimed is:

1. A method for manipulating the growth and/or structure of a plant comprising modifying the plant to specifically increase the expression and/or activity of PXY in the vascular tissue of the plant compared to the expression and/or activity of PXY in the vascular tissue of a wild type plant of the same species maintained under identical conditions, the process comprising:

introducing into the plant a regulatory element which specifically directs expression of PXY in the vascular tissue of the plant, wherein expression and/or activity of PXY in the non-vascular tissue of the plant remains unaltered compared to the expression and/or activity of PXY in the vascular tissue of the plant, wherein the regulatory element comprises an ANT promoter sequence produced by using the primer sequences of SEQ. ID. NO. 21 and SEQ ID NO: 22, and wherein the PXY comprises the polypeptide sequence of SEQ ID NO: 19.

2. The method according to claim 1 comprising specifically increasing the expression and/or activity of PXY in the cambium of the plant.

3. The method according to claim 1 wherein the promoter is derived from hybrid aspen.

4. The method according to claim 1 wherein the regulatory element is provided in an expression cassette operably linked to a nucleic acid molecule encoding PXY.

5. The method according to claim 4 wherein the regulatory element is provided in an expression cassette which comprises sequences for insertion of the regulatory element into the plant genome, operably linked to the native PXY gene.

6. The method according to claim 4, wherein the expression cassette is provided in a vector.

7. The method according to claim 6 wherein the vector is capable of propagating in both a bacterial host cell and a plant cell.

8. The method according to claim 6, further comprising the step of introducing the expression cassette or vector into a plant cell.

9. The method according to claim 6 further comprising measuring expression of PXY by measuring the relative amounts of the gene product in a cell or tissue extracted from the modified plant and comparing it to the level of said gene product in a corresponding cell or tissue from a wild type plant of the same species maintained under identical conditions.

10. The method according to claim 1 wherein the levels of PXY are increased by at least about 20% compared to the level of PXY in a wild type plant maintained under identical conditions.

11. The method according to claim 1 wherein the activity of PXY is increased by at least about 5% compared to the activity of PXY in a wild type plant maintained under identical conditions.

12. The method according to claim 9 comprising measuring increased growth by measuring radial diameter, vigour, growth rate, the amount of leaf tissue, the amount of biomass, and/or seed yield in the modified plant comparing it to the corresponding phenotype in a corresponding cell or tissue from a wild type plant.

13. The method according to claim 12 wherein increased growth is at least about 20% increase in radial diameter, vigour, growth rate, the amount of leaf tissue, the amount of biomass, and/or seed yield as compared to a wild type plant maintained under identical conditions.

* * * * *

SEQUENCE LISTING

<160> NUMBER OF SEQ ID NOS: 39

<210> SEQ ID NO 1
<211> LENGTH: 99
<212> TYPE: PRT
<213> ORGANISM: Arabidopsis thaliana

<400> SEQUENCE: 1

Met Ala Thr Ser Asn Asp Gln Thr Asn Thr Lys Ser Ser His Ser Arg
1               5                   10                  15

Thr Leu Leu Leu Leu Phe Ile Phe Leu Ser Leu Leu Leu Phe Ser Ser
            20                  25                  30

Leu Thr Ile Pro Met Thr Arg His Gln Ser Thr Ser Met Val Ala Pro
        35                  40                  45

Phe Lys Arg Val Leu Leu Glu Ser Ser Val Pro Ala Ser Ser Thr Met
    50                  55                  60

Asp Leu Arg Pro Lys Ala Ser Thr Arg Arg Ser Arg Thr Ser Arg Arg
65                  70                  75                  80

Arg Glu Phe Gly Asn Asp Ala His Glu Val Pro Ser Gly Pro Asn Pro
                85                  90                  95

Ile Ser Asn

<210> SEQ ID NO 2
<211> LENGTH: 300
<212> TYPE: DNA
<213> ORGANISM: Arabidopsis thaliana

<400> SEQUENCE: 2
atggcaacat caaatgacca aaccaatact aaatcatcac attctcgtac tcttctcctt      60
ctcttcatct tcttatccct ccttctcttc agtagcctta caatccccat gactcgtcat     120
cagtccacat ctatggttgc tcccttcaag agggttctcc tcgaatcttc agttccagct     180
tcatcaacaa tggatctacg tccaaaggct agcacacgac gcagccgcac ttctagaagg     240
agagagtttg gaaatgatgc tcatgaggtt cctagtggtc caaaccctat ttccaactag     300

<210> SEQ ID NO 3
<211> LENGTH: 116
<212> TYPE: PRT
<213> ORGANISM: Populus trichocarpa

<400> SEQUENCE: 3

Met Ala Thr Pro Lys Thr Gln Ser Thr Thr Ile Ser Asp His Gln Thr
1               5                   10                  15

Cys Thr Lys Ala His His Phe Leu Ser Leu Leu Ala Leu Leu Phe Ile
            20                  25                  30

Phe Ile Leu Leu Thr Thr Ser Thr Lys Pro Ile Asn Pro Thr Asn Met
        35                  40                  45

Ala Ala Ser Ile Ser Ile Lys Arg Leu Leu Leu Glu Ser Ser Glu Pro
    50                  55                  60

Ala Ser Thr Thr Met Asn Leu His Pro Lys Gln Thr Gln Asp Ala Arg
65                  70                  75                  80

Thr Ser Ser Ser Ser Ser Ser Ser Thr Ser Ser Ser Lys Ser Thr Arg
                85                  90                  95

Thr Lys Phe Gly Ala Ala Ala His Glu Val Pro Ser Gly Pro Asn Pro
            100                 105                 110

Ile Ser Asn Arg
        115

<210> SEQ ID NO 4
<211> LENGTH: 115
<212> TYPE: PRT
<213> ORGANISM: Populus tremula x Populus tremuloides

<400> SEQUENCE: 4

```
Met Ala Thr Pro Lys Thr Gln Ser Arg Thr Ile Ser Asp His Gln Thr
1               5                   10                  15

Cys Thr Lys Ala His His Phe Leu Ser Leu Leu Ala Leu Leu Phe Ile
            20                  25                  30

Phe Ile Leu Leu Thr Thr Ser Thr Lys Pro Ile Asn Pro Thr Asn Met
        35                  40                  45

Ala Ala Ser Ile Ser Ile Lys Arg Leu Leu Leu Glu Ser Ser Glu Pro
    50                  55                  60

Ala Ser Thr Thr Met Asn Leu His Pro Lys Gln Asn Gln Asp Ala Arg
65                  70                  75                  80

Thr Ser Ser Ser Ser Ser Ser Thr Ser Ser Lys Ser Thr Arg Thr
                85                  90                  95

Lys Ser Gly Ala Ala Ala His Glu Val Pro Ser Gly Pro Asn Pro Ile
            100                 105                 110

Ser Asn Arg
        115
```

<210> SEQ ID NO 5
<211> LENGTH: 664
<212> TYPE: DNA
<213> ORGANISM: Populus tremula x Populus tremuloides

<400> SEQUENCE: 5

```
tagctagcct tggtgctggt tcatggatat tgcaccctct tgggctcttg ggggtggttt      60
ctttcgtcta ttaactgcat ggcaacacca aaaacacaat caaggacaat cagtgatcat     120
caaacatgca caaaagcaca ccatttcctt tcattgcttg cacttctttt cattttatt     180 ttactcacta cctccaccaa acccataaac ccaacaaata tggcggcatc gatttccatc     240
aaaaggcttc tattagaatc ctcagagcca gcctctacta ccatgaactt gcatccaaaa     300
caaaaccaag acgcacgtac ttcttcttct tcttcttcca cctcatcatc aaaatctacg     360
cgtaccaagt ctggagctgc tgctcatgaa gttcctagcg gtccaaaccc tatttcaaac     420
aggtaaataa gttgatatat caatgatgaa gcacagaaaa ctcgtactgc ccttgagagc     480
cggttgttga agatgatagc tagagagttg taacggtgaa gttaattacg agtttgtcat     540
ctttattgtt attgttttg tgcaccatta atactgcttg tcctcagtga gagggttctt      600
accttcttgt tatgtcatca atctcagcct tacttctttc tttcttctt tttcgtgct      660 tgtt                                                                 664
```

<210> SEQ ID NO 6
<211> LENGTH: 1041
<212> TYPE: PRT
<213> ORGANISM: Arabidopsis thaliana

<400> SEQUENCE: 6

```
Met Lys Lys Lys Asn Ile Ser Pro Ser Leu Val Leu His Pro Leu Leu
1               5                   10                  15

Leu Leu Leu Leu Pro Phe Phe Ala Phe Asn Ser Leu Ala Leu Lys Phe
            20                  25                  30
```

```
Ser Pro Gln Leu Leu Ser Leu Leu Ser Leu Lys Thr Ser Leu Ser Gly
         35                  40                  45

Pro Pro Ser Ala Phe Gln Asp Trp Lys Val Pro Val Asn Gly Gln Asn
 50                  55                  60

Asp Ala Val Trp Cys Ser Trp Ser Gly Val Val Cys Asp Asn Val Thr
 65                  70                  75                  80

Ala Gln Val Ile Ser Leu Asp Leu Ser His Arg Asn Leu Ser Gly Arg
                 85                  90                  95

Ile Pro Ile Gln Ile Arg Tyr Leu Ser Ser Leu Leu Tyr Leu Asn Leu
            100                 105                 110

Ser Gly Asn Ser Leu Glu Gly Ser Phe Pro Thr Ser Ile Phe Asp Leu
            115                 120                 125

Thr Lys Leu Thr Thr Leu Asp Ile Ser Arg Asn Ser Phe Asp Ser Ser
130                 135                 140

Phe Pro Pro Gly Ile Ser Lys Leu Lys Phe Leu Lys Val Phe Asn Ala
145                 150                 155                 160

Phe Ser Asn Asn Phe Glu Gly Leu Leu Pro Ser Asp Val Ser Arg Leu
                165                 170                 175

Arg Phe Leu Glu Glu Leu Asn Phe Gly Gly Ser Tyr Phe Glu Gly Glu
            180                 185                 190

Ile Pro Ala Ala Tyr Gly Gly Leu Gln Arg Leu Lys Phe Ile His Leu
            195                 200                 205

Ala Gly Asn Val Leu Gly Gly Lys Leu Pro Arg Leu Gly Leu Leu
            210                 215                 220

Thr Glu Leu Gln His Met Glu Ile Gly Tyr Asn His Phe Asn Gly Asn
225                 230                 235                 240

Ile Pro Ser Glu Phe Ala Leu Leu Ser Asn Leu Lys Tyr Phe Asp Val
                245                 250                 255

Ser Asn Cys Ser Leu Ser Gly Ser Leu Pro Gln Glu Leu Gly Asn Leu
            260                 265                 270

Ser Asn Leu Glu Thr Leu Phe Leu Phe Gln Asn Gly Phe Thr Gly Glu
            275                 280                 285

Ile Pro Glu Ser Tyr Ser Asn Leu Lys Ser Leu Lys Leu Leu Asp Phe
            290                 295                 300

Ser Ser Asn Gln Leu Ser Gly Ser Ile Pro Ser Gly Phe Ser Thr Leu
305                 310                 315                 320

Lys Asn Leu Thr Trp Leu Ser Leu Ile Ser Asn Asn Leu Ser Gly Glu
                325                 330                 335

Val Pro Glu Gly Ile Gly Glu Leu Pro Glu Leu Thr Thr Leu Phe Leu
            340                 345                 350

Trp Asn Asn Asn Phe Thr Gly Val Leu Pro His Lys Leu Gly Ser Asn
            355                 360                 365

Gly Lys Leu Glu Thr Met Asp Val Ser Asn Asn Ser Phe Thr Gly Thr
            370                 375                 380

Ile Pro Ser Ser Leu Cys His Gly Asn Lys Leu Tyr Lys Leu Ile Leu
385                 390                 395                 400

Phe Ser Asn Met Phe Glu Gly Glu Leu Pro Lys Ser Leu Thr Arg Cys
                405                 410                 415

Glu Ser Leu Trp Arg Phe Arg Ser Gln Asn Asn Arg Leu Asn Gly Thr
            420                 425                 430

Ile Pro Ile Gly Phe Gly Ser Leu Arg Asn Leu Thr Phe Val Asp Leu
            435                 440                 445

Ser Asn Asn Arg Phe Thr Asp Gln Ile Pro Ala Asp Phe Ala Thr Ala
```

```
                450             455             460
        Pro Val Leu Gln Tyr Leu Asn Leu Ser Thr Asn Phe His Arg Lys
        465                 470                 475                 480

Leu Pro Glu Asn Ile Trp Lys Ala Pro Asn Leu Gln Ile Phe Ser Ala
                        485                 490                 495

Ser Phe Ser Asn Leu Ile Gly Glu Ile Pro Asn Tyr Val Gly Cys Lys
                    500                 505                 510

Ser Phe Tyr Arg Ile Glu Leu Gln Gly Asn Ser Leu Asn Gly Thr Ile
                    515                 520                 525

Pro Trp Asp Ile Gly His Cys Glu Lys Leu Leu Cys Leu Asn Leu Ser
                530                 535                 540

Gln Asn His Leu Asn Gly Ile Ile Pro Trp Glu Ile Ser Thr Leu Pro
        545                 550                 555                 560

Ser Ile Ala Asp Val Asp Leu Ser His Asn Leu Leu Thr Gly Thr Ile
                        565                 570                 575

Pro Ser Asp Phe Gly Ser Ser Lys Thr Ile Thr Thr Phe Asn Val Ser
                    580                 585                 590

Tyr Asn Gln Leu Ile Gly Pro Ile Pro Ser Gly Ser Phe Ala His Leu
                    595                 600                 605

Asn Pro Ser Phe Phe Ser Ser Asn Glu Gly Leu Cys Gly Asp Leu Val
                610                 615                 620

Gly Lys Pro Cys Asn Ser Asp Arg Phe Asn Ala Gly Asn Ala Asp Ile
        625                 630                 635                 640

Asp Gly His His Lys Glu Glu Arg Pro Lys Lys Thr Ala Gly Ala Ile
                        645                 650                 655

Val Trp Ile Leu Ala Ala Ala Ile Gly Val Gly Phe Phe Val Leu Val
                    660                 665                 670

Ala Ala Thr Arg Cys Phe Gln Lys Ser Tyr Gly Asn Arg Val Asp Gly
                    675                 680                 685

Gly Gly Arg Asn Gly Gly Asp Ile Gly Pro Trp Lys Leu Thr Ala Phe
                690                 695                 700

Gln Arg Leu Asn Phe Thr Ala Asp Asp Val Val Glu Cys Leu Ser Lys
        705                 710                 715                 720

Thr Asp Asn Ile Leu Gly Met Gly Ser Thr Gly Thr Val Tyr Lys Ala
                        725                 730                 735

Glu Met Pro Asn Gly Glu Ile Ile Ala Val Lys Lys Leu Trp Gly Lys
                    740                 745                 750

Asn Lys Glu Asn Gly Lys Ile Arg Arg Arg Lys Ser Gly Val Leu Ala
                    755                 760                 765

Glu Val Asp Val Leu Gly Asn Val Arg His Arg Asn Ile Val Arg Leu
                770                 775                 780

Leu Gly Cys Cys Thr Asn Arg Asp Cys Thr Met Leu Leu Tyr Glu Tyr
        785                 790                 795                 800

Met Pro Asn Gly Ser Leu Asp Asp Leu Leu His Gly Gly Asp Lys Thr
                        805                 810                 815

Met Thr Ala Ala Ala Glu Trp Thr Ala Leu Tyr Gln Ile Ala Ile Gly
                    820                 825                 830

Val Ala Gln Gly Ile Cys Tyr Leu His His Asp Cys Asp Pro Val Ile
                    835                 840                 845

Val His Arg Asp Leu Lys Pro Ser Asn Ile Leu Leu Asp Ala Asp Phe
                850                 855                 860

Glu Ala Arg Val Ala Asp Phe Gly Val Ala Lys Leu Ile Gln Thr Asp
        865                 870                 875                 880
```

```
Glu Ser Met Ser Val Ala Gly Ser Tyr Gly Tyr Ile Ala Pro Glu
            885                 890                 895

Tyr Ala Tyr Thr Leu Gln Val Asp Lys Lys Ser Asp Ile Tyr Ser Tyr
        900                 905                 910

Gly Val Ile Leu Leu Glu Ile Ile Thr Gly Lys Arg Ser Val Glu Pro
        915                 920                 925

Glu Phe Gly Glu Gly Asn Ser Ile Val Asp Trp Val Arg Ser Lys Leu
    930                 935                 940

Lys Thr Lys Glu Asp Val Glu Val Leu Asp Lys Ser Met Gly Arg
945                 950                 955                 960

Ser Cys Ser Leu Ile Arg Glu Glu Met Lys Gln Met Leu Arg Ile Ala
            965                 970                 975

Leu Leu Cys Thr Ser Arg Ser Pro Thr Asp Arg Pro Pro Met Arg Asp
        980                 985                 990

Val Leu Leu Ile Leu Gln Glu Ala  Lys Pro Lys Arg Lys  Thr Val Gly
        995                 1000                1005

Asp Asn  Val Ile Val Val Gly  Asp Val Asn Asp Val  Asn Phe Glu
    1010                1015                1020

Asp Val  Cys Ser Val Asp Val  Gly His Asp Val Lys  Cys Gln Arg
    1025                1030                1035

Ile Gly  Val
    1040

<210> SEQ ID NO 7
<211> LENGTH: 3126
<212> TYPE: DNA
<213> ORGANISM: Arabidopsis thaliana

<400> SEQUENCE: 7
atgaaaaaga agaacatttc tccttctctt gttcttcatc cccttctcct tcttctactt      60
cctttctttg ctttcaattc cttagctctc aagttttcac ctcaactctt gtctctcctt    120
tcccttaaaa catctctctc tggccctccc tctgcctttc aagactggaa agtccccgtt    180
aacggtcaaa acgacgccgt ttggtgttct tggtccggtg tagtctgtga taatgtaacg    240
gctcaagtca tttccctcga cctctctcac cggaacctct ctggtcgtat tcctatacag    300
attcgttact tgtcgagctt actctactta aatctcagtg ggaattcttt ggaaggttcg    360
tttccaactt ctatctttga tctcaccaag ctcactaccc tcgacatcag ccgtaactcg    420
ttcgactcga gttttcctcc cggaatctcc aagcttaagt tcttaaaagt cttcaatgcg    480
ttcagcaaca acttcgaagg tctattacct agtgacgtgt ctcgtcttcg tttcttggaa    540
gagcttaact tggtggaag ttactttgaa ggagagattc cagcagctta cggtggttta    600
cagagattga agtttattca tttagctgga aatgtcctcg gaggtaaact acctcctaga    660
ttaggactct aacagagct ccaacacatg gaaatcggtt ataatcactt caacggaaac    720
ataccttcgg agtttgcctt actctcaaat ctcaagtact tgacgtttc caattgcagc    780
ctctctggtt ctctgcctca agaactcggg aatctctcaa acctagagac tttatttcta    840
ttccaaaacg gttcaccgg tgaaatccca gagagttata gcaacttgaa atccctcaag    900
cttctcgatt tttcgagtaa tcagctttct ggtagtatcc catcaggctt ctcgaccttg    960
aagaacctca catggctaag cttaatcagc aataacctct caggtgaagt acctgaagga   1020
atcggtgaac tccctgagct tactacattg tttctatgga caataacttt caccggagtt   1080
ttgccacaca agcttggatc aaacggtaaa cttgagacaa tggacgtctc taacaattca   1140
```

```
ttcaccggaa caatcccttc ttctctctgc catggaaaca agctatacaa actcatcctc    1200
ttctccaaca tgtttgaagg tgagctacca aagagcttga ctcgttgcga atctctatgg    1260
cggtttcgga gtcaaaacaa tcgattaaac ggcacaattc cgatcggatt cggctctcta    1320
cgtaacctca ctttcgttga tttaagcaac aacagattca ccgatcaaat tccggcggat    1380
ttcgccaccg ctcctgttct tcagtacttg aatctctcaa ccaatttctt ccacaggaaa    1440
ctaccggaaa acatatggaa agctccgaat ctacagatct tctcagcgag tttcagcaat    1500
ttgatcggtg aaatcccaaa ttacgttgga tgcaaaagct tctacaggat tgaactacaa    1560
ggaaactcac tcaacggaac gattccatgg gacatcggac attgcgagaa gcttctctgt    1620
ttgaatctca gccaaaatca tctcaacgga atcattccat gggagatttc aactcttccg    1680
tcaatcgccg acgtagatct ttctcataat ctcttaaccg gaacaatccc ttccgatttc    1740
ggaagctcta agacgatcac aaccttcaac gtttcgtata atcagctaat cggtccgatt    1800
ccaagtggtt ctttcgctca tctgaatccg tcgttcttct cctcaaacga aggactctgt    1860
ggagatctcg tcggaaaacc ttgcaattct gataggttta acgccggaaa tgcagatata    1920
gacggtcatc ataaagagga acgacctaag aaaacagccg gagctattgt ttggatattg    1980
gcggcggcga ttggggttgg attcttcgtc cttgtagccg ccactagatg cttccagaaa    2040
agctacggaa acagagtcga cggtggtgga agaaacggcg gagatatagg accgtggaag    2100
ctaacggctt ttcagagact aaacttcacg gcggatgatg tggttgagtg tctctcaaag    2160
actgataaca tcctcggaat gggatcaaca ggaacagtgt acaaagcaga gatgcctaat    2220
ggagaaataa tcgccgtgaa aaaactttgg ggaaaaaaca aagagaacgg caaaatccgg    2280
cggcggaaga gcggcgtatt ggcggaggtt gatgttctag gaacgtacg tcaccggaac    2340 atcgttcgtc tccttggatg ttgcacgaat cgagattgca cgatgctttt atacgaatac    2400
atgcctaatg gaagcttaga cgatcttctt cacggtgggg ataagacgat gaccgcggcg    2460
gcggaatgga cggctttgta tcagatcgcg attggagtgg ctcaagggat ctgttatctc    2520
caccatgatt gtgatccggt gattgtacac cgtgacctga aacctagcaa tatcctcctc    2580
gacgccgatt tcgaggcgcg tgtggcggac ttcgcgtcg cgaagcttat tcaaaccgac    2640
gaatccatgt ccgtcgtcgc cggttcgtac ggttacattg caccagaata tgcttacact    2700
ttacaagtgg ataaaaagag tgatatctat agctatgagt gattttatt agagataatc    2760 accggaaaaa gatcggtgga accggaattt ggagaaggta acagtatcgt ggattgggtt    2820
agatcaaagt tgaagacgaa agaagatgta gaagaagttc tagacaaaag catgggtagg    2880
tcgtgtagtc ttataagaga agagatgaaa caaatgttga gaattgcgtt gttgtgtaca    2940
agccggagtc cgacagacag accgccgatg agagatgtgt tgttgattct tcaagaggca    3000
aagccaaaga ggaagacagt aggggataat gtgatcgtcg ttggtgatgt taatgatgtc    3060
aatttcgaag atgtttgtag tgttgatgtt ggtcatgatg ttaaatgtca aaggattggg    3120
gtgtga                                                              3126
```

<210> SEQ ID NO 8
<211> LENGTH: 3302
<212> TYPE: DNA
<213> ORGANISM: Arabidopsis thaliana

<400> SEQUENCE: 8

```
atgaaaaaga agaacatttc tccttctctt gttcttcatc cccttctcct tcttctactt      60
```

```
cctttctttg ctttcaattc cttagctctc aagttttcac ctcaactctt gtctctcctt    120
tcccttaaaa catctctctc tggccctccc tctgcctttc aagactggaa agtcccgtt     180 aacggtcaaa acgacgccgt ttggtgttct tggtccggtg tagtctgtga taatgtaacg    240
gctcaagtca tttccctcga cctctctcac cggaacctct ctggtcgtat tcctatacag    300
attcgttact tgtcgagctt actctactta aatctcagtg ggaattcttt ggaaggttcg    360
tttccaactt ctatctttga tctcaccaag ctcactaccc tcgacatcag ccgtaactcg    420
ttcgactcga gttttcctcc cggaatctcc aagcttaagt tcttaaaagt cttcaatgcg    480
ttcagcaaca acttcgaagg tctattacct agtgacgtgt ctcgtcttcg tttcttggaa    540
gagcttaact ttggtggaag ttactttgaa ggagagattc cagcagctta cggtggttta    600
cagagattga agtttattca tttagctgga aatgtcctcg gaggtaaact acctcctaga    660
ttaggactct taacagagct ccaacacatg gaaatcggtt ataatcactt caacggaaac    720 atacctttcgg agtttgcctt actctcaaat ctcaagtact ttgacgtttc caattgcagc    780
ctctctggtt ctctgcctca agaactcggg aatctctcaa acctagagac tttatttcta    840
ttccaaaacg gtttcaccgg tgaaatccca gagagttata gcaacttgaa atccctcaag    900
cttctcgatt tttcgagtaa tcagcttcct ggtagtatcc catcaggctt ctcgaccttg    960
aagaacctca catggctaag cttaatcagc aataacctct caggtgaagt acctgaagga    1020
atcggtgaac tccctgagct tactacattg tttctatgga caataacttc accggagtt    1080 ttgccacaca agcttggatc aaacggtaaa cttgagacaa tggacgtctc taacaattca    1140
ttcaccggaa caatcccttc ttctctctgc atggaaaaca agctatacaa actcatcctc    1200
ttctccaaca tgtttgaagg tgagctacca aagagcttga ctcgttgcga atctctatgg    1260
cggtttcgga gtcaaaacaa tcgattaaac ggcacaattc cgatcggatt cggctctcta    1320
cgtaacctca ctttcgttga tttaagcaac aacagattca ccgatcaaat tccggcggat    1380
ttcgccaccg ctcctgttct tcagtacttg aatctctcaa ccaatttctt ccacaggaaa    1440
ctaccggaaa acatatggaa agctccgaat ctacagatct tctcagcgag tttcagcaat    1500
ttgatcggtg aaatcccaaa ttacgttgga tgcaaaagct tctacaggat tgaactacaa    1560
ggaaactcac tcaacggaac gattccatgg gacatcggac attgcgagaa gcttctctgt    1620
ttgaatctca gccaaaatca tctcaacgga atcattccat gggagatttc aactcttccg    1680
tcaatcgccg acgtagatct ttctcataat ctcttaaccg gaacaatccc ttccgatttc    1740
ggaagctcta agacgatcac aaccttcaac gtttcgtata atcagctaat cggtccgatt    1800
ccaagtggtt cttttcgctca tctgaatccg tcgttcttct cctcaaacga aggactctgt    1860
ggagatctcg tcgaaaaacc ttgcaattct gataggttta acgccggaaa tgcagatata    1920
gacggtcatc ataaagagga acgacctaag aaaacagccg gagctattgt ttggatattg    1980
gcggcggcga ttggggttgg attcttcgtc cttgtagccg ccactagatg cttccagaaa    2040
agctacggaa acagagtcga cggtggtgga agaaacggcg gagatatagg accgtggaag    2100
ctaacggctt ttcagagact aaacttcacg gcggatgatg tggttgagtg tctctcaaag    2160
actgataaca tcctccggaat gggatcaaca ggaacagtgt acaaagcaga gatgcctaat    2220
ggagaaataa tcgccgtgaa aaaactttgg ggaaaaaaca aagagaacgg caaaatccgg    2280
cggcggaaga gcggcgtatt ggcggaggtt gatgttctag ggaacgtacg tcaccggaac    2340
atcgttcgtc tccttggatg ttgcacgaat cgagattgca cgatgctttt atacgaatac    2400
atgcctaatg gaagcttaga cgatcttctt cacggtgggg ataagacgat gaccgcggcg    2460
```

```
gcggaatgga cggctttgta tcagatcgcg attggagtgg ctcaagggat ctgttatctc    2520
caccatgatt gtgatccggt gattgtacac cgtgacctga aacctagcaa tatcctcctc    2580
gacgccgatt tcgaggcgcg tgtggcggac ttcggcgtcg cgaagcttat tcaaaccgac    2640
gaatccatgt ccgtcgtcgc cggttcgtac ggttacattg caccaggtac ccttaacttt    2700
ttttgattat tctttacttt ccccaaattt taaattttgt actttttgt ccctttgttt     2760 ttattattcg aattttgtcc gtttgttaaa cattctttt  gttgggatga aacatctga     2820 caaatatgac taaaatttta attttgtttg ttttggttac agaatatgct tacactttac    2880
aagtggataa aaagagtgat atctatagct atggagtgat tttattagag ataatcaccg    2940
gaaaaagatc ggtggaaccg gaatttggag aaggtaacag tatcgtggat tgggttagat    3000
caaagttgaa gacgaaagaa gatgtagaag aagttctaga caaaagcatg ggtaggtcgt    3060
gtagtcttat aagagaagag atgaaacaaa tgttgagaat tgcgttgttg tgtacaagcc    3120
ggagtccgac agacagaccg ccgatgagag atgtgttgtt gattcttcaa gaggcaaagc    3180
caaagaggaa gacagtaggg gataatgtga tcgtcgttgg tgatgttaat gatgtcaatt    3240
tcgaagatgt ttgtagtgtt gatgttggtc atgatgttaa atgtcaaagg attggggtgt    3300
ga                                                                  3302
```

<210> SEQ ID NO 9
<211> LENGTH: 1026
<212> TYPE: PRT
<213> ORGANISM: Populus tremula x Populus tremuloides

<400> SEQUENCE: 9

Met Lys Leu Pro Phe Leu Phe Pro Leu Ala Phe Phe Tyr Leu
1               5                   10                  15

Phe Lys Pro Pro Leu Val Val Phe Ser Ala Thr Thr Leu Pro Pro Pro
                20                  25                  30

Leu Gln Ser Leu Leu Ser Ile Lys Thr Phe Leu Lys Asp Pro Ser Asn
            35                  40                  45

Thr Phe His Asp Trp Asn Leu Ser Asn Thr Ser Gly Leu Ile Gln Glu
        50                  55                  60

Pro Val Trp Cys Ser Trp Ser Gly Ile Lys Cys Asn Pro Ala Thr Ala
65                  70                  75                  80

Gln Ile Thr Ser Leu Asp Leu Ser His Arg Asn Leu Ser Gly Val Ile
                85                  90                  95

Pro Ala Glu Ile Arg Tyr Leu Thr Ser Leu Val His Leu Asn Leu Ser
            100                 105                 110

Gly Asn Ala Phe Asp Gly Leu Leu Gln Pro Ala Ile Phe Glu Leu Gly
        115                 120                 125

Asp Leu Arg Ile Leu Asp Ile Ser His Asn Asn Phe Asn Ser Thr Phe
    130                 135                 140

Pro Pro Gly Ile Ser Lys Leu Lys Phe Leu Arg Val Phe Asn Ala Tyr
145                 150                 155                 160

Ser Asn Asn Phe Thr Gly Pro Leu Pro Lys Glu Phe Val Trp Leu Arg
                165                 170                 175

Phe Leu Glu Glu Leu Ser Leu Gly Gly Ser Tyr Phe Thr Gly Glu Ile
            180                 185                 190

Pro Arg Ser Tyr Gly Ser Phe Leu Arg Leu Lys Tyr Leu His Leu Ala
        195                 200                 205

Gly Asn Glu Leu Glu Gly Pro Leu Pro Pro Asp Leu Gly Ser Leu Ser

-continued

```
              210                 215                 220
Gln Leu Glu His Leu Glu Leu Gly Tyr His Pro Leu Ser Gly Asn
225                 230                 235                 240

Val Pro Glu Glu Phe Ala Leu Leu Thr Asn Leu Lys Tyr Leu Asp Ile
            245                 250                 255

Ser Lys Cys Asn Leu Thr Gly Ser Leu Pro Pro Gln Leu Gly Asn Leu
            260                 265                 270

Thr Lys Leu Glu Asn Leu Leu Leu Phe Met Asn Gln Phe Thr Gly Glu
            275                 280                 285

Ile Pro Val Ser Tyr Thr Asn Leu Lys Ala Leu Lys Ala Leu Asp Leu
290                 295                 300

Ser Val Asn Gln Leu Ser Gly Ala Ile Pro Glu Gly Leu Ser Ser Leu
305                 310                 315                 320

Lys Glu Leu Asn Arg Leu Ser Leu Leu Lys Asn Gln Leu Thr Gly Glu
                325                 330                 335

Ile Pro Pro Gly Ile Gly Glu Leu Pro Tyr Leu Asp Thr Leu Glu Leu
                340                 345                 350

Trp Asn Asn Asn Leu Thr Gly Val Leu Pro Gln Lys Leu Gly Ser Asn
                355                 360                 365

Gly Asn Leu Leu Trp Leu Asp Val Ser Asn Ser Ser Leu Ser Gly Pro
370                 375                 380

Ile Pro Pro Asn Leu Cys His Gly Asn Lys Leu Tyr Lys Leu Ile Leu
385                 390                 395                 400

Phe Ser Asn Lys Phe Leu Gly Lys Leu Pro Asp Ser Leu Ala Asn Cys
                405                 410                 415

Thr Ser Leu Ser Arg Phe Arg Ile Gln Asp Asn Gln Leu Asn Gly Ser
                420                 425                 430

Ile Pro Tyr Gly Leu Gly Leu Leu Pro Asn Leu Ser Tyr Val Asp Leu
                435                 440                 445

Ser Lys Asn Asn Phe Thr Gly Glu Ile Pro Asp Asp Leu Gly Tyr Ser
450                 455                 460

Glu Pro Leu His Tyr Leu Asn Ile Ser Gly Asn Ser Phe His Thr Ala
465                 470                 475                 480

Leu Pro Asn Asn Ile Trp Ser Ala Pro Asn Leu Gln Ile Phe Ser Ala
                485                 490                 495

Ser Ser Cys Lys Leu Val Ser Lys Ile Pro Asp Phe Ile Gly Cys Ser
                500                 505                 510

Ser Leu Tyr Arg Ile Glu Leu Gln Asp Asn Met Phe Asn Gly Ser Ile
                515                 520                 525

Pro Arg Asp Ile Gly His Cys Glu Arg Leu Ile Ser Leu Asn Leu Ser
530                 535                 540

Arg Asn Ser Leu Thr Gly Ile Ile Pro Trp Glu Ile Ser Thr Leu Pro
545                 550                 555                 560

Ala Ile Ala Ala Val Asp Leu Ser His Asn Leu Leu Thr Gly Ser Ile
                565                 570                 575

Pro Ser Asn Phe Gly Asn Cys Ser Thr Leu Glu Ser Phe Asn Val Ser
                580                 585                 590

Tyr Asn Leu Leu Thr Gly Pro Ile Pro Ala Ser Gly Thr Ile Phe Pro
                595                 600                 605

Asn Leu His Pro Ser Ser Phe Ser Gly Asn Gln Gly Leu Cys Gly Gly
                610                 615                 620

Val Leu Pro Lys Pro Cys Ala Ala Asp Thr Leu Gly Ala Gly Glu Met
625                 630                 635                 640
```

```
Glu Val Arg His Arg Gln Gln Pro Lys Arg Thr Ala Gly Ala Ile Val
                645                 650                 655

Trp Ile Met Ala Ala Phe Gly Ile Gly Leu Phe Val Leu Val Ala
            660                 665                 670

Gly Thr Arg Cys Phe His Ala Asn Tyr Gly Arg Arg Phe Ser Asp Glu
            675                 680                 685

Arg Glu Ile Gly Pro Trp Lys Leu Thr Ala Phe Gln Arg Leu Asn Phe
            690                 695                 700

Thr Ala Asp Asp Val Leu Glu Cys Leu Ser Met Ser Asp Lys Ile Leu
705                 710                 715                 720

Gly Met Gly Ser Thr Gly Thr Val Tyr Lys Ala Glu Met Pro Gly Gly
                725                 730                 735

Glu Ile Ile Ala Val Lys Lys Leu Trp Gly Lys His Lys Glu Asn Ile
                740                 745                 750

Lys Arg Arg Arg Gly Val Leu Ala Glu Val Asp Val Leu Gly Asn Val
            755                 760                 765

Arg His Arg Asn Ile Val Arg Leu Leu Gly Cys Cys Ser Asn Arg Glu
            770                 775                 780

Cys Thr Met Leu Leu Tyr Glu Tyr Met Pro Asn Gly Asn Leu His Asp
785                 790                 795                 800

Leu Leu His Gly Lys Asn Lys Gly Asp Asn Leu Val Gly Asp Trp Leu
                805                 810                 815

Thr Arg Tyr Lys Ile Ala Leu Gly Val Ala Gln Gly Ile Cys Tyr Leu
            820                 825                 830

His His Asp Cys Asp Pro Val Ile Val His Arg Asp Leu Lys Pro Ser
            835                 840                 845

Asn Ile Leu Leu Asp Gly Glu Met Glu Ala Arg Val Ala Asp Phe Gly
850                 855                 860

Val Ala Lys Leu Ile Gln Ser Asp Glu Ser Met Ser Val Ile Ala Gly
865                 870                 875                 880

Ser Tyr Gly Tyr Ile Ala Pro Glu Tyr Ala Tyr Thr Leu Gln Val Asp
            885                 890                 895

Glu Lys Ser Asp Ile Tyr Ser Tyr Gly Val Val Leu Met Glu Ile Ile
            900                 905                 910

Ser Gly Lys Arg Ser Val Asp Ser Glu Phe Gly Asp Gly Asn Ser Ile
            915                 920                 925

Val Asp Trp Val Arg Pro Lys Ile Lys Ala Lys Asp Gly Val Asn Asp
930                 935                 940

Ile Leu Asp Lys Asp Ala Gly Ala Ser Ile Ala Tyr Val Arg Glu Glu
945                 950                 955                 960

Met Met Gln Met Leu Arg Ile Ala Leu Leu Cys Thr Ser Arg Asn Pro
                965                 970                 975

Ala Asp Arg Pro Ser Met Arg Asp Val Val Leu Met Leu Gln Glu Ala
            980                 985                 990

Lys Pro Lys Arg Lys Leu Pro Gly Ser Ile Val Ser Val Gly Ser Gly
            995                 1000                1005

Asp His Ile Val Thr Val Asp Gly Ala Ile Ala Gln Lys Pro Ala
    1010                1015                1020

Val Glu Cys
    1025

<210> SEQ ID NO 10
<211> LENGTH: 4009
```

```
<212> TYPE: DNA
<213> ORGANISM: Populus tremula x Populus tremuloides

<400> SEQUENCE: 10
atgaaactcc cttttctttt ctttccactt gcgttcttct tctacctgtt caaacctcct     60
cttgtagtgt tctctgctac gactctgcct cccccccctcc aatctcttct ctccattaag    120
accttcctca aagacccttc caatacgttc catgattgga acttgtccaa cactagtggc    180
ttaatccaag aaccagtttg gtgctcgtgg tccggcatca agtgcaaccc agccactgct    240
caaatcacat cactcgatct ctctcaccgg aatctttctg gtgtaattcc agctgagatt    300
agatacttaa cgagcctggt tcacttgaat ttgagtggaa atgcttttga tgggcttctc    360
caacctgcca tttttgaact gggtgacctt aggattcttg acatcagcca caacaacttc    420
aattcaacat tcccacctgg gatttccaag ctcaagttct tgagagtctt caatgcatac    480
agcaacaact tcactggtcc attgcctaaa gaattcgtct ggctgcgctt cctggaggag    540
ctcagccttg gtgggagcta cttcacggga gagattccaa ggagttatgg aagtttcctc    600
agattgaagt acctgcactt agctgggaat gaattggaag gaccattgcc acccgactta    660
ggatccttga gtcagctcga gcacctcgag cttggctacc atccactcct atcaggcaat    720
gtaccagaag aatttgcttt gctgaccaat ctcaagtacc tagatatctc aaagtgtaat    780
ctaacaggca gtctcccacc acaacttgga aatcttacca aactcgagaa tttgctcctt    840
ttcatgaacc agtttactgg tgaaatcccg gtgagctaca caaatctgaa agctctaaaa    900
gcacttgatt tatccgttaa tcagctttca ggggcaattc cagaggggtt atcttccttg    960
aaagagctaa acaggttgag cttgctgaaa aatcagctca ccggcgaaat accaccggga   1020
attggcgagc taccatacct tgacacatta gagctctgga caacaaccct aaccggagtt   1080
ctcccgcaaa agcttggatc caatgggaat ctactatggc ttgacgtctc aaacagttcg   1140
ctctccggcc caattcctcc aaatctatgc catggaaaca agcttacaa gctgattctg    1200
ttctccaaca agtttctcgg taaattacca gattctctag caaactgcac ctctttgtcc   1260
aggttccgaa ttcaagacaa ccagctcaac ggctcaatcc cttatggatt aggtctcctg   1320
cctaatcttt cctatgtgga tttaagcaag aataacttca caggtgaaat tcctgacgat   1380
cttggctatt cagaaccact tcattacttg aacatttctg gaaactccct ccacactgct   1440
ttaccaaaca acatatggag cgcgccaaat cttcagattt tttcagccag tcatgcaag    1500
ctcgtgagca aaataccaga ttttatcggt tgcagcagtc tgtacaggat agaattgcaa   1560
gacaatatgt tcaatggcag cattccacgg atatcggcc attgtgagag gctcatttcg    1620
cttaatttaa gccgcaattc tcttactggt attattccgt gggagatttc tacacttcct   1680
gctatcgctg ctgtcgattt gtcccataat ttactcaccg gttccattcc ttcaaatttt   1740
ggtaactgtt caactttgga gagttttaat gtgtcctata atttgttaac tggacccatt   1800
cctgcatcgg gtacaatatt tccaaatttg catccgtctt cctttcggg caatcaagga    1860
ttatgcggtg gcgttttgcc aaagccttgt gctgcggata cattggggc tggagaaatg    1920
gaggtccgcc atagacagca gcccaaaagg actgctggcg ctatagtgtg gattatggcg   1980
gctgcttttg gtattggatt attgtgcttt gttgctggga ctaggtgttt ccatgcgaac   2040
tatggccgta gatttagtga tgaacgagag atcggaccgt ggaaattaac tgcctttcaa   2100
cggttgaatt tcacggcaga cgatgtgctc gagtgtctat ctatgtcgga caagatctta   2160
gggatgggt caacggggac ggtctataag gcggaaatgc caggtggcga gatcatagcg    2220
```

```
gtgaagaaac tgtggggtaa gcataaggag aacatcaaaa ggaggagagg ggtgttagcc    2280
gaggtggatg ttttaggtaa cgtgaggcat aggaatatag tgagattgct aggatgttgc    2340
agtaacaggg agtgtacaat gttgctgtac gagtacatgc ctaatggtaa cttacatgat    2400
ttgttgcatg ggaaaaacaa gggagacaat ttggtgggtg attggcttac aaggtacaag    2460
attgcactgg gagtggcaca ggggatttgc tatttgcatc atgattgtga tcctgtgatt    2520
gtgcaccgag atcttaagcc tagtaatata ttattggacg gtgagatgga ggctagagtg    2580
gcagattttg gggtggcaaa gctgatccaa agtgacgaat ccatgtcagt cattgctggg    2640
tcttatggct acattgcgcc aggtacggtc ctggtcccat gctgcttct cttttatttt     2700
ttttatgaga tttgtttgtg cccttcaagt gcatttcacc ttacgagtag aaaacagaaa    2760
acgtgggtaa ttttgaattg aaattcgatc gtcaacagtc gacttttgta agaatacaga    2820
gtccctgtct cgtactgcag tgaagaactg gatcaattag ttaaggtcgt gtaataaaac    2880
aaaacaaaag aggaaagaca aatgtgttac gagtaggacg gttgatttta ggacggaaag    2940
catagaaatt atatcttctt gcttggagat cctcaatgta tcttcttcgc ttgcttttct    3000
ttctttctgc cgtatttgca tacacaggac tagattgaag ctggtctcgt ttgaaattcc    3060
tggataccct ttgtctatgt ttgcttagtt cgttttgctg gtatatctag aatatggagt    3120
gtcaaatctt gaaacaggac atgggaatta gagataatta cataccgaaa cactttctt    3180
ttattttatt tcttgattgt tttgccatga agacatccca tccatacttg attttccaaa    3240
tgcaaaaaaa ggagcggtaa atactacagt acagagtgca gtggtggggt ggggtggacg    3300
tcatttcttc ttttgggccg cgaatttgca actgttcgag acctttgagt gcgtggcgca    3360
ctcactattg cgcgtggacg ctctccttat tattattttt tcctttttaaa ttctccttt     3420
cctctcacgc cttttttttt gggtagattt accatgtaca gttggaccca cgaataattt    3480
cttttagatc ctcgcattca ttgcagtttt tgacttctcg atgcacttgc catgatttct    3540
ttctttgttg gattgagttg ggtcactgaa atcttgcttt taccgtgcag agtatgctta    3600
cacactgcag gttgatgaga agagtgatat ttatagttat ggggtggtgt taatggagat    3660
tataagcggc aagaggtcgg tcgattctga gttcggggat ggtaacagca ttgttgactg    3720
ggtaaggccg aagataaagg ctaaggacgg tgtaaatgac attttagaca aggatgctgg    3780
ggcatcgatt gcatatgtga gggaagaaat gatgcaaatg cttagaattg ctttgctatg    3840
caccagccgg aatccggcgg accgaccgtc gatgagggat gtcgtgttga tgctgcaaga    3900
agccaagccc aagaggaaac tgccgggaag tatagttagt gttggtagtg gtgaccacat    3960
tgttactgtt gatggggcta ttgcacaaaa gcctgcagtc gaatgttaa               4009

<210> SEQ ID NO 11
<211> LENGTH: 1026
<212> TYPE: PRT
<213> ORGANISM: Populus trichocarpa

<400> SEQUENCE: 11

Met Lys Leu Pro Phe Leu Phe Leu Leu Ala Phe Phe Tyr Leu
1               5                   10                  15

Phe Lys Pro Pro Leu Leu Val Phe Ser Ala Thr Thr Leu Pro Pro
            20                  25                  30

Leu Gln Ser Leu Leu Ser Ile Lys Thr Phe Leu Lys Asp Pro Ser Asn
        35                  40                  45

Thr Phe His Asp Trp Asn Leu Ser Asn Thr Ser Gly Leu Ile Gln Glu
    50                  55                  60
```

```
Pro Val Trp Cys Ser Trp Ser Gly Ile Lys Cys Asn Pro Ala Thr Ala
 65                  70                  75                  80

Gln Ile Thr Ser Leu Asp Leu Ser His Arg Asn Leu Ser Gly Val Ile
             85                  90                  95

Pro Ala Glu Ile Arg Tyr Leu Thr Ser Leu Val His Leu Asn Leu Ser
            100                 105                 110

Gly Asn Ala Phe Asp Gly Leu Leu Gln Pro Ala Ile Phe Glu Leu Gly
            115                 120                 125

Asp Leu Arg Ile Leu Asp Ile Ser His Asn Asn Phe Asn Ser Thr Phe
130                 135                 140

Pro Thr Gly Ile Ser Lys Leu Lys Phe Leu Arg Val Phe Asn Ala Tyr
145                 150                 155                 160

Ser Asn Asn Phe Thr Gly Pro Leu Pro Lys Glu Phe Val Trp Leu Arg
                165                 170                 175

Phe Leu Glu Glu Leu Asn Leu Gly Gly Ser Tyr Phe Thr Gly Glu Ile
            180                 185                 190

Pro Arg Ser Tyr Gly Ser Phe Leu Arg Leu Lys Tyr Leu Tyr Leu Ala
            195                 200                 205

Gly Asn Glu Leu Glu Gly Pro Leu Pro Asp Leu Gly Phe Leu Ser
210                 215                 220

Gln Leu Glu His Leu Glu Leu Gly Tyr His Pro Leu Leu Ser Gly Asn
225                 230                 235                 240

Val Pro Glu Glu Phe Ala Leu Leu Thr Asn Leu Lys Tyr Leu Asp Ile
            245                 250                 255

Ser Lys Cys Asn Leu Ser Gly Ser Leu Pro Pro Gln Leu Gly Asn Leu
            260                 265                 270

Thr Lys Leu Glu Asn Leu Leu Leu Phe Met Asn Gln Phe Thr Gly Glu
            275                 280                 285

Ile Pro Val Ser Tyr Thr Asn Leu Lys Ala Leu Lys Ala Leu Asp Leu
290                 295                 300

Ser Val Asn Gln Leu Ser Gly Ala Ile Pro Glu Gly Leu Ser Ser Leu
305                 310                 315                 320

Lys Glu Leu Asn Arg Leu Ser Phe Leu Lys Asn Gln Leu Thr Gly Glu
            325                 330                 335

Ile Pro Pro Gly Ile Gly Glu Leu Pro Tyr Leu Asp Thr Leu Glu Leu
            340                 345                 350

Trp Asn Asn Asn Leu Thr Gly Val Leu Pro Gln Lys Leu Gly Ser Asn
            355                 360                 365

Gly Asn Leu Leu Trp Leu Asp Val Ser Asn Asn Ser Leu Ser Gly Pro
            370                 375                 380

Ile Pro Pro Asn Leu Cys Gln Gly Asn Lys Leu Tyr Lys Leu Ile Leu
385                 390                 395                 400

Phe Ser Asn Lys Phe Leu Gly Lys Leu Pro Asp Ser Leu Ala Asn Cys
            405                 410                 415

Thr Ser Leu Ser Arg Phe Arg Ile Gln Asp Asn Gln Leu Asn Gly Ser
            420                 425                 430

Ile Pro Tyr Gly Leu Gly Leu Leu Pro Asn Leu Ser Tyr Val Asp Leu
            435                 440                 445

Ser Lys Asn Asn Phe Thr Gly Glu Ile Pro Asp Asp Leu Gly Asn Ser
            450                 455                 460

Glu Pro Leu His Phe Leu Asn Ile Ser Gly Asn Ser Phe His Thr Ala
465                 470                 475                 480
```

```
Leu Pro Asn Asn Ile Trp Ser Ala Pro Asn Leu Gln Ile Phe Ser Ala
            485                 490                 495

Ser Ser Cys Lys Leu Val Ser Lys Ile Pro Asp Phe Ile Gly Cys Ser
        500                 505                 510

Ser Leu Tyr Arg Ile Glu Leu Gln Asp Asn Met Phe Asn Gly Ser Ile
        515                 520                 525

Pro Trp Asp Ile Gly His Cys Glu Arg Leu Ile Ser Leu Asn Leu Ser
        530                 535                 540

Arg Asn Ser Leu Thr Gly Ile Ile Pro Trp Glu Ile Ser Thr Leu Pro
545                 550                 555                 560

Ala Ile Ala Asp Val Asp Leu Ser His Asn Leu Leu Thr Gly Ser Ile
                565                 570                 575

Pro Ser Asn Phe Gly Asn Cys Ser Thr Leu Glu Ser Phe Asn Val Ser
            580                 585                 590

Tyr Asn Leu Leu Thr Gly Pro Ile Pro Ala Ser Gly Thr Ile Phe Pro
        595                 600                 605

Asn Leu His Pro Ser Ser Phe Ser Gly Asn Gln Gly Leu Cys Gly Gly
        610                 615                 620

Val Leu Pro Lys Pro Cys Ala Ala Asp Thr Leu Gly Ala Gly Glu Met
625                 630                 635                 640

Glu Val Arg His Arg Gln Pro Lys Arg Thr Ala Gly Ala Ile Val
                645                 650                 655

Trp Ile Met Ala Ala Ala Phe Gly Ile Gly Leu Phe Val Leu Val Ala
                660                 665                 670

Gly Thr Arg Cys Phe His Ala Asn Tyr Gly Arg Arg Phe Ser Asp Glu
        675                 680                 685

Arg Glu Ile Gly Pro Trp Lys Leu Thr Ala Phe Gln Arg Leu Asn Phe
        690                 695                 700

Thr Ala Asp Asp Val Leu Glu Cys Leu Ser Met Ser Asp Lys Ile Leu
705                 710                 715                 720

Gly Met Gly Ser Thr Gly Thr Val Tyr Lys Ala Glu Met Pro Gly Gly
                725                 730                 735

Glu Ile Ile Ala Val Lys Lys Leu Trp Gly Lys His Lys Glu Asn Ile
            740                 745                 750

Arg Arg Arg Arg Gly Val Leu Ala Glu Val Asp Val Leu Gly Asn Val
        755                 760                 765

Arg His Arg Asn Ile Val Arg Leu Leu Gly Cys Cys Ser Asn Arg Glu
        770                 775                 780

Cys Thr Met Leu Leu Tyr Glu Tyr Met Pro Asn Gly Asn Leu His Asp
785                 790                 795                 800

Leu Leu His Gly Lys Asn Lys Gly Asp Asn Leu Val Gly Asp Trp Leu
                805                 810                 815

Thr Arg Tyr Lys Ile Ala Leu Gly Val Ala Gln Gly Ile Cys Tyr Leu
            820                 825                 830

His His Asp Cys Asp Pro Val Ile Val His Arg Asp Leu Lys Pro Ser
        835                 840                 845

Asn Ile Leu Leu Asp Gly Glu Met Glu Ala Arg Val Ala Asp Phe Gly
        850                 855                 860

Val Ala Lys Leu Ile Gln Ser Asp Glu Ser Met Ser Val Ile Ala Gly
865                 870                 875                 880

Ser Tyr Gly Tyr Ile Ala Pro Glu Tyr Ala Tyr Thr Leu Gln Val Asp
                885                 890                 895

Glu Lys Ser Asp Ile Tyr Ser Tyr Gly Val Val Leu Met Glu Ile Ile
```

```
                    900                 905                 910
Ser Gly Lys Arg Ser Val Asp Ala Glu Phe Gly Asp Gly Asn Ser Ile
                915                 920                 925

Val Asp Trp Val Arg Ser Lys Ile Lys Ala Lys Asp Gly Val Asn Asp
            930                 935                 940

Ile Leu Asp Lys Asp Ala Gly Ala Ser Ile Ala Ser Val Arg Glu Glu
945                 950                 955                 960

Met Met Gln Met Leu Arg Ile Ala Leu Leu Cys Thr Ser Arg Asn Pro
                965                 970                 975

Ala Asp Arg Pro Ser Met Arg Asp Val Val Leu Met Leu Gln Glu Ala
            980                 985                 990

Lys Pro Lys Arg Lys Leu Pro Gly Ser Ile Val Ser Val Gly Ser Gly
        995                 1000                1005

Asp His Ile Val Thr Val Asp Gly Ala Ile Ala Gln Lys Pro Ala
    1010                1015                1020

Val Glu Cys
    1025

<210> SEQ ID NO 12
<211> LENGTH: 313
<212> TYPE: PRT
<213> ORGANISM: Oryza sativa

<400> SEQUENCE: 12

Val Lys Glu Ala Asn Val Val Gly Met Gly Ala Thr Gly Val Val Tyr
1               5                   10                  15

Lys Ala Glu Leu Pro Arg Ala Arg Ala Val Ile Ala Val Lys Lys Leu
            20                  25                  30

Trp Arg Pro Ala Ala Ala Ala Glu Ala Ala Ala Ala Pro Glu Leu
        35                  40                  45

Thr Ala Glu Val Leu Lys Glu Val Gly Leu Leu Gly Arg Leu Arg His
    50                  55                  60

Arg Asn Ile Val Arg Leu Leu Gly Tyr Met His Asn Glu Ala Asp Ala
65                  70                  75                  80

Met Met Leu Tyr Glu Phe Met Pro Asn Gly Ser Leu Trp Glu Ala Leu
                85                  90                  95

His Gly Pro Pro Glu Arg Arg Thr Leu Val Asp Trp Val Ser Arg Tyr
            100                 105                 110

Asp Val Ala Ala Gly Val Ala Gln Gly Leu Ala Tyr Leu His His Asp
        115                 120                 125

Cys His Pro Pro Val Ile His Arg Asp Ile Lys Ser Asn Asn Ile Leu
    130                 135                 140

Leu Asp Ala Asn Met Glu Ala Arg Ile Ala Asp Phe Gly Leu Ala Arg
145                 150                 155                 160

Ala Leu Gly Arg Ala Gly Glu Ser Val Ser Val Val Ala Gly Ser Tyr
                165                 170                 175

Gly Tyr Ile Ala Pro Glu Tyr Gly Tyr Thr Met Lys Val Asp Gln Lys
            180                 185                 190

Ser Asp Thr Tyr Ser Tyr Gly Val Val Leu Met Glu Leu Ile Thr Gly
        195                 200                 205

Arg Arg Ala Val Glu Ala Ala Phe Gly Glu Gly Gln Asp Ile Val Gly
    210                 215                 220

Trp Val Arg Asn Lys Ile Arg Ser Asn Thr Val Glu Asp His Leu Asp
225                 230                 235                 240
```

Gly Gln Leu Val Gly Ala Gly Cys Pro His Val Arg Glu Glu Met Leu
                245                 250                 255

Leu Val Leu Arg Thr Ala Val Leu Cys Thr Ala Arg Leu Pro Arg Asp
            260                 265                 270

Arg Pro Ser Met Arg Asp Val Ile Thr Met Leu Gly Glu Ala Lys Pro
        275                 280                 285

Arg Arg Lys Ser Gly Ser Ser Thr Gly Ser Ala Ser Ala Lys Ala Pro
    290                 295                 300

Thr Pro Ala Pro Pro Ala Val Ala Ala
305                 310

<210> SEQ ID NO 13
<211> LENGTH: 305
<212> TYPE: PRT
<213> ORGANISM: Oryza sativa

<400> SEQUENCE: 13

Ile Lys Glu Ala Asn Ile Val Gly Met Gly Gly Thr Gly Val Val Tyr
1               5                   10                  15

Arg Ala Asp Met Pro Arg His His Ala Val Ala Val Lys Lys Leu
            20                  25                  30

Trp Arg Ala Ala Gly Cys Pro Glu Glu Ala Thr Thr Val Asp Gly Arg
            35                  40                  45

Thr Asp Val Glu Ala Gly Gly Glu Phe Ala Ala Glu Val Lys Leu Leu
        50                  55                  60

Gly Arg Leu Arg His Arg Asn Val Val Arg Met Leu Gly Tyr Val Ser
65              70                  75                  80

Asn Asn Leu Asp Thr Met Val Ile Tyr Glu Tyr Met Val Asn Gly Ser
                85                  90                  95

Leu Trp Asp Ala Leu His Gly Gln Arg Lys Gly Lys Met Leu Met Asp
            100                 105                 110

Trp Val Ser Arg Tyr Asn Val Ala Ala Gly Val Ala Ala Gly Leu Ala
        115                 120                 125

Tyr Leu His His Asp Cys Arg Pro Pro Val Ile His Arg Asp Val Lys
    130                 135                 140

Ser Ser Asn Val Leu Leu Asp Asp Asn Met Asp Ala Lys Ile Ala Asp
145                 150                 155                 160

Phe Gly Leu Ala Arg Val Met Ala Arg Ala His Glu Thr Val Ser Val
                165                 170                 175

Val Ala Gly Ser Tyr Gly Tyr Ile Ala Pro Glu Tyr Gly Tyr Thr Leu
            180                 185                 190

Lys Val Asp Gln Lys Ser Asp Ile Tyr Ser Phe Gly Val Val Leu Met
        195                 200                 205

Glu Leu Leu Thr Gly Arg Arg Pro Ile Glu Pro Glu Tyr Gly Glu Ser
    210                 215                 220

Gln Asp Ile Val Gly Trp Ile Arg Glu Arg Leu Arg Ser Asn Thr Gly
225                 230                 235                 240

Val Glu Glu Leu Leu Asp Ala Ser Val Gly Gly Arg Val Asp His Val
                245                 250                 255

Arg Glu Glu Met Leu Leu Val Leu Arg Val Ala Val Leu Cys Thr Ala
            260                 265                 270

Lys Ser Pro Lys Asp Arg Pro Thr Met Arg Asp Val Val Thr Met Leu
        275                 280                 285

Gly Glu Ala Lys Pro Arg Arg Lys Ser Ser Ser Ala Thr Val Ala Ala
    290                 295                 300

Thr
305

<210> SEQ ID NO 14
<211> LENGTH: 309
<212> TYPE: PRT
<213> ORGANISM: Oryza sativa

<400> SEQUENCE: 14

Gly Ser Asp Gly Ile Val Gly Ala Gly Ser Ser Gly Thr Val Tyr Arg
1               5                   10                  15

Ala Lys Met Pro Asn Gly Glu Val Ile Ala Val Lys Lys Leu Trp Gln
            20                  25                  30

Ala Pro Ala Ala Gln Lys Glu Ala Ala Pro Thr Glu Gln Asn Gln
        35                  40                  45

Lys Leu Arg Gln Asp Ser Asp Gly Gly Gly Lys Arg Thr Val
    50                  55                  60

Ala Glu Val Glu Val Leu Gly His Leu Arg His Arg Asn Ile Val Arg
65                  70                  75                  80

Leu Leu Gly Trp Cys Thr Asn Gly Glu Ser Thr Met Leu Leu Tyr Glu
                85                  90                  95

Tyr Met Pro Asn Gly Ser Leu Asp Glu Leu His Gly Ala Ala Ala
            100                 105                 110

Lys Ala Arg Pro Gly Trp Asp Ala Arg Tyr Lys Ile Ala Val Gly Val
            115                 120                 125

Ala Gln Gly Val Ser Tyr Leu His His Asp Cys Leu Pro Ala Ile Ala
130                 135                 140

His Arg Asp Ile Lys Pro Ser Asn Ile Leu Leu Asp Asp Met Glu
145                 150                 155                 160

Ala Arg Val Ala Asp Phe Gly Val Ala Lys Ala Leu Gln Ser Ala Ala
                165                 170                 175

Pro Met Ser Val Val Ala Gly Ser Cys Gly Tyr Ile Ala Pro Glu Tyr
            180                 185                 190

Thr Tyr Thr Leu Lys Val Asn Glu Lys Ser Asp Val Tyr Ser Pro Gly
            195                 200                 205

Val Val Leu Leu Glu Ile Leu Thr Gly Arg Arg Ser Val Glu Ala Glu
210                 215                 220

Tyr Gly Glu Gly Asn Asn Ile Val Asp Trp Val Arg Arg Lys Val Ala
225                 230                 235                 240

Gly Gly Gly Val Gly Asp Val Ile Asp Ala Ala Trp Ala Asp Asn
                245                 250                 255

Asp Val Gly Gly Thr Arg Asp Glu Met Ala Leu Ala Leu Arg Val Ala
            260                 265                 270

Leu Leu Cys Thr Ser Arg Cys Pro Gln Glu Arg Pro Ser Met Arg Glu
        275                 280                 285

Val Leu Ser Met Leu Gln Glu Ala Arg Pro Lys Arg Lys Asn Ser Ala
    290                 295                 300

Lys Lys Gln Val Lys
305

<210> SEQ ID NO 15
<211> LENGTH: 305
<212> TYPE: PRT
<213> ORGANISM: Populus tremula x Populus tremuloides

<400> SEQUENCE: 15

Met Ser Asp Lys Ile Leu Gly Met Gly Ser Thr Gly Thr Val Tyr Lys
1               5                   10                  15

Ala Glu Met Pro Gly Gly Ile Ile Ala Val Lys Lys Leu Trp Gly
            20                  25                  30

Lys His Lys Glu Asn Ile Arg Arg Arg Gly Val Leu Ala Glu Val
        35                  40                  45

Asp Val Leu Gly Asn Val Arg His Arg Asn Ile Val Arg Leu Leu Gly
        50                  55                  60

Cys Cys Ser Asn Arg Glu Cys Thr Met Leu Leu Tyr Glu Tyr Met Pro
65                  70                  75                  80

Asn Gly Asn Leu His Asp Leu Leu His Gly Lys Asn Lys Gly Asp Asn
                85                  90                  95

Leu Val Gly Asp Trp Leu Thr Arg Tyr Lys Ile Ala Leu Gly Val Ala
                100                 105                 110

Gln Gly Ile Cys Tyr Leu His His Asp Cys Asp Pro Val Ile Val His
            115                 120                 125

Arg Asp Leu Lys Pro Ser Asn Ile Leu Leu Asp Gly Glu Met Glu Ala
145     130                 135                 140

Arg Val Arg Asp Phe Gly Val Ala Lys Leu Ile Gln Ser Asp Glu Ser
145                 150                 155                 160

Met Ser Val Ile Ala Gly Ser Tyr Gly Tyr Ile Ala Pro Glu Tyr Ala
                165                 170                 175

Tyr Thr Leu Gln Val Asp Glu Lys Ser Asp Ile Tyr Ser Tyr Gly Val
                180                 185                 190

Val Leu Met Glu Ile Ile Ser Gly Lys Arg Ser Val Asp Ala Glu Phe
                195                 200                 205

Gly Asp Gly Asn Ser Ile Val Asp Trp Val Arg Ser Lys Ile Lys Ala
            210                 215                 220

Lys Asp Gly Val Asn Asp Ile Leu Asp Lys Asp Ala Gly Ala Ser Ile
225                 230                 235                 240

Ala Ser Val Arg Glu Glu Met Met Gln Met Leu Arg Ile Ala Leu Leu
                245                 250                 255

Cys Thr Ser Arg Asn Pro Ala Asp Arg Pro Ser Met Arg Asp Val Val
                260                 265                 270

Leu Met Leu Gln Glu Ala Lys Pro Lys Arg Lys Leu Pro Gly Ser Ile
                275                 280                 285

Val Ser Val Gly Ser Gly Asp His Ile Val Thr Val Asp Gly Ala Ile
            290                 295                 300

Ala
305

<210> SEQ ID NO 16
<211> LENGTH: 251
<212> TYPE: PRT
<213> ORGANISM: Populus tremula x Populus tremuloides

<400> SEQUENCE: 16

Lys Thr Asp Asn Ile Leu Gly Met Gly Ser Thr Gly Thr Val Tyr Lys
1               5                   10                  15

Ala Glu Met Pro Asn Gly Glu Ile Ile Ala Val Lys Lys Leu Trp Gly
            20                  25                  30

Lys Asn Lys Glu Asn Gly Lys Ile Arg Arg Arg Lys Ser Gly Val Leu
        35                  40                  45

Ala Glu Val Asp Val Leu Gly Asn Val Arg His Arg Asn Ile Val Arg

|     |     |     |     | 50  |     |     |     |     | 55  |     |     |     |     | 60  |     |
| --- | --- | --- | --- | --- | --- | --- | --- | --- | --- | --- | --- | --- | --- | --- | --- |

Leu Leu Gly Cys Cys Thr Asn Arg Asp Cys Thr Met Leu Leu Tyr Glu
65                  70                  75                  80

Tyr Met Pro Asn Gly Ser Leu Asp Asp Leu His Gly Gly Asp Lys
                85                  90                  95

Thr Met Thr Ala Ala Ala Glu Trp Thr Ala Leu Tyr Gln Ile Ala Ile
            100                 105                 110

Gly Val Ala Gln Gly Ile Cys Tyr Leu His His Asp Cys Asp Pro Val
            115                 120                 125

Ile Val His Arg Asp Leu Lys Pro Ser Asn Ile Leu Leu Asp Ala Asp
            130                 135                 140

Phe Glu Ala Arg Val Ala Asp Phe Gly Val Ala Lys Leu Ile Gln Thr
145                 150                 155                 160

Asp Glu Ser Met Ser Val Val Ala Gly Ser Tyr Gly Tyr Ile Ala Pro
                165                 170                 175

Glu Tyr Ala Tyr Thr Leu Gln Val Asp Lys Lys Ser Asp Ile Tyr Ser
                180                 185                 190

Tyr Gly Val Ile Leu Leu Glu Ile Ile Thr Gly Lys Arg Ser Val Glu
            195                 200                 205

Pro Glu Phe Gly Glu Gly Asn Ser Ile Val Asp Trp Val Arg Ser Lys
210                 215                 220

Leu Lys Thr Lys Glu Asp Val Glu Glu Val Leu Asp Lys Ser Met Gly
225                 230                 235                 240

Arg Ser Cys Ser Leu Ile Arg Glu Glu Met Lys
                245                 250

<210> SEQ ID NO 17
<211> LENGTH: 287
<212> TYPE: PRT
<213> ORGANISM: Populus tremula x Populus tremuloides

<400> SEQUENCE: 17

Ile Lys Glu Ser Asn Ile Ile Gly Met Gly Ala Ile Gly Ile Val Tyr
1               5                   10                  15

Lys Ala Glu Val Met Arg Arg Pro Leu Leu Thr Val Ala Val Lys Lys
                20                  25                  30

Leu Trp Arg Ser Pro Ser Pro Gln Asn Asp Ile Glu Asp His His Gln
            35                  40                  45

Glu Glu Asp Glu Glu Asp Asp Ile Leu Arg Glu Val Asn Leu Leu Gly
        50                  55                  60

Gly Leu Arg His Arg Asn Ile Val Lys Ile Leu Gly Tyr Val His Asn
65                  70                  75                  80

Glu Arg Glu Val Met Met Val Tyr Glu Tyr Met Pro Asn Gly Asn Leu
                85                  90                  95

Gly Thr Ala Leu His Ser Lys Asp Glu Lys Phe Leu Leu Arg Asp Trp
            100                 105                 110

Leu Ser Arg Tyr Asn Val Ala Val Gly Val Val Gln Gly Leu Asn Tyr
            115                 120                 125

Leu His Asn Asp Cys Tyr Pro Pro Ile Ile His Arg Asp Ile Lys Ser
            130                 135                 140

Asn Asn Ile Leu Leu Asp Ser Asn Leu Glu Ala Arg Ile Ala Asp Phe
145                 150                 155                 160

Gly Leu Ala Lys Met Met Leu His Lys Asn Glu Thr Val Ser Met Val
            165                 170                 175

Ala Gly Ser Tyr Gly Tyr Ile Ala Pro Glu Tyr Gly Tyr Thr Leu Lys
            180                 185                 190

Ile Asp Glu Lys Ser Asp Ile Tyr Ser Leu Gly Val Val Leu Leu Glu
            195                 200                 205

Leu Val Thr Gly Lys Met Pro Ile Asp Pro Ser Phe Glu Asp Ser Ile
            210                 215                 220

Asp Val Val Glu Trp Ile Arg Arg Lys Val Lys Lys Asn Glu Ser Leu
225                 230                 235                 240

Glu Glu Val Ile Asp Ala Ser Ile Ala Gly Asp Cys Lys His Val Ile
            245                 250                 255

Glu Glu Met Leu Leu Ala Leu Arg Ile Ala Leu Leu Cys Thr Ala Lys
            260                 265                 270

Leu Pro Lys Asp Arg Pro Ser Ile Arg Asp Val Ile Thr Met Leu
            275                 280                 285

<210> SEQ ID NO 18
<211> LENGTH: 276
<212> TYPE: PRT
<213> ORGANISM: Populus tremula x Populus tremuloides

<400> SEQUENCE: 18

Lys Glu Ser Asn Met Ile Gly Met Gly Ala Thr Gly Ile Val Tyr Lys
1               5                   10                  15

Ala Glu Met Ser Arg Ser Ser Thr Val Leu Ala Val Lys Lys Leu Trp
            20                  25                  30

Arg Ser Ala Ala Asp Ile Glu Asp Gly Thr Thr Gly Asp Phe Val Gly
            35                  40                  45

Glu Val Asn Leu Leu Gly Lys Leu Arg His Arg Asn Ile Val Arg Leu
    50                  55                  60

Leu Gly Phe Leu Tyr Asn Asp Lys Asn Met Met Ile Val Tyr Glu Phe
65                  70                  75                  80

Met Leu Asn Gly Asn Leu Gly Asp Ala Ile His Gly Lys Asn Ala Ala
            85                  90                  95

Gly Arg Leu Leu Val Asp Trp Val Ser Arg Tyr Asn Ile Ala Leu Gly
            100                 105                 110

Val Ala His Gly Leu Tyr Leu His His Asp Cys His Pro Pro Val Ile
            115                 120                 125

His Arg Asp Ile Lys Ser Asn Asn Ile Leu Leu Asp Ala Asn Leu Asp
            130                 135                 140

Ala Arg Ile Ala Asp Phe Gly Leu Ala Arg Met Met Ala Arg Lys Lys
145                 150                 155                 160

Glu Thr Val Ser Met Val Ala Gly Ser Tyr Gly Tyr Ile Ala Pro Glu
            165                 170                 175

Tyr Gly Tyr Thr Leu Lys Val Asp Glu Lys Ile Asp Ile Tyr Ser Tyr
            180                 185                 190

Gly Val Val Leu Leu Glu Leu Leu Thr Gly Arg Arg Leu Glu Pro Glu
            195                 200                 205

Phe Gly Glu Ser Val Asp Ile Val Glu Trp Val Arg Arg Lys Ile Arg
            210                 215                 220

Asp Asn Ile Ser Leu Glu Glu Ala Leu Asp Pro Asn Val Gly Asn Cys
225                 230                 235                 240

Arg Tyr Val Gln Glu Glu Met Leu Leu Val Leu Gln Ile Ala Leu Leu
            245                 250                 255

Cys Thr Thr Lys Leu Pro Lys Asp Arg Pro Ser Met Arg Asp Val Ile
            260                 265                 270

Ser Met Leu Gly
        275

<210> SEQ ID NO 19
<211> LENGTH: 308
<212> TYPE: PRT
<213> ORGANISM: Artificial Sequence
<220> FEATURE:
<223> OTHER INFORMATION: Consensus artificial amino acid sequence for
      PXY protein
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (23)..(26)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(48)
<223> OTHER INFORMATION: Xaa can be any naturally occurring amino acid
<220> FEATURE:
<221> NAME/KEY: misc_feature
<222> LOCATION: (50)..(64)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (91)..(93)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (113)..(115)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (178)..(181)
<223> OTHER INFORMATION: Xaa can be any naturally occurring amino acid
<220> FEATURE:
<221> NAME/KEY: misc_feature
<222> LOCATION: (243)..(243)
<223> OTHER INFORMATION: Xaa can be any naturally occurring amino acid
<220> FEATURE:
<221> NAME/KEY: misc_feature
<222> LOCATION: (247)..(248)
<223> OTHER INFORMATION: Xaa can be any naturally occurring amino acid
<220> FEATURE:
<221> NAME/KEY: misc_feature
<222> LOCATION: (250)..(250)

```
<223> OTHER INFORMATION: Xaa can be any naturally occurring amino acid
<220> FEATURE:
<221> NAME/KEY: misc_feature
<222> LOCATION: (252)..(252)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (262)..(264)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (301)..(301)
<223> OTHER INFORMATION: Xaa can be any naturally occurring amino acid

<400> SEQUENCE: 19

Xaa Lys Glu Ala Asn Ile Val Gly Met Gly Ala Thr Gly Ile Val Tyr
1               5                   10                  15

Lys Ala Glu Met Pro Arg Xaa Xaa Xaa Xaa Val Ile Ala Val Lys Lys
            20                  25                  30

Leu Trp Arg Ala Xaa Ala Xaa Xaa Xaa Xaa Xaa Xaa Xaa Xaa Xaa Xaa
        35                  40                  45

Glu Xaa Xaa Xaa Xaa Xaa Xaa Xaa Xaa Xaa Xaa Xaa Xaa Xaa Xaa Xaa
    50                  55                  60

Asp Val Leu Ala Glu Val Xaa Leu Leu Gly Xaa Leu Arg His Arg Asn
65                  70                  75                  80

Ile Val Arg Leu Leu Gly Tyr Val Ser Asn Xaa Xaa Xaa Thr Met Leu
                85                  90                  95

Leu Tyr Glu Tyr Met Pro Asn Gly Ser Leu Xaa Asp Ala Leu His Gly
            100                 105                 110

Xaa Xaa Xaa Ala Xaa Lys Leu Leu Xaa Asp Trp Val Ser Arg Tyr Asn
        115                 120                 125

Ile Ala Leu Gly Val Ala Gln Gly Leu Ala Tyr Leu His His Asp Cys
    130                 135                 140

Xaa Pro Pro Ile Ile His Arg Asp Ile Lys Ser Ser Asn Ile Leu Leu
145                 150                 155                 160

Asp Ala Asn Met Glu Ala Arg Ile Ala Asp Phe Gly Leu Ala Lys Leu
                165                 170                 175

Met Xaa Xaa Xaa Xaa Glu Ser Val Ser Val Ala Gly Ser Tyr Gly
            180                 185                 190

Tyr Ile Ala Pro Glu Tyr Gly Tyr Thr Leu Lys Val Asp Glu Lys Ser
        195                 200                 205

Asp Ile Tyr Ser Tyr Gly Val Val Leu Leu Glu Leu Ile Thr Gly Arg
    210                 215                 220

Arg Ser Val Glu Pro Glu Phe Gly Glu Gly Asn Asp Ile Val Asp Trp
225                 230                 235                 240

Val Arg Xaa Lys Ile Lys Xaa Xaa Asn Xaa Val Xaa Glu Xaa Leu Asp
                245                 250                 255
```

```
Xaa Ala Ala Val Ala Xaa Xaa Xaa Cys Xaa His Val Arg Glu Glu Met
            260                 265                 270

Leu Leu Val Leu Arg Ile Ala Leu Leu Cys Thr Ala Lys Xaa Pro Lys
        275                 280                 285

Asp Arg Pro Ser Met Arg Asp Val Ile Thr Met Leu Xaa Glu Ala Lys
    290                 295                 300

Pro Lys Arg Lys
305

<210> SEQ ID NO 20
<211> LENGTH: 36
<212> TYPE: DNA
<213> ORGANISM: Artificial Sequence
<220> FEATURE:
<223> OTHER INFORMATION: Primer pPtPP2-F

<400> SEQUENCE: 20
atccctaggc ctgcaggtaa gctatgtacg ttttgg                             36

<210> SEQ ID NO 21
<211> LENGTH: 26
<212> TYPE: DNA
<213> ORGANISM: Artificial Sequence
<220> FEATURE:
<223> OTHER INFORMATION: Primer pPttANT-R

<400> SEQUENCE: 21
atcactagtg acaagctgag agactg                                        26

<210> SEQ ID NO 22
<211> LENGTH: 26
<212> TYPE: DNA
<213> ORGANISM: Artificial Sequence
<220> FEATURE:
<223> OTHER INFORMATION: Primer pPttANT-F

<400> SEQUENCE: 22
atcgggcccc cgaagttgct cacttc                                        26

<210> SEQ ID NO 23
<211> LENGTH: 26
<212> TYPE: DNA
<213> ORGANISM: Artificial Sequence
<220> FEATURE:
<223> OTHER INFORMATION: Primer pPttANT-R

<400> SEQUENCE: 23
atcactagtg acaagctgag agactg                                        26

<210> SEQ ID NO 24
<211> LENGTH: 24
<212> TYPE: DNA
<213> ORGANISM: Artificial Sequence
<220> FEATURE:
<223> OTHER INFORMATION: Primer PttCLE41-F

<400> SEQUENCE: 24
cacctagcta gccttggtgc tggt                                          24

<210> SEQ ID NO 25
<211> LENGTH: 20
<212> TYPE: DNA
<213> ORGANISM: Artificial Sequence
<220> FEATURE:
```

<223> OTHER INFORMATION: Primer PttCLE41-R

<400> SEQUENCE: 25 acccctταat tcccccatta                                             20

<210> SEQ ID NO 26
<211> LENGTH: 24
<212> TYPE: DNA
<213> ORGANISM: Artificial Sequence
<220> FEATURE:
<223> OTHER INFORMATION: Primer PttPXYF

<400> SEQUENCE: 26
caccatgaaa ctcccttttc tttt                                        24

<210> SEQ ID NO 27
<211> LENGTH: 20
<212> TYPE: DNA
<213> ORGANISM: Artificial Sequence
<220> FEATURE:
<223> OTHER INFORMATION: PttPXY-R

<400> SEQUENCE: 27
acattcgact gcaggctttt                                             20

<210> SEQ ID NO 28
<211> LENGTH: 88
<212> TYPE: PRT
<213> ORGANISM: Arabidopsis thaliana

<400> SEQUENCE: 28

Met Arg Ser Pro His Ile Thr Ile Ser Leu Val Phe Leu Phe Phe Leu
1               5                   10                  15

Phe Leu Ile Ile Gln Thr His Gln Arg Thr Ile Asp Gln Thr His Gln
            20                  25                  30

Ile Gly Ser Asn Val Gln His Val Ser Asp Met Ala Val Thr Ser Pro
        35                  40                  45

Glu Gly Lys Arg Arg Glu Arg Phe Arg Val Arg Pro Met Thr Thr
    50                  55                  60

Trp Leu Lys Gly Lys Met Ile Gly Ala Asn Glu His Gly Val Pro Ser
65                  70                  75                  80

Gly Pro Asn Pro Ile Ser Asn Arg
                85

<210> SEQ ID NO 29
<211> LENGTH: 267
<212> TYPE: DNA
<213> ORGANISM: Arabidopsis thaliana

<400> SEQUENCE: 29
atgagatctc ctcacatcac catttcactt gttttcttgt tctttctttt tctaatcatc      60
caaacccatc aaagaaccat tgatcaaact caccagattg ctccaatgt tcaacatgtc     120 agtgacatgg cggtgacttc gcctgaaggg aaaagaagag agaggtttag agttcggcgg     180
ccgatgacga catggctgaa gggaaagatg atcggtgcca atgaacatgg agtcccaagt     240
ggtccaaatc ccatctccaa taggtag                                        267

<210> SEQ ID NO 30
<211> LENGTH: 137
<212> TYPE: PRT
<213> ORGANISM: Unknown

-continued

```
<220> FEATURE:
<223> OTHER INFORMATION: homologous sequence from other plant sequence
      compared to CLE41 and CLE42
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (61)..(63)
<223> OTHER INFORMATION: Xaa can be any naturally occurring amino acid

<400> SEQUENCE: 30

Met Asp Ile Glu Pro Leu Trp Ala Leu Gly Gly Trp Phe Leu Phe Ser
1               5                   10                  15

Ile Thr Cys Met Ala Thr Pro Lys Ser Gln Ser Thr Ile Ser Xaa Xaa
            20                  25                  30

Xaa Glu Thr Phe Lys Arg Ser His His Phe Phe Leu Phe Leu Ala Leu
        35                  40                  45

Leu Phe Val Phe Ile Leu Leu Thr Ser Pro Ser Lys Xaa Xaa Xaa Pro
    50                  55                  60

Ile Asn Pro Thr Asn Thr Val Ala Ser Ile Ser Ile Lys Arg Leu Leu
65                  70                  75                  80

Leu Glu Ser Ser Glu Pro Ala Ser Thr Thr Met Asn Leu His Pro Lys
                85                  90                  95

His Thr Gln Gly Thr Arg Thr Ser Ser Ser Ser Ser Pro Pro Ser
            100                 105                 110

Ser Lys Ser Thr Arg Lys Lys Phe Gly Ala Gln Ala His Glu Val Pro
        115                 120                 125

Ser Gly Pro Asn Pro Ile Ser Asn Arg
        130                 135

<210> SEQ ID NO 31
<211> LENGTH: 118
<212> TYPE: PRT
<213> ORGANISM: Unknown
<220> FEATURE:
<223> OTHER INFORMATION: homologous sequence from other plant sequence
      compared to CLE41 and CLE42
<220> FEATURE:
<221> NAME/KEY: misc_feature
<222> LOCATION: (42)..(44)
<223> OTHER INFORMATION: Xaa can be any naturally occurring amino acid
<220> FEATURE:
<221> NAME/KEY: misc_feature
<222> LOCATION: (91)..(92)
<223> OTHER INFORMATION: Xaa can be any naturally occurring amino acid

<400> SEQUENCE: 31

Met Ala Thr Pro Lys Thr Gln Ser Thr Thr Ile Ser Asp His Gln Thr
1               5                   10                  15

Cys Thr Lys Ala His His Phe Leu Ser Leu Leu Ala Leu Leu Phe Ile
            20                  25                  30

Phe Ile Leu Leu Thr Thr Ser Thr Lys Xaa Xaa Xaa Pro Ile Asn Pro
        35                  40                  45

Thr Asn Met Ala Ala Ser Ile Ser Ile Lys Arg Leu Leu Leu Glu Ser
    50                  55                  60

Ser Glu Pro Ala Ser Thr Thr Met Asn Leu His Pro Lys Gln Thr Gln
65                  70                  75                  80

Asp Ala Arg Thr Ser Ser Ser Ser Thr Ser Xaa Xaa Ser Ser Lys Ser
                85                  90                  95

Thr Arg Thr Lys Phe Gly Ala Ala Ala His Glu Val Pro Ser Gly Pro
```

Asn Pro Ile Ser Asn Arg
        115

<210> SEQ ID NO 32
<211> LENGTH: 117
<212> TYPE: PRT
<213> ORGANISM: Unknown
<220> FEATURE:
<223> OTHER INFORMATION: homologous sequence from other plant sequence
      compared to CLE41 and CLE42
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (91)..(93)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid

<400> SEQUENCE: 32

Met Ala Thr Thr Ile Asp Gln Thr Ser Ile Lys Ser Xaa Leu His Phe
1               5                   10                  15

His Gln Val Ile Arg Leu Ile Ile Thr Ile Ile Phe Leu Ala Phe Leu
            20                  25                  30

Phe Leu Ile Gly Pro Thr Ser Ser Met Asn His His Leu His Glu Ser
        35                  40                  45

Ser Ser Lys Asn Thr Met Ala Pro Ser Lys Arg Phe Leu Leu Gln Pro
    50                  55                  60

Ser Thr Pro Ser Ser Thr Met Lys Met Arg Pro Thr Ala His Pro
65                  70                  75                  80

Arg Arg Ser Gly Thr Ser Ser Ser Ala Xaa Xaa Xaa Arg Lys Xaa
                85                  90                  95

Arg Arg Arg Glu Phe Arg Ala Glu Ala His Glu Val Pro Ser Gly Pro
            100                 105                 110

Asn Pro Ile Ser Asn
        115

<210> SEQ ID NO 33
<211> LENGTH: 118
<212> TYPE: PRT
<213> ORGANISM: Unknown
<220> FEATURE:
<223> OTHER INFORMATION: homologous sequence from other plant sequence
      compared to CLE41 and CLE42
<220> FEATURE:
<221> NAME/KEY: misc_feature
<222> LOCATION: (92)..(93)
<223> OTHER INFORMATION: Xaa can be any naturally occurring amino acid

<400> SEQUENCE: 33

Met Ala Ser Asp Val Gly Ser Pro Tyr Pro Thr Ser Leu Thr Ile Leu
1               5                   10                  15

Phe Phe Leu Leu Ile Met Ser His Thr Thr Met Ala Ile Lys Glu His
            20                  25                  30

Arg Phe Leu Leu Gly Thr Ser Arg Asp Gly Glu Tyr Ile Lys Lys Asn
        35                  40                  45

Asp Met Glu Tyr Phe Ala Asn Arg Arg His Asp Met Gly Asn Ala Lys
    50                  55                  60

```
Thr Val Ser Lys Ala Asn Ile Ile His Ile Pro Pro Ser Ser Arg
 65                  70                  75                  80

Arg Arg Gly Arg Phe Arg Ala His Arg Ser Pro Xaa Xaa Leu Pro Trp
                 85                  90                  95

Gln Glu Gly Val Phe Asn Asp Ser Ala His Glu Val Pro Ser Gly Pro
            100                 105                 110

Asn Pro Ile Ser Asn Arg
        115
```

<210> SEQ ID NO 34
<211> LENGTH: 118
<212> TYPE: PRT
<213> ORGANISM: Unknown
<220> FEATURE:
<223> OTHER INFORMATION: homologous sequence from other plant sequence
      compared to CLE41 and CLE42
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (92)..(93)
<223> OTHER INFORMATION: Xaa can be any naturally occurring amino acid

<400> SEQUENCE: 34

```
Met Ala Ser Asp Val Gly Ser Pro Asn Leu Thr Ser Leu Thr Ile Leu
 1               5                  10                  15

Phe Phe Leu Leu Ile Met Phe His Thr Thr Met Ala Asn Lys Asp His
                 20                  25                  30

Arg Phe Leu Leu Ser Thr Thr Arg Asp Gly Gly Tyr Phe Lys Lys Ser
             35                  40                  45

Leu Met Glu Phe Ser Thr Thr Arg Xaa Pro Asp Met Gly Asn Ala Lys
 50                  55                  60

Thr Val Ser Lys Ala Asn Val Ile His Ile Pro Pro Gln Ser Ser Arg
 65                  70                  75                  80

Arg Arg Gly Arg Phe Arg Ala His Arg Ser Pro Xaa Xaa Leu Pro Trp
                 85                  90                  95

Gln Glu Gly Ile Phe Ser Ala Ser Ala His Glu Val Pro Ser Gly Pro
            100                 105                 110

Asn Pro Ile Ser Asn Arg
        115
```

<210> SEQ ID NO 35
<211> LENGTH: 61
<212> TYPE: PRT
<213> ORGANISM: Unknown
<220> FEATURE:
<223> OTHER INFORMATION: homologous sequence from other plant sequence
      compared to CLE41 and CLE42
<220> FEATURE:
<221> NAME/KEY: misc_feature
<222> LOCATION: (21)..(26)
<223> OTHER INFORMATION: Xaa can be any naturally occurring amino acid
<220> FEATURE:
<221> NAME/KEY: misc_feature
<222> LOCATION: (29)..(38)
<223> OTHER INFORMATION: Xaa can be any naturally occurring amino acid

<400> SEQUENCE: 35

```
Met Gln Met Ile Asp Ala Phe Thr Leu Leu Val Leu Ser Phe Met Leu
 1               5                  10                  15

Arg His Lys Gln Xaa Xaa Xaa Xaa Xaa Xaa Val Ala Xaa Xaa Xaa Xaa
                 20                  25                  30
```

```
Xaa Xaa Xaa Xaa Xaa Xaa Glu Lys Arg Ile His Lys Ser Pro Ser Gly
            35                  40                  45

Pro Asn Pro Val Gly Asn His Asn Pro Pro Ser Lys Gln
        50                  55                  60

<210> SEQ ID NO 36
<211> LENGTH: 111
<212> TYPE: PRT
<213> ORGANISM: Unknown
<220> FEATURE:
<223> OTHER INFORMATION: homologous sequence from other plant sequence
      compared to CLE41 and CLE42
<220> FEATURE:
<221> NAME/KEY: misc_feature
<222> LOCATION: (25)..(37)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (64)..(65)
<223> OTHER INFORMATION: Xaa can be any naturally occurring amino acid
<220> FEATURE:
<221> NAME/KEY: misc_feature
<222> LOCATION: (71)..(89)
<223> OTHER INFORMATION: Xaa can be any naturally occurring amino acid

<400> SEQUENCE: 36

Met Arg Arg His Asp Ile Ile Ile Lys Leu Leu Leu Met Cys Ile
1               5                   10                  15

Leu Leu Ser Arg Phe Val Thr Arg Xaa Xaa Xaa Xaa Xaa Xaa Xaa
            20                  25                  30

Xaa Xaa Xaa Xaa Xaa Glu Cys Gln Glu Val His Phe Lys Ile Gly Xaa
            35                  40                  45

Pro Ala Lys Ile Ile Ala Lys Pro Asn Asn Ala Arg Val Met Pro Xaa
        50                  55                  60

Xaa Thr Trp Gly Glu Glu Xaa Xaa Xaa Xaa Xaa Xaa Xaa Xaa Xaa
65              70                  75                  80

Xaa Xaa Xaa Xaa Xaa Xaa Xaa Xaa Xaa Lys Lys Trp His Lys His Pro
            85                  90                  95

Ser Gly Pro Asn Pro Thr Gly Asn Arg His Pro Pro Val Lys His
            100                 105                 110

<210> SEQ ID NO 37
<211> LENGTH: 118
<212> TYPE: PRT
<213> ORGANISM: Unknown
<220> FEATURE:
<223> OTHER INFORMATION: homologous sequence from other plant sequence
      compared to CLE41 and CLE42
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (40)..(44)
<223> OTHER INFORMATION: Xaa can be any naturally occurring amino acid
<220> FEATURE:
<221> NAME/KEY: misc_feature
<222> LOCATION: (87)..(94)
<223> OTHER INFORMATION: Xaa can be any naturally occurring amino acid

<400> SEQUENCE: 37

Met Ala Arg Ala Arg Trp Ile Gly Asp Gly Arg Arg Pro Ala Ala Ala
```

```
                1               5                  10                 15
Leu Pro Leu Leu Gly Leu Cys Ala Phe Leu Cys Ala Val Met Leu Val
                20                 25                 30

Val Ser Leu Ala Pro Xaa Pro Xaa Xaa Xaa Xaa Xaa Pro Gly Glu Glu
        35                 40                 45

Glu Glu Glu Ala Lys Val Arg Ser Ser Ser Leu Pro Ala Ala Ala Thr
    50                 55                 60

Ser Val Pro Ala Gly Gly Arg Arg Leu Leu Pro Ala Ala Arg Thr
65                  70                 75                 80

Arg Arg Phe Arg Pro Arg Xaa Xaa Xaa Xaa Xaa Xaa Xaa Arg Trp
                85                 90                 95

Asn Ser Ala Gly Ile Asp Asp Ser Lys His Glu Val Pro Ser Gly Pro
            100                105                110

Asn Pro Asp Ser Asn Arg
            115
```

<210> SEQ ID NO 38
<211> LENGTH: 121
<212> TYPE: PRT
<213> ORGANISM: Unknown
<220> FEATURE:
<223> OTHER INFORMATION: homologous sequence from other plant sequence
      compared to CLE41 and CLE42
<220> FEATURE:
<221> NAME/KEY: misc_feature
<222> LOCATION: (96)..(96)
<223> OTHER INFORMATION: Xaa can be any naturally occurring amino acid

<400> SEQUENCE: 38

```
Met Asp Thr Ala Arg Pro Val His Pro Leu Arg Val His Gly Glu Ser
1               5                  10                 15

Ile Arg Gly Leu Leu Leu Leu Leu Leu Phe Val Val Gln Cys Ser
            20                 25                 30

Ile Leu Ser Cys Cys Leu Ala His Ala Ala Ala Ala Asp Ala Val
        35                 40                 45

Asp Arg Asp Asp Pro Val Val Thr Ala Thr Ala Gly Arg Gly Arg Arg
    50                 55                 60

Phe Leu Pro Ser Pro Ala Leu Gln Leu His Ser Val Gln Val Asn Val
65                  70                 75                 80

Ala Ala His Pro Trp Ser Lys Glu Arg Arg Ser Arg Arg Arg Xaa
                85                 90                 95

Arg Arg Arg Arg Ala Ala Thr Ile Met Ala Val Ser Lys His Gln Val
            100                105                110

Pro Thr Gly Ala Asn Pro Asp Ser Asn
            115                120
```

<210> SEQ ID NO 39
<211> LENGTH: 118
<212> TYPE: PRT
<213> ORGANISM: Artificial Sequence
<220> FEATURE:
<223> OTHER INFORMATION: Consensus sequence from other plant sequences
      and CLE41 and CLE42
<220> FEATURE:
<221> NAME/KEY: misc_feature
<222> LOCATION: (4)..(11)
<223> OTHER INFORMATION: Xaa can be any naturally occurring amino acid
<220> FEATURE:
<221> NAME/KEY: misc_feature
<222> LOCATION: (13)..(18)
<223> OTHER INFORMATION: Xaa can be any naturally occurring amino acid
<220> FEATURE:

```
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (24)..(26)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid
<220> FEATURE:
<221> NAME/KEY: misc_feature
<222> LOCATION: (37)..(63)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (83)..(100)
<223> OTHER INFORMATION: Xaa can be any naturally occurring amino acid
<220> FEATURE:
<221> NAME/KEY: misc_feature
<222> LOCATION: (102)..(104)
<223> OTHER INFORMATION: Xaa can be any naturally occurring amino acid

<400> SEQUENCE: 39

Met Ala Thr Xaa Xaa Xaa Xaa Xaa Xaa Xaa Xaa Ser Xaa Xaa Xaa Xaa
1               5                   10                  15

Xaa Xaa Leu Leu Xaa Leu Phe Xaa Xaa Xaa Leu Ala Ile Leu Xaa Xaa
            20                  25                  30

Xaa Xaa Leu Leu Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Ser
    50                  55                  60

Ser Val Xaa Xaa Ser Xaa Thr Met Xaa Leu Xaa Pro Xaa Ala Ser Xaa
65                  70                  75                  80

Arg Arg Xaa Xaa Xaa Xaa Xaa Xaa Xaa Xaa Xaa Xaa Xaa Xaa Xaa Xaa
            85                  90                  95

Xaa Xaa Xaa Xaa Phe Xaa Xaa Xaa Ala His Glu Val Pro Ser Gly Pro
            100                 105                 110

Asn Pro Ile Ser Asn Arg
            115
```